US011266722B2

(12) United States Patent
Braddock et al.

(10) Patent No.: US 11,266,722 B2
(45) Date of Patent: *Mar. 8, 2022

(54) COMPOSITIONS AND METHODS FOR TREATING PATHOLOGICAL CALCIFICATION AND OSSIFICATION

(71) Applicant: YALE UNIVERSITY, New Haven, CT (US)

(72) Inventors: Demetrios Braddock, Guilford, CT (US); Ronald Albright, Guilford, CT (US)

(73) Assignee: Yale University, New Haven, CT (US)

( * ) Notice: Subject to any disclaimer, the term of this patent is extended or adjusted under 35 U.S.C. 154(b) by 50 days.

This patent is subject to a terminal disclaimer.

(21) Appl. No.: 16/813,315

(22) Filed: Mar. 9, 2020

(65) Prior Publication Data

US 2020/0237882 A1    Jul. 30, 2020

Related U.S. Application Data

(63) Continuation of application No. 16/033,948, filed on Jul. 12, 2018, now Pat. No. 10,624,958, which is a continuation of application No. 15/686,972, filed on Aug. 25, 2017, now Pat. No. 10,052,367, which is a continuation of application No. 14/765,514, filed as application No. PCT/US2014/015945 on Feb. 12, 2014, now Pat. No. 9,744,219.

(60) Provisional application No. 61/904,786, filed on Nov. 15, 2013, provisional application No. 61/764,297, filed on Feb. 13, 2013.

(51) Int. Cl.
*C12N 9/14* (2006.01)
*A61K 38/46* (2006.01)
*C12N 9/16* (2006.01)

(52) U.S. Cl.
CPC ............ *A61K 38/465* (2013.01); *A61K 38/46* (2013.01); *C12N 9/14* (2013.01); *C12N 9/16* (2013.01); *C12Y 301/04001* (2013.01); *C12Y 306/01009* (2013.01); *C07K 2319/30* (2013.01)

(58) Field of Classification Search
CPC ............... A61K 9/00; A61K 9/10; C12N 9/14
See application file for complete search history.

(56) References Cited

U.S. PATENT DOCUMENTS

| | | | |
|---|---|---|---|
| 5,428,130 A | 6/1995 | Capon et al. | |
| 6,043,056 A | 3/2000 | Yue et al. | |
| 6,358,923 B1 | 3/2002 | Yue et al. | |
| 7,323,542 B2 | 1/2008 | Balian et al. | |
| 7,888,372 B2 | 2/2011 | Millan et al. | |
| 8,846,603 B2 | 9/2014 | Quinn et al. | |
| 9,744,219 B2* | 8/2017 | Braddock | C12Y 301/04001 |
| 9,913,881 B2 | 3/2018 | Braddock et al. | |
| 10,052,367 B2* | 8/2018 | Braddock | A61P 19/00 |
| 10,064,917 B2 | 9/2018 | Braddock et al. | |
| 10,213,483 B2 | 2/2019 | Otterlei et al. | |
| 10,213,484 B2 | 2/2019 | Braddock et al. | |
| 10,517,927 B2 | 12/2019 | Braddock et al. | |
| 10,583,170 B2 | 3/2020 | Braddock et al. | |
| 10,624,958 B2 | 4/2020 | Braddock et al. | |
| 2007/0015145 A1 | 1/2007 | Woolf et al. | |
| 2014/0154774 A1 | 6/2014 | Quinn et al. | |
| 2014/0377859 A1 | 12/2014 | Quinn et al. | |
| 2015/0024460 A1 | 1/2015 | Quinn et al. | |

FOREIGN PATENT DOCUMENTS

| | | | |
|---|---|---|---|
| EP | 3298140 A1 | | 3/2018 |
| RU | 2013142583 A | | 4/2015 |
| WO | 02092020 A2 | | 11/2002 |
| WO | 2011113027 A2 | | 9/2011 |
| WO | 2012125182 A1 | | 9/2012 |
| WO | 2014126965 A2 | | 8/2014 |
| WO | 2016100803 | * | 6/2016 |
| WO | 2016100803 A2 | | 6/2016 |
| WO | 2016187408 A1 | | 11/2016 |

OTHER PUBLICATIONS

European Supplemental Partial Search Report for European Patent Application No. 14751154.7 dated Nov. 7, 2016.
Extended European Search Report for European Patent Application No. 14751154.7 dated Feb. 16, 2017.
PCT International Search Report and Written Opinion for PCT International Application No. PCT/US2014/015945 dated Jul. 30, 2014.
Albright, et al., "ENPP1-Fc prevents mortality and vascular calcifications in rodent model of generalized arterial calcification of infancy", Nat Commun. 6, 2015, 10006.
Albright, et al., "Molecular basis of purinergic signal metabolism by ectonucleotide pyrophosphatase/phosphodiesterases 4 and 1 and implications in stroke", J Biol Chem. 289(6), 2014, 3294-3306.
Albright, et al., "NPP4 is a procoagulant enzyme on the surface of vascular endothelium", Blood. 120(22), 2012, 4432-4440.
Calvert, et al., "The Provisional Patent Application: What You Need to Know", Inventors Eye. United States Patent and Trademark Office <www.uspto.gov/ learning-and-resources/newsletter/inventors-eye/provisional-patent-application-what-you-need-know>, Apr. 2010, 5 pages.
Cimpean, et al., "Substrate-specifying determinants of the nucleotide pyrophosphatases/phosphodiesterases NPP1 and NPP2", Biochem J. 381(Pt 1), 2004, 71-77.

(Continued)

*Primary Examiner* — Karen Cochrane Carlson
(74) *Attorney, Agent, or Firm* — Saul Ewing Arnstein & Lehr LLP; Kathryn Doyle; Domingos J. Silva

(57) ABSTRACT

The present invention includes compositions and methods for treating disease and disorders associated with pathological calcification or pathological ossification by modulating the level or activity of NPP1 or a mutant thereof, or a mutant NPP4 modified to exhibit ATP hydrolase activity similar to the hydrolase activity of NPP1.

20 Claims, 22 Drawing Sheets

Specification includes a Sequence Listing.

(56) References Cited

OTHER PUBLICATIONS

Gijsbers, et al., "Functional characterization of the non-catalytic ectodomains of the nucleotide pyrophosphatase/phosphodiesterase NPP1", Biochem J. 371 (Pt 2), Apr. 15, 2003, 321-330.

Goding, et al., "Physiological and pathophysiological functions of the ecto-nucleotide pyrophosphatase/phosphodiesterase family", Biochim Biophys Acta. 1638(1), 2003, 1-19.

Jansen, et al., "Proteolytic maturation and activation of autotaxin (NPP2), a secreted metastasis-enhancing lysophospholipase D", J Cell Sci. 118(Pt 14), 2005, 3081-3089.

Jansen, et al., "Structure of NPP1, an ectonucleotide pyrophosphatase/phosphodiesterase involved in tissue calcification", Structure. 20(11), 2012, 1948-1959.

Johnson, et al., "Differential mechanisms of inorganic pyrophosphate production by plasma cell membrane glycoprotein-1 and B10 in chondrocytes", Arthritis Rheum. 42(9), 1999, 1986-1997.

Johnson, et al., "Linked deficiencies in extracellular PP(i) and osteopontin mediate pathologic calcification associated with defective PC-1 and ANK expression", J Bone Miner Res. 18(6), 2003, 994-1004.

Lee, et al., "Cloning, chromosomal localization, and tissue expression of autotaxin from human teratocarcinoma cells", Biochem Biophys Res Commun. 218(3, 1996, 714-719.

Schetter, et al., "Nucleoporins NPP-1, NPP-3, NPP-4, NPP-11 and NPP-13 are required for proper spindle orientation in C. elegans", Dev Biol. 289(2), Jan. 15, 2006, 360-371.

Shankar, et al., "Progeria-A Brief Review", International Journal of Pharma and Bio Sciences 2, 2010, 1-14.

Stefan, et al., "NPP-type ectophosphodiesterases: unity in diversity.", Trends Biochem Sci. 30(10), Oct. 2005, 542-550.

Terkeltaub, "Physiologic and pathologic functions of the NPP nucleotide pyrophosphatase/phosphodiesterase family focusing on NPP1 in calcification", Purinergic Signal. 2(2), Jun. 2, 2006, 371-377.

Whisstock, et al., "Prediction of proteinfunction fromprotein sequence and structure", Quarterly Reviews of Biophysics 36, 3 (2003), pp. 2003, 307-340.

Witkowski, et al., "Conversion of a Beta-Ketoacyl Synthase to a Malonyl Decarboxylase by Replacement of the Active-Site Cysteine With Glutamine", Biochemistry 38(36), Sep. 1999, 11643-11650.

Zhang, et al., "The interaction of cationic polymers and their bisphosphonate derivatives with hydroxyapatite", Macromol Biosci. 7(5), May 10, 2007, 656-670 (Abstract Only).

Mus musculus domesticus ecto-nucleotide pyrophosphatase/phosphodiesterase-1 mRNA, complete cds, GenBank J02700.2, Aug. 12, 2020 searched.

Buckley, et al., "Plasma cell membrane glycoprotein PC-1. cDNA cloning of the human molecule, amino acid sequence, and chromosomal location", J Biol Chem. 265(29), Oct. 1990, 17506-17511.

Okawa, et al., "Mutation in Npps in a mouse model of ossification of the posterior longitudinal ligament of the spine", Nat Genet. 19(3), Jul. 1998, 271-273.

Johnson, et al., "Matrix vesicle plasma cell membrane glycoprotein-1 regulates mineralization by murine osteoblastic MC3T3 cells", J Bone Miner Res. 14(6), Jun. 1999, 883-892.

Kato, et al., "Crystal structure of Enpp1, an extracellular glycoprotein involved in bone mineralization and insulin signaling", Proc Natl Acad Sci U S A. 109(42), Oct. 2012, 16876-16881.

Li, et al., "Inhibition of Tissue-Nonspecific Alkaline Phosphatase Attenuates Ectopic Mineralization in the Abcc6 -/-Mouse Model of PXE but Not in the Enpp1 Mutant Mouse Models of GACI", J Invest Dermatol. 139(2), Feb. 2019, 360-368.

Millán, et al., "Enzyme replacement therapy for murine hypophosphatasia", J Bone Miner Res. 23(6), Jun. 2008, 777-787.

Van Meeteren, et al., "Inhibition of autotaxin by lysophosphatidic acid and sphingosine 1-phosphate", J Biol Chem. 280(22), Jun. 2005, 21155-21161.

* cited by examiner

NPP1

NPP4

FIG. 9C
positive
FIG. 9D
negative
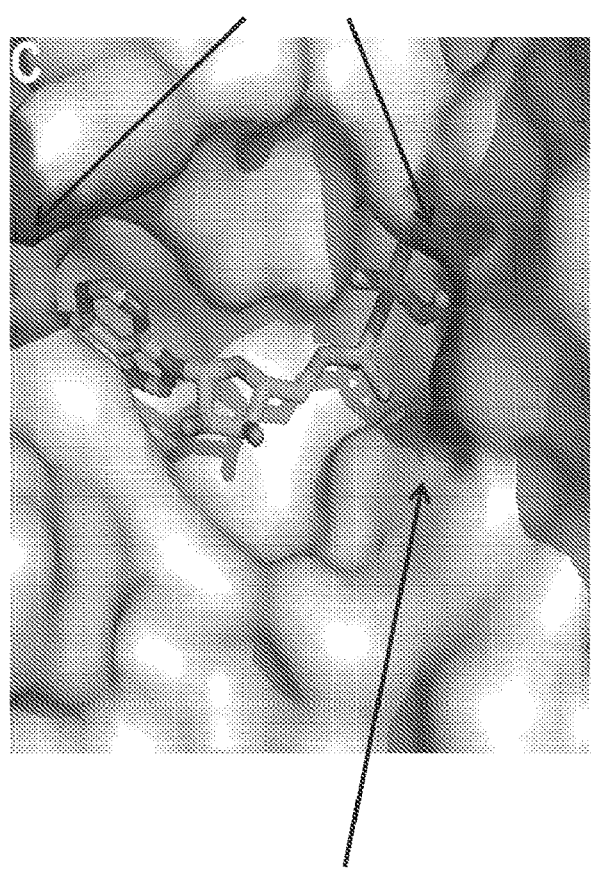
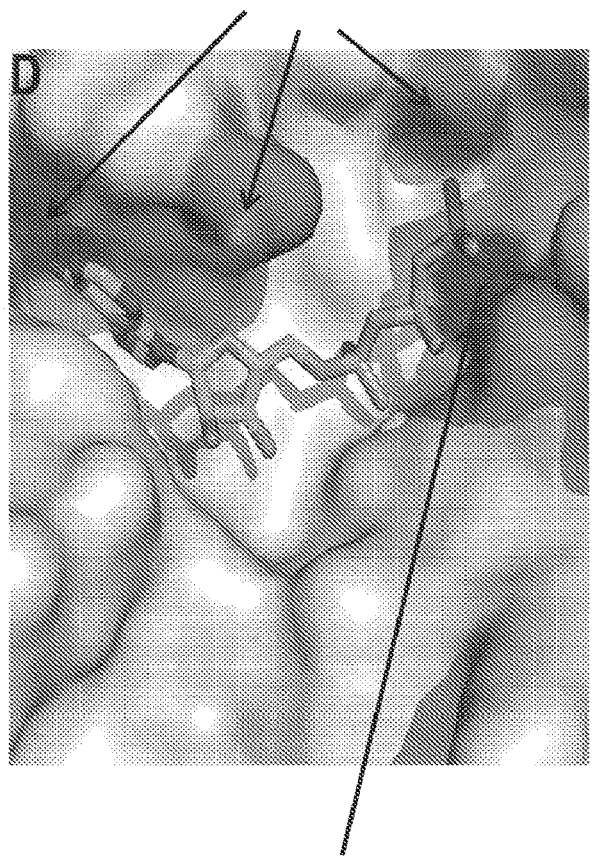
positive
positive positive
negative negative
negative  positive

SEQUENCE LISTING

```
<160> NUMBER OF SEQ ID NOS: 3

<210> SEQ ID NO 1
<211> LENGTH: 925
<212> TYPE: PRT
<213> ORGANISM: Homo sapiens
<220> FEATURE:
<221> NAME/KEY: misc_feature
<223> OTHER INFORMATION: NPP1 Amino Acid Sequence

<400> SEQUENCE: 1

Met Glu Arg Asp Gly Cys Ala Gly Gly Gly Ser Arg Gly Gly Glu Gly
1               5                   10                  15

Gly Arg Ala Pro Arg Glu Gly Pro Ala Gly Asn Gly Arg Asp Arg Gly
            20                  25                  30
```

-continued

Arg Ser His Ala Ala Glu Ala Pro Gly Asp Pro Gln Ala Ala Ser
         35                  40                  45

Leu Leu Ala Pro Met Asp Val Gly Glu Pro Leu Glu Lys Ala Ala
 50                  55                  60

Arg Ala Arg Thr Ala Lys Asp Pro Asn Thr Tyr Lys Val Leu Ser Leu
 65                  70                  75                  80

Val Leu Ser Val Cys Val Leu Thr Thr Ile Leu Gly Cys Ile Phe Gly
                 85                  90                  95

Leu Lys Pro Ser Cys Ala Lys Glu Val Lys Ser Cys Lys Gly Arg Cys
             100                 105                 110

Phe Glu Arg Thr Phe Gly Asn Cys Arg Cys Asp Ala Ala Cys Val Glu
         115                 120                 125

Leu Gly Asn Cys Cys Leu Asp Tyr Gln Glu Thr Cys Ile Glu Pro Glu
130                 135                 140

His Ile Trp Thr Cys Asn Lys Phe Arg Cys Gly Glu Lys Arg Leu Thr
145                 150                 155                 160

Arg Ser Leu Cys Ala Cys Ser Asp Asp Cys Lys Asp Lys Gly Asp Cys
                 165                 170                 175

Cys Ile Asn Tyr Ser Ser Val Cys Gln Gly Glu Lys Ser Trp Val Glu
             180                 185                 190

Glu Pro Cys Glu Ser Ile Asn Glu Pro Gln Cys Pro Ala Gly Phe Glu
         195                 200                 205

Thr Pro Pro Thr Leu Leu Phe Ser Leu Asp Gly Phe Arg Ala Glu Tyr
     210                 215                 220

Leu His Thr Trp Gly Gly Leu Leu Pro Val Ile Ser Lys Leu Lys Lys
225                 230                 235                 240

Cys Gly Thr Tyr Thr Lys Asn Met Arg Pro Val Tyr Pro Thr Lys Thr
                 245                 250                 255

Phe Pro Asn His Tyr Ser Ile Val Thr Gly Leu Tyr Pro Glu Ser His
             260                 265                 270

Gly Ile Ile Asp Asn Lys Met Tyr Asp Pro Lys Met Asn Ala Ser Phe
         275                 280                 285

Ser Leu Lys Ser Lys Glu Lys Phe Asn Pro Glu Trp Tyr Lys Gly Glu
290                 295                 300

Pro Ile Trp Val Thr Ala Lys Tyr Gln Gly Leu Lys Ser Gly Thr Phe
305                 310                 315                 320

Phe Trp Pro Gly Ser Asp Val Glu Ile Asn Gly Ile Phe Pro Asp Ile
                 325                 330                 335

Tyr Lys Met Tyr Asn Gly Ser Val Pro Phe Glu Glu Arg Ile Leu Ala
             340                 345                 350

Val Leu Gln Trp Leu Gln Leu Pro Lys Asp Glu Arg Pro His Phe Tyr
         355                 360                 365

Thr Leu Tyr Leu Glu Glu Pro Asp Ser Ser Gly His Ser Tyr Gly Pro
     370                 375                 380

Val Ser Ser Glu Val Ile Lys Ala Leu Gln Arg Val Asp Gly Met Val
385                 390                 395                 400

Gly Met Leu Met Asp Gly Leu Lys Glu Leu Asn Leu His Arg Cys Leu
                 405                 410                 415

Asn Leu Ile Leu Ile Ser Asp His Gly Met Glu Gln Gly Ser Cys Lys
             420                 425                 430

Lys Tyr Ile Tyr Leu Asn Lys Tyr Leu Gly Asp Val Lys Asn Ile Lys
         435                 440                 445

Val Ile Tyr Gly Pro Ala Ala Arg Leu Arg Pro Ser Asp Val Pro Asp

```
            450                 455                 460
Lys Tyr Tyr Ser Phe Asn Tyr Glu Gly Ile Ala Arg Asn Leu Ser Cys
465                 470                 475                 480

Arg Glu Pro Asn Gln His Phe Lys Pro Tyr Leu Lys His Phe Leu Pro
                    485                 490                 495

Lys Arg Leu His Phe Ala Lys Ser Asp Arg Ile Glu Pro Leu Thr Phe
                500                 505                 510

Tyr Leu Asp Pro Gln Trp Gln Leu Ala Leu Asn Pro Ser Glu Arg Lys
                515                 520                 525

Tyr Cys Gly Ser Gly Phe His Gly Ser Asp Asn Val Phe Ser Asn Met
            530                 535                 540

Gln Ala Leu Phe Val Gly Tyr Gly Pro Gly Phe Lys His Gly Ile Glu
545                 550                 555                 560

Ala Asp Thr Phe Glu Asn Ile Glu Val Tyr Asn Leu Met Cys Asp Leu
                565                 570                 575

Leu Asn Leu Thr Pro Ala Pro Asn Asn Gly Thr His Gly Ser Leu Asn
                580                 585                 590

His Leu Leu Lys Asn Pro Val Tyr Thr Pro Lys His Pro Lys Glu Val
            595                 600                 605

His Pro Leu Val Gln Cys Pro Phe Thr Arg Asn Pro Arg Asp Asn Leu
            610                 615                 620

Gly Cys Ser Cys Asn Pro Ser Ile Leu Pro Ile Glu Asp Phe Gln Thr
625                 630                 635                 640

Gln Phe Asn Leu Thr Val Ala Glu Glu Lys Ile Ile Lys His Glu Thr
                645                 650                 655

Leu Pro Tyr Gly Arg Pro Arg Val Leu Gln Lys Glu Asn Thr Ile Cys
                660                 665                 670

Leu Leu Ser Gln His Gln Phe Met Ser Gly Tyr Ser Gln Asp Ile Leu
            675                 680                 685

Met Pro Leu Trp Thr Ser Tyr Thr Val Asp Arg Asn Asp Ser Phe Ser
            690                 695                 700

Thr Glu Asp Phe Ser Asn Cys Leu Tyr Gln Asp Phe Arg Ile Pro Leu
705                 710                 715                 720

Ser Pro Val His Lys Cys Ser Phe Tyr Lys Asn Asn Thr Lys Val Ser
                725                 730                 735

Tyr Gly Phe Leu Ser Pro Pro Gln Leu Asn Lys Asn Ser Ser Gly Ile
                740                 745                 750

Tyr Ser Glu Ala Leu Leu Thr Thr Asn Ile Val Pro Met Tyr Gln Ser
            755                 760                 765

Phe Gln Val Ile Trp Arg Tyr Phe His Asp Thr Leu Leu Arg Lys Tyr
770                 775                 780

Ala Glu Glu Arg Asn Gly Val Asn Val Val Ser Gly Pro Val Phe Asp
785                 790                 795                 800

Phe Asp Tyr Asp Gly Arg Cys Asp Ser Leu Glu Asn Leu Arg Gln Lys
                805                 810                 815

Arg Arg Val Ile Arg Asn Gln Glu Ile Leu Ile Pro Thr His Phe Phe
                820                 825                 830

Ile Val Leu Thr Ser Cys Lys Asp Thr Ser Gln Thr Pro Leu His Cys
            835                 840                 845

Glu Asn Leu Asp Thr Leu Ala Phe Ile Leu Pro His Arg Thr Asp Asn
            850                 855                 860

Ser Glu Ser Cys Val His Gly Lys His Asp Ser Ser Trp Val Glu Glu
865                 870                 875                 880
```

```
Leu Leu Met Leu His Arg Ala Arg Ile Thr Asp Val Glu His Ile Thr
                885                 890                 895

Gly Leu Ser Phe Tyr Gln Gln Arg Lys Glu Pro Val Ser Asp Ile Leu
            900                 905                 910

Lys Leu Lys Thr His Leu Pro Thr Phe Ser Gln Glu Asp
        915                 920                 925

<210> SEQ ID NO 2
<211> LENGTH: 888
<212> TYPE: PRT
<213> ORGANISM: Homo sapiens
<220> FEATURE:
<221> NAME/KEY: misc_feature
<223> OTHER INFORMATION: NPP2 Amino Acid Sequence

<400> SEQUENCE: 2

Met Ala Arg Arg Ser Ser Phe Gln Ser Cys Gln Ile Ile Ser Leu Phe
1               5                   10                  15

Thr Phe Ala Val Gly Val Asn Ile Cys Leu Gly Phe Thr Ala His Arg
            20                  25                  30

Ile Lys Arg Ala Glu Gly Trp Glu Glu Gly Pro Pro Thr Val Leu Ser
        35                  40                  45

Asp Ser Pro Trp Thr Asn Ile Ser Gly Ser Cys Lys Gly Arg Cys Phe
    50                  55                  60

Glu Leu Gln Glu Ala Gly Pro Pro Asp Cys Arg Cys Asp Asn Leu Cys
65                  70                  75                  80

Lys Ser Tyr Thr Ser Cys Cys His Asp Phe Asp Glu Leu Cys Leu Lys
                85                  90                  95

Thr Ala Arg Gly Trp Glu Cys Thr Lys Asp Arg Cys Gly Glu Val Arg
            100                 105                 110

Asn Glu Glu Asn Ala Cys His Cys Ser Glu Asp Cys Leu Ala Arg Gly
        115                 120                 125

Asp Cys Cys Thr Asn Tyr Gln Val Val Cys Lys Gly Glu Ser His Trp
    130                 135                 140

Val Asp Asp Asp Cys Glu Glu Ile Lys Ala Ala Glu Cys Pro Ala Gly
145                 150                 155                 160

Phe Val Arg Pro Pro Leu Ile Ile Phe Ser Val Asp Gly Phe Arg Ala
                165                 170                 175

Ser Tyr Met Lys Lys Gly Ser Lys Val Met Pro Asn Ile Glu Lys Leu
            180                 185                 190

Arg Ser Cys Gly Thr His Ser Pro Tyr Met Arg Pro Val Tyr Pro Thr
        195                 200                 205

Lys Thr Phe Pro Asn Leu Tyr Thr Leu Ala Thr Gly Leu Tyr Pro Glu
    210                 215                 220

Ser His Gly Ile Val Gly Asn Ser Met Tyr Asp Pro Val Phe Asp Ala
225                 230                 235                 240

Thr Phe His Leu Arg Gly Arg Glu Lys Phe Asn His Arg Trp Trp Gly
                245                 250                 255

Gly Gln Pro Leu Trp Ile Thr Ala Thr Lys Gln Gly Val Lys Ala Gly
            260                 265                 270

Thr Phe Phe Trp Ser Val Val Ile Pro His Glu Arg Arg Ile Leu Thr
        275                 280                 285

Ile Leu Gln Trp Leu Thr Leu Pro Asp His Glu Arg Pro Ser Val Tyr
    290                 295                 300

Ala Phe Tyr Ser Glu Gln Pro Asp Phe Ser Gly His Lys Tyr Gly Pro
```

-continued

```
            305                 310                 315                 320
        Phe Gly Pro Glu Met Thr Asn Pro Leu Arg Glu Ile Asp Lys Ile Val
                        325                 330                 335
        Gly Gln Leu Met Asp Gly Leu Lys Gln Leu Lys Leu His Arg Cys Val
                        340                 345                 350
        Asn Val Ile Phe Val Gly Asp His Gly Met Glu Asp Val Thr Cys Asp
                        355                 360                 365
        Arg Thr Glu Phe Leu Ser Asn Tyr Leu Thr Asn Val Asp Asp Ile Thr
                370                 375                 380
        Leu Val Pro Gly Thr Leu Gly Arg Ile Arg Ser Lys Phe Ser Asn Asn
        385                 390                 395                 400
        Ala Lys Tyr Asp Pro Lys Ala Ile Ile Ala Asn Leu Thr Cys Lys Lys
                        405                 410                 415
        Pro Asp Gln His Phe Lys Pro Tyr Leu Lys Gln His Leu Pro Lys Arg
                        420                 425                 430
        Leu His Tyr Ala Asn Asn Arg Arg Ile Glu Asp Ile His Leu Leu Val
                        435                 440                 445
        Glu Arg Arg Trp His Val Ala Arg Lys Pro Leu Asp Val Tyr Lys Lys
                450                 455                 460
        Pro Ser Gly Lys Cys Phe Phe Gln Gly Asp His Gly Phe Asp Asn Lys
        465                 470                 475                 480
        Val Asn Ser Met Gln Thr Val Phe Val Gly Tyr Gly Ser Thr Phe Lys
                        485                 490                 495
        Tyr Lys Thr Lys Val Pro Pro Phe Glu Asn Ile Glu Leu Tyr Asn Val
                        500                 505                 510
        Met Cys Asp Leu Leu Gly Leu Lys Pro Ala Pro Asn Asn Gly Thr His
                        515                 520                 525
        Gly Ser Leu Asn His Leu Leu Arg Thr Asn Thr Phe Arg Pro Thr Met
                530                 535                 540
        Pro Glu Glu Val Thr Arg Pro Asn Tyr Pro Gly Ile Met Tyr Leu Gln
        545                 550                 555                 560
        Ser Asp Phe Asp Leu Gly Cys Thr Cys Asp Asp Lys Val Glu Pro Lys
                        565                 570                 575
        Asn Lys Leu Asp Glu Leu Asn Lys Arg Leu His Thr Lys Gly Ser Thr
                        580                 585                 590
        Glu Ala Glu Thr Arg Lys Phe Arg Gly Ser Arg Asn Glu Asn Lys Glu
                        595                 600                 605
        Asn Ile Asn Gly Asn Phe Glu Pro Arg Lys Glu Arg His Leu Leu Tyr
                610                 615                 620
        Gly Arg Pro Ala Val Leu Tyr Arg Thr Arg Tyr Asp Ile Leu Tyr His
        625                 630                 635                 640
        Thr Asp Phe Glu Ser Gly Tyr Ser Glu Ile Phe Leu Met Pro Leu Trp
                        645                 650                 655
        Thr Ser Tyr Thr Val Ser Lys Gln Ala Glu Val Ser Ser Val Pro Asp
                        660                 665                 670
        His Leu Thr Ser Cys Val Arg Pro Asp Val Arg Val Ser Pro Ser Phe
                        675                 680                 685
        Ser Gln Asn Cys Leu Ala Tyr Lys Asn Asp Lys Gln Met Ser Tyr Gly
                        690                 695                 700
        Phe Leu Phe Pro Pro Tyr Leu Ser Ser Ser Pro Glu Ala Lys Tyr Asp
        705                 710                 715                 720
        Ala Phe Leu Val Thr Asn Met Val Pro Met Tyr Pro Ala Phe Lys Arg
                        725                 730                 735
```

```
Val Trp Asn Tyr Phe Gln Arg Val Leu Val Lys Lys Tyr Ala Ser Glu
            740                 745                 750

Arg Asn Gly Val Asn Val Ile Ser Gly Pro Ile Phe Asp Tyr Asp Tyr
            755                 760                 765

Asp Gly Leu His Asp Thr Glu Asp Lys Ile Lys Gln Tyr Val Glu Gly
            770                 775                 780

Ser Ser Ile Pro Val Pro Thr His Tyr Tyr Ser Ile Ile Thr Ser Cys
785                 790                 795                 800

Leu Asp Phe Thr Gln Pro Ala Asp Lys Cys Asp Gly Pro Leu Ser Val
            805                 810                 815

Ser Ser Phe Ile Leu Pro His Arg Pro Asp Asn Glu Glu Ser Cys Asn
            820                 825                 830

Ser Ser Glu Asp Glu Ser Lys Trp Val Glu Glu Leu Met Lys Met His
            835                 840                 845

Thr Ala Arg Val Arg Asp Ile Glu His Leu Thr Ser Leu Asp Phe Phe
            850                 855                 860

Arg Lys Thr Ser Arg Ser Tyr Pro Glu Ile Leu Thr Leu Lys Thr Tyr
865                 870                 875                 880

Leu His Thr Tyr Glu Ser Glu Ile
            885
```

<210> SEQ ID NO 3
<211> LENGTH: 453
<212> TYPE: PRT
<213> ORGANISM: Homo sapiens
<220> FEATURE:
<221> NAME/KEY: misc_feature
<223> OTHER INFORMATION: NPP4 Amino Acid Sequence

<400> SEQUENCE: 3

```
Met Lys Leu Leu Val Ile Leu Leu Phe Ser Gly Leu Ile Thr Gly Phe
1               5                   10                  15

Arg Ser Asp Ser Ser Ser Leu Pro Pro Lys Leu Leu Leu Val Ser
            20                  25                  30

Phe Asp Gly Phe Arg Ala Asp Tyr Leu Lys Asn Tyr Glu Phe Pro His
            35                  40                  45

Leu Gln Asn Phe Ile Lys Glu Gly Val Leu Val Glu His Val Lys Asn
        50                  55                  60

Val Phe Ile Thr Lys Thr Phe Pro Asn His Tyr Ser Ile Val Thr Gly
65                  70                  75                  80

Leu Tyr Glu Glu Ser His Gly Ile Val Ala Asn Ser Met Tyr Asp Ala
            85                  90                  95

Val Thr Lys Lys His Phe Ser Asp Ser Asn Asp Lys Asp Pro Phe Trp
            100                 105                 110

Trp Asn Glu Ala Val Pro Ile Trp Val Thr Asn Gln Leu Gln Glu Asn
            115                 120                 125

Arg Ser Ser Ala Ala Ala Met Trp Pro Gly Thr Asp Val Pro Ile His
        130                 135                 140

Asp Thr Ile Ser Ser Tyr Phe Met Asn Tyr Asn Ser Ser Val Ser Phe
145                 150                 155                 160

Glu Glu Arg Leu Asn Asn Ile Thr Met Trp Leu Asn Asn Ser Asn Pro
            165                 170                 175

Pro Val Thr Phe Ala Thr Leu Tyr Trp Glu Glu Pro Asp Ala Ser Gly
            180                 185                 190

His Lys Tyr Gly Pro Glu Asp Lys Glu Asn Met Ser Arg Val Leu Lys
```

-continued

```
            195                 200                 205
Lys Ile Asp Asp Leu Ile Gly Asp Leu Val Gln Arg Leu Lys Met Leu
        210                 215                 220

Gly Leu Trp Glu Asn Leu Asn Val Ile Ile Thr Ser Asp His Gly Met
225                 230                 235                 240

Thr Gln Cys Ser Gln Asp Arg Leu Ile Asn Leu Asp Ser Cys Ile Asp
                245                 250                 255

His Ser Tyr Tyr Thr Leu Ile Asp Leu Ser Pro Val Ala Ala Ile Leu
            260                 265                 270

Pro Lys Ile Asn Arg Thr Glu Val Tyr Asn Lys Leu Lys Asn Cys Ser
        275                 280                 285

Pro His Met Asn Val Tyr Leu Lys Glu Asp Ile Pro Asn Arg Phe Tyr
    290                 295                 300

Tyr Gln His Asn Asp Arg Ile Gln Pro Ile Ile Leu Val Ala Asp Glu
305                 310                 315                 320

Gly Trp Thr Ile Val Leu Asn Glu Ser Ser Gln Lys Leu Gly Asp His
                325                 330                 335

Gly Tyr Asp Asn Ser Leu Pro Ser Met His Pro Phe Leu Ala Ala His
            340                 345                 350

Gly Pro Ala Phe His Lys Gly Tyr Lys His Ser Thr Ile Asn Ile Val
        355                 360                 365

Asp Ile Tyr Pro Met Met Cys His Ile Leu Gly Leu Lys Pro His Pro
    370                 375                 380

Asn Asn Gly Thr Phe Gly His Thr Lys Cys Leu Leu Val Asp Gln Trp
385                 390                 395                 400

Cys Ile Asn Leu Pro Glu Ala Ile Ala Ile Val Ile Gly Ser Leu Leu
                405                 410                 415

Val Leu Thr Met Leu Thr Cys Leu Ile Ile Ile Met Gln Asn Arg Leu
            420                 425                 430

Ser Val Pro Arg Pro Phe Ser Arg Leu Gln Leu Gln Glu Asp Asp Asp
        435                 440                 445

Asp Pro Leu Ile Gly
    450
```

COMPOSITIONS AND METHODS FOR TREATING PATHOLOGICAL CALCIFICATION AND OSSIFICATION

CROSS REFERENCE TO RELATED APPLICATIONS

The present application is a continuation of, and claims priority to, U.S. patent application Ser. No. 16/033,948, filed Jul. 12, 2018, now issued as U.S. Pat. No. 10,624,958, which is a continuation of, and claims priority to, U.S. patent application Ser. No. 15/686,972, filed Aug. 25, 2017, now issued as U.S. Pat. No. 10,052,367, which is a continuation of, and claims priority to, U.S. patent application Ser. No. 14/765,514, filed Aug. 3, 2015, now issued as U.S. Pat. No. 9,744,219, which is a 35 U.S.C. § 371 national phase application from, and claiming priority to, International Application No. PCT/US2014/015945, filed Feb. 12, 2014, and published under PCT Article 21(2) in English, which claims priority under 35 U.S.C. § 119(e) to U.S. Provisional Application No. 61/904,786, filed Nov. 15, 2013, and No. 61/764,297, filed Feb. 13, 2013, all of which applications are incorporated herein by reference in their entireties.

BACKGROUND OF THE INVENTION

Ectopic tissue mineralization is associated with numerous human diseases, including chronic joint disease and acutely fatal neonatal syndromes. To prevent unwanted tissue calcification, factors which promote and inhibit tissue mineralization must be kept in tight balance. Genetic analysis of human kindreds and animal models of diseases associated with ectopic calcification have identified the balance of extracellular inorganic pyrophosphate (PPi) and phosphate (Pi) as an important regulator of ectopic tissue mineralization (Terkeltaub, 2001, Am. J. Phys. Cell Phys., 281:C1-C11). The activity of three extracellular enzymes—Tissue Non-specific Alkaline Phosphatase (TNAP), Progressive Ankylosis Protein (ANK), and Ecto-Nucleotide Pyrophosphatase/Phosphodiesterase-1 (NPP1)—tightly control the concentration of Pi and PPi in mammals at 1-3 mM and 2-3 µM respectively. PPi is a regulator of biomineralization, inhibiting the formation of basic calcium phosphate from amorphous calcium phosphate.

Diseases of ectopic calcification range from ultra-rare fatal diseases of infancy to common ailments associated with aging in a large percentage of the human population. IIAC, also referred to as generalized arterial calcification of infancy (GACI), is a rare and fatal form of ectopic calcification present in a very small cohort of unrelated kindreds (approximately 200 reported cases), and is characterized by the calcification of the internal elastic lamina of muscular arteries and stenosis due to myointimal proliferation. While the clinical presentation of these patients is variable, this malady results in death in the neonatal period, usually by age 6 months. OPLL is a common form of human myelopathy caused by a compression of the spinal cord by ectopic ossification of the spinal ligaments (Stapleton et al., 2011. Neurosurgical Focus 30:E6). The disease occurs most frequently in the cervical spine, and was first described in the Japanese population where it has a prevalence of 1.9-4.3% of the entire population. The disease presentation is also variable, but several genes and proteins have emerged over the years as promising targets of etiologic investigation.

The human NPP family consists of seven extracellular, glycosylated proteins (i.e., NPP1, NPP2, NPP3, NPP4, NPP5, NPP6, and NPP7) that hydrolyze phosphodiester bonds (Bollen et al., 2000, Crit. Rev. Biochem. Mol. Biol. 35:393-432; Stefan et al., 2005, Trends Biochem. Sci. 30:542-550; Goding et al., 2003, Biochim. Biophys. Acta 1638:1-19). The enzymes are numbered in the order they were discovered. NPPs are cell-surface enzymes, with the exception of NPP2, which is exported to the plasma membrane but cleaved by furin and released into the extracellular fluid (Jansen et al., 2005, J. Cell Sci. 118:3081-3089). The enzymes have high degrees of sequence and structural homology, but exhibit a diverse substrate specificity that encompasses nucleotides to lipids.

NPP1 (also known as PC-1) is a type 2 extracellular membrane-bound glycoprotein located on the mineral-depositing matrix vesicles of osteoblasts and chondrocytes, and hydrolyzes extracellular nucleotides (principally ATP) into AMP and PPi (Bollen et al., 2000, Crit. Rev. Biochem. Mol. Biol. 35:393-432; Terkeltaub, 2006, Purinergic signaling 2:371-377). PPi functions as a potent inhibitor of ectopic tissue mineralization by binding to nascent hydroxyapatite (HA) crystals, thereby preventing the future growth of these crystals (Terkeltaub, 2006, Purinergic signaling 2:371-377; Addison et al., 2007, J. Biol. Chem. 282:15872-15873). NPP1 generates PPi via the hydrolysis of nucleotide triphosphates (NTP's), ANK transports intracellular PPi into the extracellular space, and TNAP removes PPi via the direct hydrolysis of PPi into Pi (FIG. 1).

NPP2 is a lysophospholipase-D enzyme that generates lyso-phosphatidic acid (LPA) from lyso-phosphocholine (Umezu-Goto et al., 2002, J. Cell Biol. 158:227-233). NPP4 was recently shown to be a di-adenosine triphosphate (Ap3A) hydrolase and a potent pro-coagulant factor on the surface of vascular surfaces (Albright et al., 2012, Blood 120:4432-4440). NPP5 remains uncharacterized, and NPP6 and NPP7 both hydrolyze lipid substrates; NPP6 is a lyso-phopholipase-C enzyme, and NPP7 is an alkaline sphingomyelinase (Duan et al., 2003, J. Biol. Chem. 278:38528-36; Sakagami et al., 2005, J. Biol. Chem. 23084-93).

The lack of production and purification of significant quantities of biologically active NPP proteins in this membrane bound protein family has previously hampered their study and characterization. Expression systems for soluble NPP4 and NPP1 have not been demonstrated for large scale protein production and purification. Mutations in NPP4 to alter the enzymatic activity of the enzyme from Ap3A to ATP have not been reported.

Extracellular nucleotides engage in paracrine and autocrine cell signaling by binding purinergic receptors on cell surfaces, resulting in a wide range of physiologic responses including platelet aggregation (Offermanns, 2006, Circ. Res. 99:1293-1304), bone development and remodeling (Terkeltaub, 2006, Purinergic Signalling 2:371-377), and endocrinopathies such as diabetes and obesity (Omatsu-Kanbe et al., 2002, Exper. Physiol. 87:643-652; Schodel et al., 2004, Biochem. Biophys. Res. Comm. 321:767-773). Purinergic P2X receptors present on cell surfaces are ion channels that bind mainly ATP, while P2Y receptors are cell surface G-protein coupled receptors that interact with a broader range of nucleotides. The concentration of extracellular purine substrates driving purinergic signaling is determined by the release of ectonucleotides via degranulation or cell lysis, the rate of ectonucleotide synthesis, and the catabolism of ectonucleotides by ectoenzymes.

Platelet aggregation is induced via interaction of extracellular ADP with platelet $P2Y_1$ and $P2Y_{12}$ purinergic receptors, resulting in rapid calcium influx followed by further platelet activation, degranulation, and irreversible shape change to extend the growing thrombus. Metabolism of extracellular ADP by membrane-bound CD39 on vascular endothelial cells and soluble phosphohydrolases in the platelet microenvironment rapidly degrade ADP into AMP and Pi, limiting the extension of the aggregatory burst of ADP to platelets in the immediate vicinity of the activated, degranulating platelets. AMP is further metabolized by membrane bound CD73 into adenosine, a potent antithrombotic signaling molecule which modulates vascular tone, decreases leukocyte adhesion, and limits thrombus formation. The release of platelet dense core granules disgorges high concentrations of ADP into the thrombotic microenvironment, further stimulating platelet aggregation.

Platelets dense-core granules also contain high concentrations of the dinucleotide Ap3A, which can reach local concentrations of over 100 µM upon platelet degranulation. The role of Ap3A in hemostasis has never been fully defined, but Ap3A has long been thought to represent more stable 'chemically masked' ADP which could be released into the thrombotic microenvironment to sustain platelet aggregation. Ap3A hydrolytic activity has been identified on the vascular surfaces of both bovine and porcine endothelial cells.

There is a need in the art for novel compositions and methods for treating diseases and disorders associated with pathological calcification and/or pathological ossification. Such compositions and methods should not undesirably disturb other physiologic processes. The present invention fulfills this need.

BRIEF SUMMARY OF THE INVENTION

In one aspect, the invention includes a method of treating or preventing a disease or disorder associated with pathological calcification or pathological ossification in a subject in need thereof, wherein the method comprises administering to the subject a therapeutically effective amount of a composition comprising at least one agent selected from the group consisting of an ecto-nucleotide pyrophosphate/phosphodiesterase-1 (NPP1) polypeptide and a fragment, derivative, mutant or mutant fragment thereof, and an activator of NPP1 polypeptide and a fragment, mutant or mutant fragment thereof, whereby the disease or disorder is treated or prevented in the subject.

In another aspect, the invention includes a method of treating a disease or disorder associated with pathological calcification or pathological ossification in a subject in need thereof, wherein the method comprises administering to the subject a therapeutically effective amount of a composition comprising at least one agent selected from the group consisting of an ecto-nucleotide pyrophosphate/phosphodiesterase-4 (NPP4) polypeptide and a fragment, derivative, mutant or mutant fragment thereof, and an activator of NPP4 polypeptide or fragment or mutant thereof.

In yet another aspect, the invention includes a composition comprising at least one agent selected from the group consisting of an ecto-nucleotide pyrophosphate/phosphodiesterase-1 (NPP1) polypeptide, an NPP1 polypeptide fragment, an NPP1 polypeptide derivative, a mutant NPP1 polypeptide, and a mutant NPP1 polypeptide fragment.

In yet another aspect, the invention includes a composition comprising at least one agent selected from the group consisting of an ecto-nucleotide pyrophosphate/phosphodiesterase-4 (NPP4) polypeptide, an NPP4 polypeptide fragment, an NPP4 polypeptide derivative, a mutant NPP4 polypeptide, and a mutant NPP4 polypeptide fragment.

In various embodiments of any of the above aspects or any other aspect of the invention delineated herein, the NPP1 polypeptide or a fragment, mutant or mutant fragment thereof comprises a soluble recombinant NPP1 polypeptide or a fragment, mutant or mutant fragment thereof. In certain embodiments of the aspects recited herein, the NPP1 polypeptide or a fragment, mutant or mutant fragment thereof lacks the NPP1 transmembrane domain. In other embodiments of the aspects recited herein, the NPP1 polypeptide or a fragment, mutant or mutant fragment thereof comprises an IgG Fc domain. In yet other embodiments of the aspects recited herein, the mutant NPP1 polypeptide or fragment thereof has lower Ap3A hydrolytic activity as compared to the corresponding wild-type NPP1 polypeptide or fragment thereof. In yet other embodiments of the aspects recited herein, the mutant NPP1 polypeptide or fragment thereof has substantially the same ATP hydrolytic activity as compared to the corresponding wild-type NPP1 polypeptide or fragment thereof. In yet other embodiments of the aspects recited herein, the mutant NPP1 polypeptide or fragment thereof has lower Ap3A hydrolytic activity and substantially the same ATP hydrolytic activity as compared to the corresponding wild-type NPP1 polypeptide or fragment thereof. In yet other embodiments of the aspects recited herein, the mutant NPP1 polypeptide or fragment thereof has a mutation in at least one position selected from the group consisting of Ser 532, Tyr 529, Tyr 451, Ile 450, Ser 381, Tyr 382, Ser 377, Phe 346, Gly 531, Ser 289, Ser 287, Ala 454, Gly 452, Gln 519, Glu 526, Lys 448, Glu 508, Arg 456, Asp 276, Tyr 434, Gln 519, Ser 525, Gly 342, Ser 343 and Gly 536, relative to SEQ ID NO:1.

In various embodiments of any of the above aspects or any other aspect of the invention delineated herein, the NPP1 polypeptide or a fragment, mutant or mutant fragment thereof comprises a polyaspartic acid domain. In certain embodiments of the aspects recited herein, the polyaspartic acid domain comprises from about 2 to about 20 or more sequential aspartic acid residues. In other embodiments of the aspects recited herein, the NPP1 polypeptide or a fragment, mutant or mutant fragment thereof comprises an NPP2 transmembrane domain. In yet other embodiments of the aspects recited herein, the activator of NPP1 activates at least one selected from the group consisting of: expression of NPP1 polypeptide or a fragment, mutant or mutant fragment thereof; and activity of NPP1 polypeptide or a fragment, mutant or mutant fragment thereof. In yet other embodiments of the aspects recited herein, the activator of NPP1 is at least one selected from the group consisting of a chemical compound, a protein, a peptide, a peptidomimetic, and a small molecule chemical compound.

In certain embodiments of the aspects recited herein, the at least one agent is administered acutely or chronically. In other embodiments of the aspects recited herein, the at least one agent is administered locally, regionally or systemically. In yet other embodiments of the aspects recited herein, the subject is human. In yet other embodiments of the aspects recited herein, the disease or disorder is at least one selected from the group consisting of idiopathic infantile arterial calcification (IIAC), ossification of the posterior longitudinal ligament (OPLL), hypophosphatemic rickets, osteoarthritis, and calcification of atherosclerotic plaques.

In various embodiments of any of the above aspects or any other aspect of the invention delineated herein, the NPP4 polypeptide or a fragment, mutant or mutant fragment thereof is a soluble recombinant NPP4 polypeptide or a fragment, mutant or mutant fragment thereof. In certain embodiments of the aspects recited herein, the mutant NPP4 polypeptide or fragment thereof comprises at least one mutation selected from the group consisting of D335, S92, D264, L265, S330, Q331, K332, and T323, relative to SEQ ID NO:3. In other embodiments of the aspects recited herein, the mutant NPP4 polypeptide or fragment thereof comprises at least one mutation which increases the ATP hydrolytic activity of the mutant NPP4 polypeptide or fragment thereof as compared to the corresponding wild-type NPP4 or fragment thereof. In yet other embodiments of the aspects recited herein, the mutant NPP4 polypeptide or fragment thereof comprises at least one mutation which increases the NPP1-like hydrolytic activity of the mutant NPP4 polypeptide or fragment thereof as compared to the corresponding wild-type NPP4 or fragment thereof. In yet other embodiments of the aspects recited herein, the mutant NPP4 polypeptide or fragment thereof comprises at least one mutation which increases the substrate selectivity of the mutant NPP4 polypeptide for ATP as compared to the corresponding wild-type NPP4 or fragment thereof. In yet other embodiments of the aspects recited herein, the mutant NPP4 polypeptide or fragment thereof comprises at least one mutation which decreases the Ap3A hydrolytic activity of the enzyme as compared to the corresponding wild-type NPP4 or fragment thereof. In yet other embodiments of the aspects recited herein, the mutant NPP4 polypeptide or fragment thereof comprises at least one mutation which substantially increases the ATP hydrolysis activity and decreases the Ap3A hydrolytic activity of the enzyme as compared to the corresponding wild-type NPP4 or fragment thereof. In yet other embodiments of the aspects recited herein, the NPP4 polypeptide or a fragment, mutant or mutant fragment thereof lacks the NPP4 transmembrane domain. In yet other embodiments of the aspects recited herein, the NPP4 polypeptide or a fragment, mutant or mutant fragment thereof comprises an IgG Fc domain.

In various embodiments of any of the above aspects or any other aspect of the invention delineated herein, the NPP4 polypeptide or a fragment, mutant or mutant fragment thereof comprises a polyaspartic acid domain. In certain embodiments of the aspects recited herein, the polyaspartic acid domain comprises from about 2 to about 20 or more sequential aspartic acid residues. In other embodiments of the aspects recited herein, the activator of NPP4 activates at least one selected from the group consisting of: expression of NPP4 polypeptide or a fragment, mutant or mutant fragment thereof; and activity of NPP4 polypeptide or a fragment, mutant or mutant fragment thereof. In yet other embodiments of the aspects recited herein, the activator of NPP4 is at least one selected from the group consisting of a chemical compound, a protein, a peptide, a peptidomimetic, and a small molecule chemical compound.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 2A: NPP1 is replaced with the signal peptide from NPP2 so it can be expressed as a secreted protein. The NPP1 fragments on either side of the transmembrane region (indicated by 1 and 2) are PCR amplified separately and substituted with the NPP2 signal peptide sequence (indicated by 3, by the arrow). FIG. 2B: Schematic figure of domain architecture and expressed proteins used in this study. NPP1 is a type II transmembrane protein, while NPP4 is a type I transmembrane protein. The proteins are represented by schematics colored to illustrate the domain architecture—transmembrane domains are indicated as 1, somatomedin B domains are indicated as 2, catalytic domains are indicated as 3, the nuclease domain is indicated as 4, and the signal peptide of NPP4 is indicated as 5. The expressed NPP1 protein consists of residues 96-925 of the human sequence, comprising the entire extracellular sequence of the protein, containing both somatomedin B domains, the catalytic domain, and the nuclease domain of the protein. The secreted NPP4 protein also consists of the entire extracellular portion of the protein, comprising amino acids 16-407 of the human sequence.

FIG. 5A is a graph depicting the HPLC analysis of ATP cleavage by NPP1 (nM NPP1 supplemented with 500 µM ATP quenched at (from bottom to top) 3, 6, and 30 minutes). The enzymatic products of ATP hydrolysis by NPP1 were confirmed by HPLC. FIG. 5B is a graph depicting the comparison of ATP hydrolysis between NPP1 and NPP4. The comparison of the ATP hydrolytic activity of NPP1 and NPP4 (which share 38% sequence identity) reveals that only NPP1 hydrolyzes ATP, revealing the tuned substrate specificity of the NPP family. FIG. 5C is a graph depicting the results of experiments assessing steady-state ATP cleavage by NPP1. Time courses of ATP cleavage monitored at absorbance 259 nm after mixing 200 nM of NPP1 were used to derive the initial rate velocities at each ATP concentration, and the data is fit to a rectangular hyperbola. The smooth line through the data is the best fit to a hyperbola, resulting in $K_M$=144.5 (±36.0) µM and $k_{cat}$=468 (±48) min$^{-1}$=7.8 (±0.8) s$^{-1}$. FIG. 5D: Ap3A concentration dependence of the NPP1 and NPP4 initial steady state Ap3A substrate cleavage rate obtained from the best linear fits of absorption change of time courses. The smooth lines though the data are the best fit to a hyperbola with $K_M$=20 (±3) µM and $k_{cat}$=7.2 (±0.3) s$^{-1}$ NPP$^{-1}$ for NPP1, while with $K_M$=685 (±108) µM and $k_{cat}$=8.0 (±0.1) s$^{-1}$ NPP$^{-1}$ for NPP4. FIG. 5E: Inhibition of NPP4 cleavage activity by nucleotide monophosphates. The solid line through the data points represent the best fit to a rectangular hyperbola. Symbols: AMP: magenta diamond, CMP: black square, GMP: blue circle. The resulting $IC_{50}$, from strongest to weakest inhibition, is AMP 129±73 µM, CMP 322±39 µM, UMP 2.11±0.37 mM (not shown for clarity), and GMP 2.98±0.38 mM.

FIG. 6A: The protein is displayed as a ribbon with AMP in stick form colored by atom type. Active site zinc ions are depicted as spheres. FIG. 6B: Superposition of Cα-traces of human NPP4 with other NPP catalytic domains reveals that the greatest degree of structural conservation to the left and to the right of the zinc ions (rmsd of 0.68 Å for all 4 molecules as shown) occurs throughout the central β-sheet core and the active site near the zinc ions, including the α-helix on which the catalytic threonine is located and the backbone near the hydrophobic slot. Regions of moderate similarity are shown in the light grey below the zinc ions (rmsd of 1.33 Å) and those of the lowest similarity are shown in light grey above the zinc ions (rmsd of 2.51 Å). The ccp4 program Superpose was used to overlay the conserved NPP catalytic domains and the regions of moderate similarity (rmsd of 1.17 Å). Despite the high degree of structural conservation near the active site, different NPPs can display widely varying substrate specificities. The four superposed catalytic domains are from human NPP4 (presented here), mouse NPP1 (4B56), mouse NPP2 (3NKN), and a bacterial NPP (2GSU). To accommodate a lipid substrate, NPP2 lacks a region found in all other NPP catalytic domains and therefore an 8-residue linker (residues 272 to 279) within mouse NPP2 was omitted in this comparison figure. Superposition of the entire catalytic domain of NPP4 with that of NPP1, NPP2 and the bacterial NPP yield rmsd values of 1.54 Å, 1.43 Å and 1.43 Å, respectively. FIG. 6C: NPP4 product complex with AMP. Omit mFo-DFc difference-density is shown for each, contoured at 3σ. Ligands and water molecules within the binding pocket were not included in the electron density map calculations. PyMOL was used to generate all molecular images (Molecular Graphics System, Version 1.2r3pre, Schrödinger, LLC).

FIG. 7A: The active site of NPP4 contains a pre-formed hydrophobic slot that results in its specificity for 5' nucleotide containing substrates. In the NPP4-AMP complex, the adenine ring stacks with Tyr154 on one wall of the pocket while receiving favorable VDW interactions from the tip of Phe71 along the opposite wall. To display the fit, the molecular surface of NPP4 (in mesh) and the VDW surface of AMP (in semi-transparent shape) are shown. FIG. 7B: Position of AMP in the active site with key residues and bound-metal ions highlighted. The two bound zinc ions (spheres) play different roles, with Zn2 serving to activate Thr70 for nucleophilic attack on the substrate, while Zn1 electrostatically draws a phosphate group of the substrate into close proximity. Tyr154 and Phe71 of the nucleotide slot are shown. FIG. 7C: Superposition of the NPP4-AMP complex with apo NPP4 to illustrate that there is very little change when product is bound. A citrate anion bound at Zn1 of the apo structure has been omitted for visual clarity. FIG. 7D: Superposition of NPP4-AMP and NPP1-AMP complexes to illustrate the similar geometry within this half of their active sites, with both possessing a slot for nucleotide binding.

FIGS. 9A-9F illustrate a non-limiting modeling of the molecular basis of substrate discrimination of NPP1 and NPP4. Models of ATP bound in an AMP-like orientation are shown for NPP1 (left column) and NPP4 (right column), based on the AMP cocrystal structures for each enzyme. FIG. 9A: In NPP1, the γ-phosphate of ATP is simultaneously stabilized by three lysine residues, two of which line the upper edge of the pocket and become ordered only when substrate is present due to electrostatics. As a result of this tri-partite lysine claw, the γ-phosphate of bound ATP is favorably charge-stabilized and largely shielded from solvent by an induced-fit lid comprised of the long hydrophobic side chains of these two lysines along with an adjacent tyrosine ring. In contrast, NPP4 offers a significantly less favorable γ-phosphate environment for a similarly bound ATP, with less charge-stabilization, a more open architecture with no lid mechanism, and two nearby aspartate residues for charge-repulsion. As a result, ATP is not likely to bind in this orientation to NPP4 very often. FIGS. 9A & 9B: Stick figures of ATP bound as modeled from AMP cocrystal structures. FIGS. 9C & 9D: Same, but as a molecular surface with tips of nearby charged side chains (positive or negative, as indicated). FIGS. 9E & 9F: Rotated about 90 degrees. Sequence alignments show that human NPP1 retains all of the features derived from the mouse NPP1 structure.

FIG. 10A: In the absence of NPP1, 80 µM Ap3A elicited only a primary wave of aggregation followed by rapid disaggregation, and this pattern was similarly observed with the addition of NPP1 in concentrations of 300 pM and 500 pM. In contrast, 1 nM NPP1 in the presence of 80 uM Ap3A stimulated a measurable secondary wave of aggregation. FIG. 10B: NPP4 exhibited primary aggregation in the presence of either Ap3A alone or Ap3A containing 1 nM NPP4. In the presence of 20 nM NPP4 and higher there was marked secondary platelet aggregation. The findings suggest that either protein may directly stimulates platelet aggregation at low nM concentrations in the presence of physiologic concentrations of Ap3A.

DETAILED DESCRIPTION OF THE INVENTION

Figure 1:
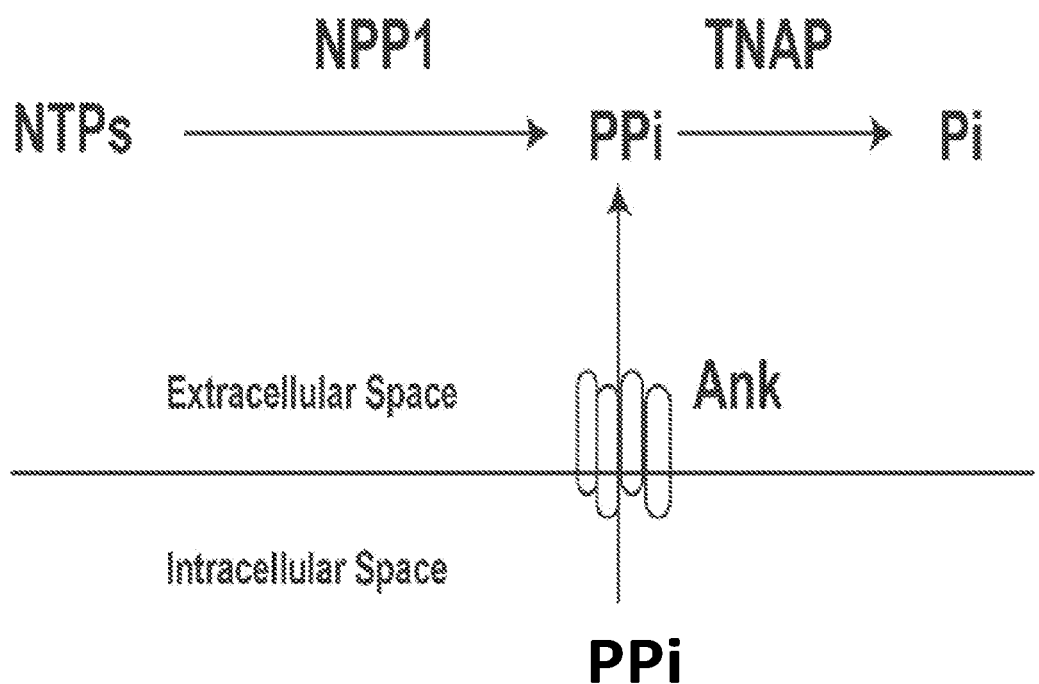
FIG. 1 is an illustration depicting proteins regulating the extracellular balance of inorganic pyrophosphate (PPi) and phosphate (Pi). Inorganic pyrophosphate (PPi) is generated by the cleavage of extracellular nucleotide triphosphates (NTPs) by NPP1 or the transfer of PPi from the intracellular to extracellular space by Ank. TNAP degrades PPi to generate Pi.

The present invention relates to the discovery that an NPP1 polypeptide, fragment, derivative, mutant, or mutant fragment thereof, and a mutant NPP4 polypeptide or fragment thereof, are useful for the treatment of diseases and disorders involving pathological calcification and/or ossification.

Thus, in certain embodiments, the invention relates to compositions and methods for increasing the level or activity of an NPP1 polypeptide, fragment, derivative, mutant, or mutant fragment thereof, while in other embodiments the invention relates to compositions and methods for increasing the level or activity of a mutant NPP4 polypeptide, fragment, or derivative thereof. In yet other embodiments, the invention relates to compositions and methods for increasing the level or activity of an NPP1 polypeptide, fragment, derivative, mutant, or mutant fragment thereof, and a mutant NPP4 polypeptide or fragment thereof.

In certain embodiments, the invention relates to a method of eliminating and/or reducing the pro-thrombotic activity, while retaining the ATP hydrolytic activity, of at least one agent selected from the group consisting of an ecto-nucleotide pyrophosphate/phosphodiesterase-1 (NPP1) polypeptide and a fragment, derivative, mutant or mutant fragment thereof. In other embodiments, the invention relates to a method of eliminating and/or reducing the pro-thrombotic activity, while also increasing the ATP hydrolytic activity, of at least one agent selected from the group consisting of an ecto-nucleotide pyrophosphate/phosphodiesterase-1 (NPP4) polypeptide and a fragment, derivative, mutant or mutant fragment thereof. In yet other embodiments, the methods of the invention allow for safely treating ectopic mineralization without inducing unintended risks associated with a pro-thrombotic state.

In various embodiments, the mutant NPP1 polypeptide, fragment or derivative thereof useful within the methods of the invention has lower Ap3A hydrolytic activity as compared to the corresponding wild-type NPP1 polypeptide, fragment or derivative thereof. In various embodiments, the mutant NPP1 polypeptide, fragment or derivative thereof useful within the methods of the invention has substantially the same ATP hydrolytic activity as compared to the corresponding wild-type NPP1 polypeptide, fragment or derivative thereof. In various embodiments, the mutant NPP1 polypeptide, fragment or derivative thereof useful within the methods of the invention has lower Ap3A hydrolytic activity and substantially the same ATP hydrolytic activity as compared to the corresponding wild-type NPP1 polypeptide, fragment or derivative thereof.

In various embodiments, the invention relates to compositions and methods for increasing the level or activity of NPP1 polypeptide, fragment, derivative, mutant, or mutant fragment thereof. The compositions and methods of the invention include compositions and methods for treating or preventing disorders and diseases where an increased activity or level of NPP1 polypeptide, fragment, derivative, mutant, or mutant fragment thereof is desirable. In various embodiments, the disorders and diseases include diseases and disorders involving pathological calcification and/or pathological ossification. Diseases and disorders involving pathological calcification and/or pathological ossification treatable by the compositions and methods of the invention, include, but are not limited to idiopathic infantile arterial calcification (IIAC), ossification of the posterior longitudinal ligament (OPLL), hypophosphatemic rickets, osteoarthritis, and the calcification of atherosclerotic plaques.

In other embodiments, the invention relates to compositions and methods for increasing the level or activity of mutant NPP4 polypeptide or fragment thereof. The compositions and methods of the invention include compositions and methods for treating or preventing disorders and diseases where an increased activity or level of mutant NPP4 polypeptide or fragment thereof is desirable. In various embodiments, the disorders and diseases include diseases and disorders involving pathological calcification and/or pathological ossification. Diseases and disorders involving pathological calcification and/or pathological ossification treatable by the compositions and methods of the invention, include, but are not limited to Idiopathic Infantile Arterial Calcification (IIAC), Ossification of the Posterior Longitudinal Ligament (OPLL), hypophosphatemic rickets, osteoarthritis, and calcification of atherosclerotic plaques.

Both hemostasis and bone development are essential, finely balanced physiologic processes that are regulated by the extracellular metabolism of purinergic signals. As described herein, to better understand the role and atomic details of purinergic signal metabolism by NPP1 and NPP4, the high-resolution structure of NPP4, the first human NPP to be solved, was determined as a way to characterize NPP4 versus NPP1 structurally and enzymatically. NPP1 was shown to hydrolyze Ap3A at low nM concentrations, and either NPP1 or NPP4 in low nM concentrations promoted irreversible platelet aggregation in human PRP in vitro.

In addition, the effect of NPP1 on platelet aggregation in the presence of physiologic levels of Ap3A was directly measured. Despite the high degree of sequence identity and homology, and shared structural features that allow for the targeting of a mostly similar set of nucleotide-containing substrates, these two enzymes also possess key structural differences that account for the distinct substrate specificities central to their biological functions. NPP1 was found to be unable to induce platelet aggregation at physiologic concentrations reported in human blood, but could stimulate platelet aggregation if localized at low nM concentrations on vascular endothelium. The present studies describe the molecular basis of substrate discrimination by NPP4 and NPP1, provide insight into their physiologic roles governing bone mineralization and platelet aggregation, and provide an apparent mechanism by which NPP1 polymorphisms associated with stroke protection may act.

Without wishing to be limited by any theory, the present studies suggest an alternate mechanism by which polymorphisms in NPP1 are protective against thrombotic stroke, as compared to the mechanism proposed in the prior art. The data described herein support the notion that loss of function mutations, wherein Ap3A hydrolysis is decreased in the thrombotic microenvironment, and not gain of function mutations as proposed in the prior art, contribute to the mechanism by which these polymorphisms confer stroke protection. This distinction plays an important role in designing alterations in the NPP1 and NPP4 protein that are useful as therapeutic agents against ectopic bone mineralization without inducing unintended side effects of a pro-thrombotic state in the treated individuals. In certain embodiments, decreased NPP1 activity in brain capillaries result in decreased ADP concentrations in the cerebral capillary bed, decreasing platelet aggregation and thrombus formation.

Further, the recognition of NPP1 as a pro-thrombotic enzyme suggests that recombinant enzyme replacement therapy with NPP1 or NPP4 confers significant thrombotic risk to patients treated with recombinant NPP1 and/or NPP4 enzymes. Patients in a pro-thrombotic state are at risk for sudden death due to coronary artery and/or pulmonary artery thrombosis, and to stroke due to cerebral artery thrombosis. As demonstrated herein, the inventors have established the biochemical and physiologic rationale to support the notion that patients treated with recombinant, unmodified NPP1 enzyme would be at elevated risk for these unintended effects. The recognition by the inventors of NPP1's role in thrombosis establishes the rationale for inducing specific point mutations in NPP1 and/or NPP4 that eliminate and/or ameliorate the pro-thrombotic activity of the enzyme, while retaining the ability of the enzyme to generate PPi. In certain embodiments, specific modification in NPP1 and NPP4 as proposed herein accomplish the goal of establishing a safe therapeutic for the treatment of GACI and other diseases of ectopic mineralization through the use of recombinant NPP4 and NPP1 enzyme.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "Ap3P" refers to adenosine-(5')-triphospho-(5')-adenosine or a salt thereof.

As used herein, the term "NPP" refers to ectonucleotide pyrophosphatase/phosphodiesterase.

A "disease" is a state of health of an animal wherein the animal cannot maintain homeostasis, and wherein if the disease is not ameliorated then the animal's health continues to deteriorate.

A "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

"Isolated" means altered or removed from the natural state. For example, a nucleic acid or a polypeptide naturally present in a living animal is not "isolated," but the same nucleic acid or polypeptide partially or completely separated from the coexisting materials of its natural state is "isolated." An isolated nucleic acid or protein can exist in substantially purified form, or can exist in a non-native environment such as, for example, a host cell.

As used herein, "substantially purified" refers to being essentially free of other components. For example, a substantially purified polypeptide is a polypeptide which has been separated from other components with which it is normally associated in its naturally occurring state.

"Sample" or "biological sample" as used herein means a biological material isolated from a subject. The biological sample may contain any biological material suitable for detecting a mRNA, polypeptide or other marker of a physiologic or pathologic process in a subject, and may comprise fluid, tissue, cellular and/or non-cellular material obtained from the individual.

As used herein, the term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and/or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the term "polypeptide" refers to a polymer composed of amino acid residues, related naturally occurring structural variants, and synthetic non-naturally occurring analogs thereof linked via peptide bonds. Synthetic polypeptides may be synthesized, for example, using an automated polypeptide synthesizer. As used herein, the term "protein" typically refers to large polypeptides. As used herein, the term "peptide" typically refers to short polypeptides. Conventional notation is used herein to represent polypeptide sequences: the left-hand end of a polypeptide sequence is the amino-terminus, and the right-hand end of a polypeptide sequence is the carboxyl-terminus.

As used herein, amino acids are represented by the full name thereof, by the three letter code corresponding thereto, or by the one-letter code corresponding thereto, as indicated below:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The term "amino acid sequence variant" refers to polypeptides having amino acid sequences that differ to some extent from a native sequence polypeptide. Ordinarily, amino acid sequence variants possess at least about 70% homology, at least about 80% homology, at least about 90% homology, or at least about 95% homology to the native polypeptide. The amino acid sequence variants possess substitutions, deletions, and/or insertions at certain positions within the amino acid sequence of the native amino acid sequence.

As used herein, the terms "conservative variation" or "conservative substitution" as used herein refers to the replacement of an amino acid residue by another, biologically similar residue. Conservative variations or substitutions are not likely to change the shape of the peptide chain. Examples of conservative variations, or substitutions, include the replacement of one hydrophobic residue such as isoleucine, valine, leucine or methionine for another, or the substitution of one polar residue for another, such as the substitution of arginine for lysine, glutamic for aspartic acid, or glutamine for asparagine.

As used herein, the term "domain" refers to a part of a molecule or structure that shares common physicochemical features, such as, but not limited to, hydrophobic, polar, globular and helical domains or properties. Specific examples of binding domains include, but are not limited to, DNA binding domains and ATP binding domains.

A "nucleic acid" refers to a polynucleotide and includes poly-ribonucleotides and poly-deoxyribonucleotides. Nucleic acids according to the present invention may include any polymer or oligomer of pyrimidine and purine bases, preferably cytosine, thymine, and uracil, and adenine and guanine, respectively. (See Albert L. Lehninger, Principles of Biochemistry, at 793-800 (Worth Pub. 1982) which is herein incorporated in its entirety for all purposes). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferably at least 8, 15 or 25 nucleotides in length, but may be up to 50, 100, 1000, or 5000 nucleotides long or a compound that specifically hybridizes to a polynucleotide. Polynucleotides include sequences of deoxyribonucleic acid (DNA) or ribonucleic acid (RNA) or mimetics thereof which may be isolated from natural sources, recombinantly produced or artificially synthesized. A further example of a polynucleotide of the present invention may be a peptide nucleic acid (PNA). (See U.S. Pat. No. 6,156,501 which is hereby incorporated by reference in its entirety) The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably herein. It is understood that when a nucleotide sequence is represented herein by a DNA sequence (e.g., A, T, G, and C), this also includes the corresponding RNA sequence (e.g., A, U, G, C) in which "U" replaces "T."

As used herein, "polynucleotide" includes cDNA, RNA, DNA/RNA hybrid, antisense RNA, ribozyme, genomic DNA, synthetic forms, and mixed polymers, both sense and antisense strands, and may be chemically or biochemically modified to contain non-natural or derivatized, synthetic, or semi-synthetic nucleotide bases. Also, contemplated are alterations of a wild type or synthetic gene, including but not limited to deletion, insertion, substitution of one or more nucleotides, or fusion to other polynucleotide sequences.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

An "allele" refers to one specific form of a genetic sequence (such as a gene) within a cell, an individual or within a population, the specific form differing from other forms of the same gene in the sequence of at least one, and frequently more than one, variant sites within the sequence of the gene. The sequences at these variant sites that differ between different alleles are termed "variants," "polymorphisms," or "mutations."

As used herein the terms "alteration," "defect," "variation" or "mutation" refer to a mutation in a gene in a cell that affects the function, activity, expression (transcription or translation) or conformation of the polypeptide it encodes. Mutations encompassed by the present invention can be any mutation of a gene in a cell that results in the enhancement or disruption of the function, activity, expression or conformation of the encoded polypeptide, including the complete absence of expression of the encoded protein and can include, for example, missense and nonsense mutations, insertions, deletions, frameshifts and premature terminations. Without being so limited, mutations encompassed by the present invention may alter splicing the mRNA (splice site mutation) or cause a shift in the reading frame (frameshift).

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab and F(ab)2, as well as single chain antibodies (scFv), heavy chain antibodies, such as camelid antibodies, synthetic antibodies, chimeric antibodies, and a humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

As used herein, an "immunoassay" refers to any binding assay that uses an antibody capable of binding specifically to a target molecule to detect and quantify the target molecule.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The term "coding sequence," as used herein, means a sequence of a nucleic acid or its complement, or a part thereof, that can be transcribed and/or translated to produce the mRNA and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the coding sequence can be deduced therefrom. In contrast, the term "non-coding sequence," as used herein, means a sequence of a nucleic acid or its complement, or a part thereof, that is not translated into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, and the like.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides; at least about 1000 nucleotides to about 1500 nucleotides; about 1500 nucleotides to about 2500 nucleotides; or about 2500 nucleotides (and any integer value in between). As used herein, the term "fragment," as applied to a protein or peptide, refers to a subsequence of a larger protein or peptide. A "fragment" of a protein or peptide can be at least about 20 amino acids in length; for example, at least about 50 amino acids in length; at least about 100 amino acids in length; at least about 200 amino acids in length; at least about 300 amino acids in length; or at least about 400 amino acids in length (and any integer value in between).

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared X 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

"Instructional material," as that term is used herein, includes a publication, a recording, a diagram, or any other medium of expression which can be used to communicate the usefulness of the nucleic acid, peptide, and/or compound of the invention in the kit for identifying or alleviating or treating the various diseases or disorders recited herein. Optionally, or alternately, the instructional material may describe one or more methods of identifying or alleviating the diseases or disorders in a cell or a tissue of a subject. The instructional material of the kit may, for example, be affixed to a container that contains the nucleic acid, polypeptide, and/or compound of the invention or be shipped together with a container that contains the nucleic acid, polypeptide, and/or compound. Alternatively, the instructional material may be shipped separately from the container with the intention that the recipient uses the instructional material and the compound cooperatively.

By the term "modulating," as used herein, is meant mediating a detectable increase or decrease in the activity and/or level of a mRNA, polypeptide, or a response in a subject compared with the activity and/or level of a mRNA, polypeptide or a response in the subject in the absence of a treatment or compound, and/or compared with the activity and/or level of a mRNA, polypeptide, or a response in an otherwise identical but untreated subject. The term encompasses activating, inhibiting and/or otherwise affecting a native signal or response thereby mediating a beneficial therapeutic response in a subject, preferably, a human.

As used herein, the term "treatment" or "treating" is defined as the application or administration of a therapeutic agent, i.e., a compound useful within the invention (alone or in combination with another pharmaceutical agent), to a patient, or application or administration of a therapeutic agent to an isolated tissue or cell line from a patient (e.g., for diagnosis or ex vivo applications), who has a disease or disorder, a symptom of a disease or disorder or the potential to develop a disease or disorder, with the purpose to cure, heal, alleviate, relieve, alter, remedy, ameliorate, improve or affect the disease or disorder, the symptoms of the disease or disorder, or the potential to develop the disease or disorder. Such treatments may be specifically tailored or modified, based on knowledge obtained from the field of pharmacogenomics.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, individual or subject is human.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof. Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

As used herein, the term "composition" or "pharmaceutical composition" refers to a mixture of at least one compound useful within the invention with a pharmaceutically acceptable carrier. The pharmaceutical composition facilitates administration of the compound to a patient. Multiple techniques of administering a compound exist in the art including, but not limited to, intravenous, oral, aerosol, inhalational, rectal, vaginal, transdermal, intranasal, buccal, sublingual, parenteral, intrathecal, intragastrical, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present high-resolution structure determination of human NPP4 allowed for detailed comparative structure-function studies with NPP1. These membrane-bound cell surface enzymes are involved in the metabolism of extracellular purinergic signals as well as nucleotide re-uptake. Both ectoenzymes possess a narrow hydrophobic slot adjacent to two bound zinc ions that accounts for the targeting of nucleotide-containing substrates, where the nucleotide base binds within the slot and hydrolysis yields the nucleotide monophosphate as one of the products. Adenine is the most-preferred base type for both enzymes and cocrystal structures of each with a product AMP molecule bound highlight their functional similarity in that region of the binding site. Both enzymes were found to be able to hydrolyze Ap3A, but exhibit surprisingly different responses to ATP.

NPP4 and NPP1 differ drastically in their response to ATP. NPP1 readily hydrolyzes ATP to AMP and PPi, the latter of which is a potent inhibitor of extra-osseous mineralization, and mutants of NPP1 may be involved in diseases involving bone or soft-tissue calcification outlined earlier. To yield the observed products, ATP should bind NPP1 in the same orientation seen in the NPP1-AMP cocrystal structure. In stark contrast, NPP4 cleaves ATP only exceedingly slowly, even though it binds AMP in a manner very similar to NPP1. Superposition of the two enzymes reveals key structural differences in the area of the terminal phosphate of ATP, if bound like AMP. The energy minimized simulations of ATP-complexes reveal that NPP1 provides a favorable environment for the γ-phosphate of ATP via the presence of a tri-partite lysine claw that provides induced-fit charge-stabilization. In the absence of substrate, two lysines lining the upper ridge of the binding pocket (Lys260 and Lys510, mouse numbering) are mobile, as is demonstrated in the NPP1-AMP product-complex (4GTW) where they are disordered, or in the NPP1-vanadate complex (4B56) where they exhibit high B-factors and extend into the solvent. Upon ATP substrate binding, the highly-negative γ-phosphate should electrostatically attract these lysines, which along with the stationary Lys237 on the floor of the binding pocket should serve to effectively envelop the terminal-phosphate in positive-charge. This may also promote the hydrolysis via product-stabilization, since PPi is even more negatively-charged. The role that these lysine residues play in NPP1 hydrolysis of ATP had not been previously appreciated and came to light during the detailed structural comparisons with NPP4.

Superposition of the corresponding region of NPP4 shows it to be notably less favorable for a similarly-bound ATP, with a local architecture that is more open, contains fewer positively-charged residues and introduces negatively-charged residues such as Asp335, which projects into the active site in close proximity to the γ-phosphate of ATP. Cocrystallization attempts with a non-cleavable ATP-analogue revealed no visible binding, consistent with the observation that NPP4 provides an unfavorable environment in the region of the γ-phosphate. Similarly, cocrystallization attempts with ATP or a cleavable ATP-analogue yield an AMP-complex over the several days it takes for crystals to grow, indicating that although ATP binding is weak, it occasionally comes into close enough proximity to be hydrolyzed. AMP product molecule is able to bind under identical conditions, reflecting a stronger affinity. Product-inhibition is likely an intrinsic feature of NPP reactions since the phosphate group next to Zn1 gets converted, by definition, from a phosphodiester to a terminal phosphate that carries more negative-charge. The present data indicate that NPP4 is unlikely to hydrolyze ATP effectively in vivo, supporting the view that NPP1 is the primary extracellular enzyme metabolizing purinergic signals regulating bone remodeling and extracellular calcification.

Figure 10A:
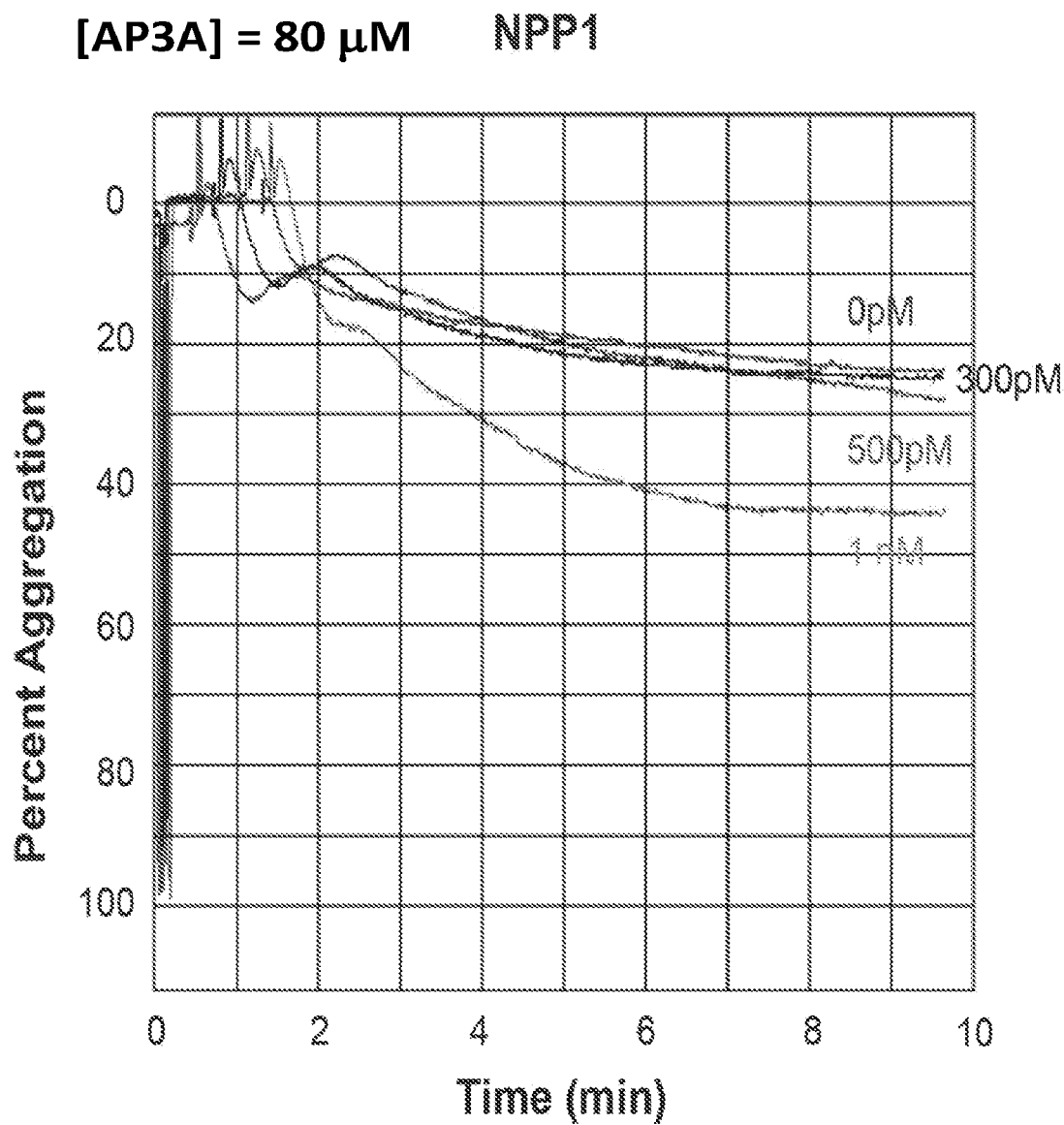
FIGS. 10A-10B are a series of graph illustrating the effect of NPP1 in platelet aggregation. Light transmission aggregometry was used to assess platelet aggregation in response to increasing concentrations of NPP1 and NPP4 and 80 µM Ap3A in platelet rich plasma. Data are shown graphically as percent of light transmittance (y-axis) over time (x-axis).
Figure 10B:
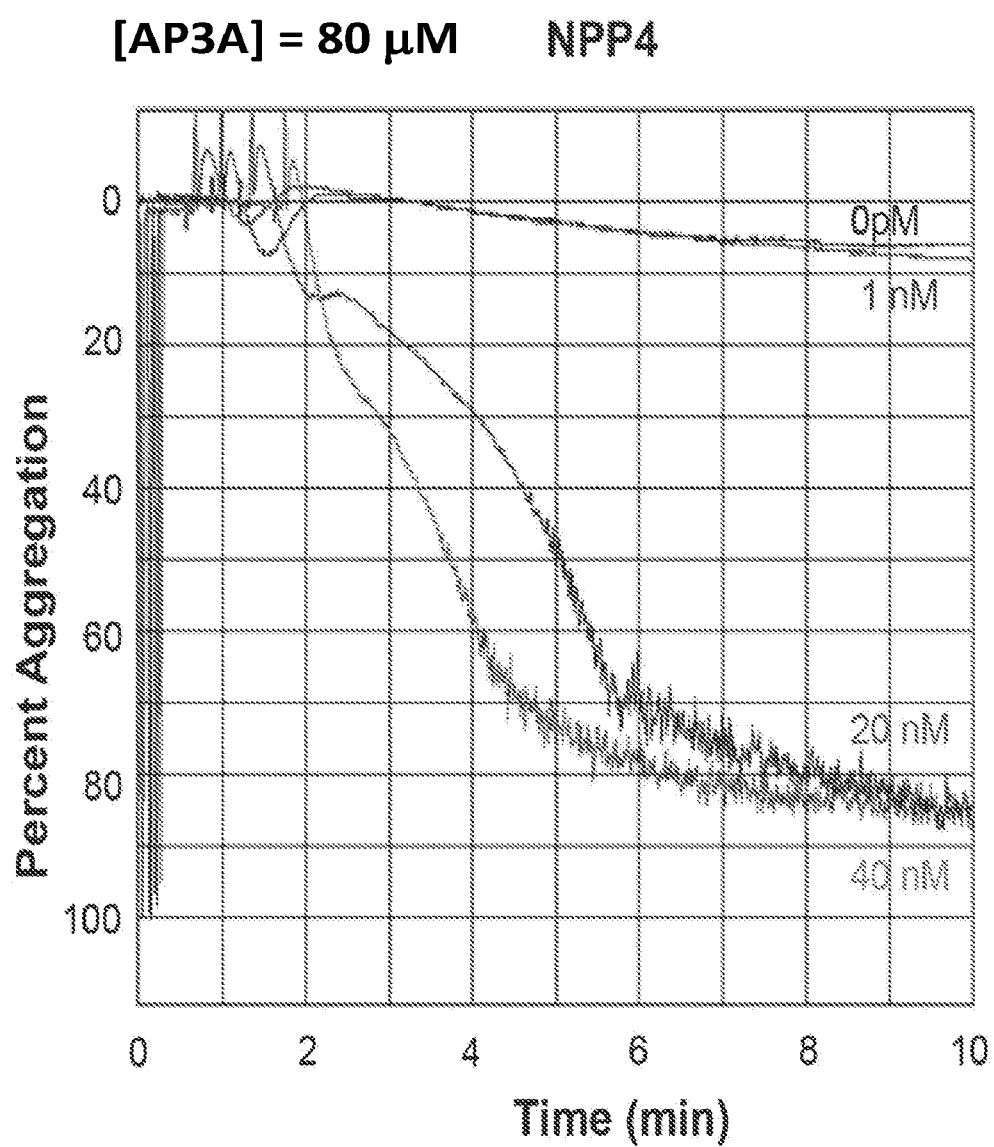
Figure 11:
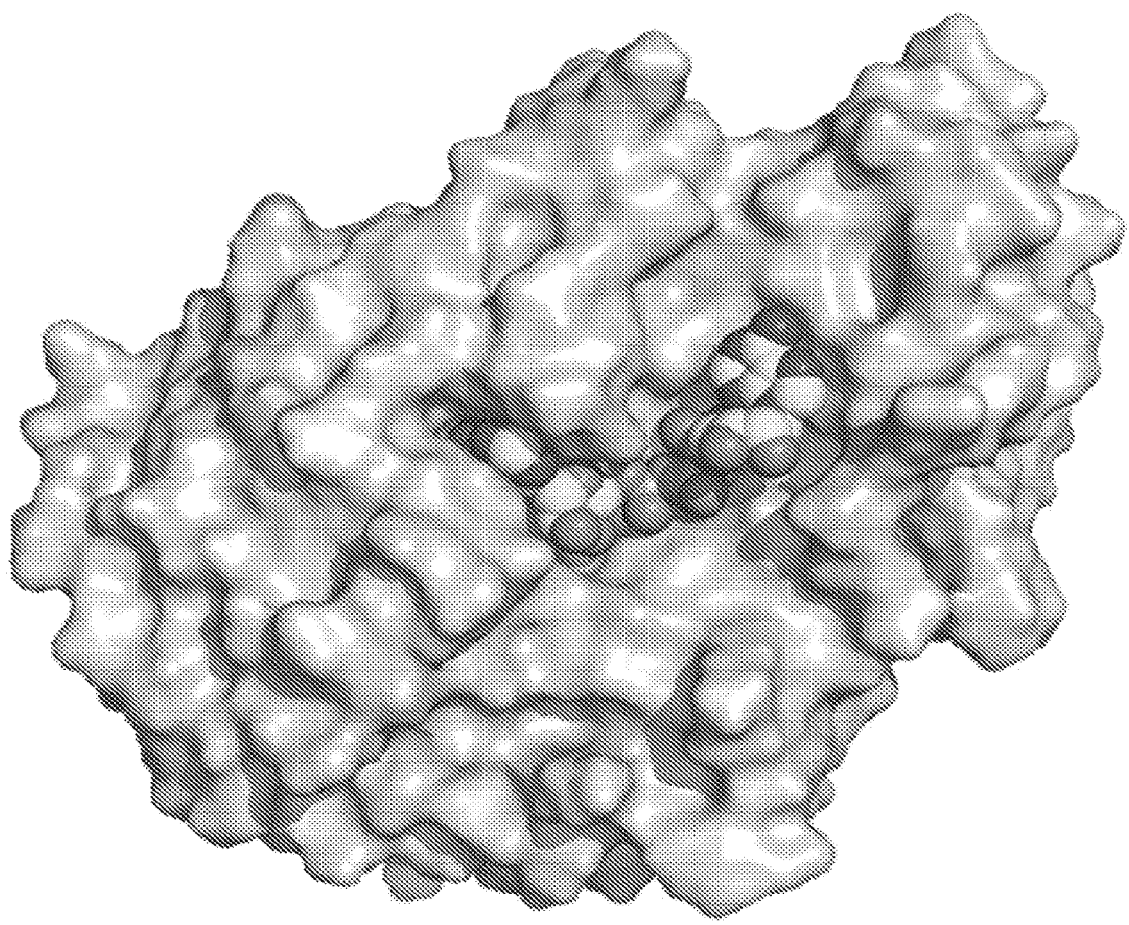
FIG. 11 is an illustrative model of Ap3A docketed into human NPP4.

In contrast, both NPP4 and NPP1 hydrolyze Ap3A into AMP and ADP, with the Michaelis constant of NPP1 for Ap3A some 30 fold tighter than that of NPP4. This higher affinity is reflected in the lower concentrations of NPP1 required to trigger platelet aggregation in identical concentrations of Ap3A (FIGS. 10A-10B). High concentrations of Ap3A stored in the dense granules of circulating platelets are released upon platelet activation. Without wishing to be limited by any theory, vascular bound NPPs may contribute to cerebral platelet aggregation by identifying NPP4 on brain vascular endothelium capable of inducing platelet aggregation via the hydrolysis of physiologic concentrations of Ap3A. Ap3A has a significantly longer lifespan in whole blood than ADP and has long been hypothesized to aid stable thrombus formation by serving as a 'chemically masked' source of ADP.

The ability of NPP1 to readily hydrolyze Ap3A to ADP raises the question of whether NPP1 may play a role in hemostasis. In the present study, NPP1 was shown to be capable of Ap3A hydrolysis at low nM concentrations, and either NPP1 or NPP4 in low nM concentrations promotes irreversible platelet aggregation in human PRP in vitro. The work implies that either enzyme may contribute significantly to platelet aggregation in vivo if present at low nM concentrations in a pro-thrombotic environment.

Recently, polymorphisms in NPP1 have been identified that confer stroke protection in pediatric patients with sickle cell anemia. The present results suggest that polymorphisms in NPP1 protective against stroke represent a loss of function mutation that decreases Ap3A hydrolysis in the thrombotic microenvironment. Decreased NPP1 activity in brain capillaries would result in decreased ADP concentrations in the cerebral capillary bed, thus providing a direct mechanism to account for decreased platelet aggregation and thrombus formation.

Figure 2A:
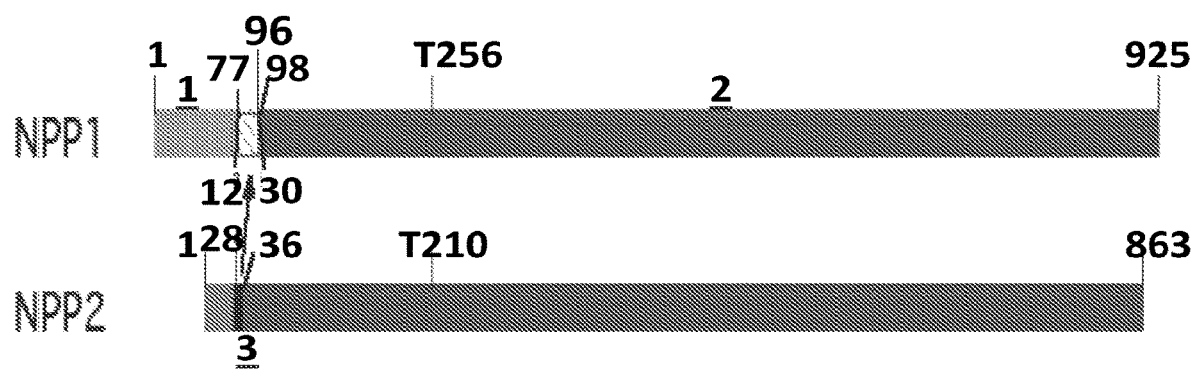
FIGS. 2A-2B are a set of illustrations depicting the cloning strategy of NPP1.
Figure 2B:
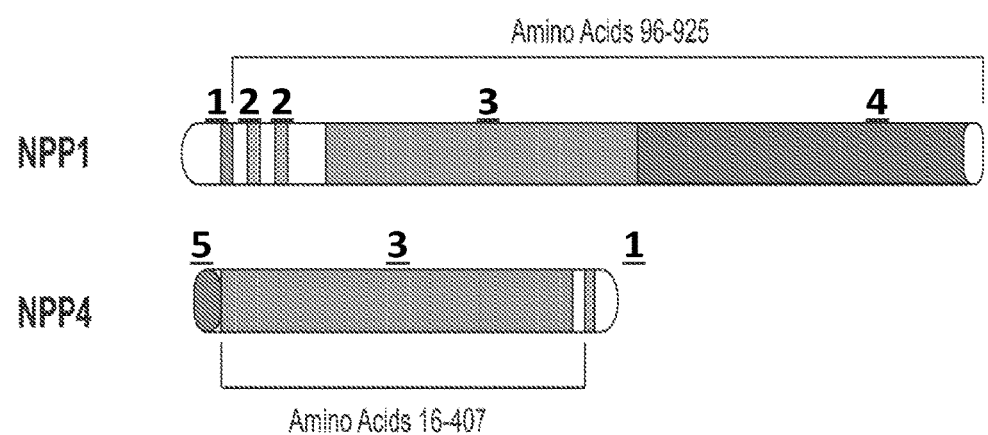

The K173Q mutation in human NPP1 is not in the catalytic domain, but rather is found in the somatomedin B-2 domain near the membrane spanning region (FIG. 2B). Loss of function mutations within the NPP1 catalytic domain are not compatible with human survival beyond the neonatal period, consistent with their absence in the population screened for stroke protection. Without wishing to be limited by any theory, while NPP1 K173Q mutations may increase NPP1 serum concentrations similarly to K121Q mutations observed in IDDM-2, the hypothesis of NPP1 gain of function is not supported by these serum increases, especially when viewed in light of the kinetic and aggregometry data. NPP1 serum concentrations in the K121Q polymorphism (28 pM) are well below those required for NPP1-induced activation of platelet aggregation in vitro, and the Michaelis constant of NPP1 for both ATP and Ap3A is nearly $10^6$ higher than the 4 pM increase induced by the K121Q polymorphism, suggesting that the increase is unlikely to impact either systemic PPi or ADP concentrations. Without wishing to be bound by any particular theory, a possible mechanism for changes attributed to the NPP1 K173Q polymorphism could be increased ectodomain shedding of NPP1 from vascular endothelium, which would account for both increases in serum levels and the loss of NPP1 activity on vascular endothelium now denuded of the protein. In summation, although the means by which a K173Q mutation impairs NPP1 catalytic activity remains obscure, the present findings support the notion that NPP1 polymorphisms protective against stroke are more likely to represent loss function mutations that decrease Ap3A hydrolysis on the endothelial surface of cerebral capillary beds, than gain of function mutations which increase PPi concentrations.

In some embodiments, the invention relates to compositions and methods for increasing the ATP hydrolytic level or activity of NPP1 polypeptide, fragment, derivative, mutant, or mutant fragment thereof. In other embodiments, the invention relates to compositions and methods inducing and increasing the ATP hydrolytic level or activity of mutant NPP4 polypeptide or fragment thereof.

In some embodiments, the invention relates to compositions and methods for decreasing the Ap3A hydrolytic level or activity of NPP1 polypeptide, fragment, derivative, mutant, or mutant fragment thereof. In other embodiments, the invention relates to compositions and methods for decreasing the Ap3A hydrolytic level or activity of mutant NPP4 polypeptide or fragment thereof.

The methods of the invention include methods of treating or preventing disorders and diseases where an increased activity or level of NPP1 polypeptide, fragment, derivative, mutant, or mutant fragment thereof is desirable. Thus, in some embodiments, the compositions of the invention relate to activators of NPP1 polypeptide, fragment, derivative, mutant, or mutant fragment thereof. In various embodiments, the disorders and diseases include, but are not limited to IIAC, OPLL, hypophosphatemic rickets, osteoarthritis, and the calcification of atherosclerotic plaques.

In various embodiments, the mutant NPP1 polypeptide or fragment thereof useful within the methods of the invention has lower Ap3A hydrolytic activity as compared to the corresponding wild-type NPP1 polypeptide or fragment thereof. In various embodiments, the mutant NPP1 polypeptide or fragment thereof useful within the methods of the invention has substantially the same ATP hydrolytic activity as compared to the corresponding wild-type NPP1 polypeptide or fragment thereof. In various embodiments, the mutant NPP1 polypeptide or fragment thereof useful within the methods of the invention has lower Ap3A hydrolytic activity and substantially the same ATP hydrolytic activity as compared to the corresponding wild-type NPP1 polypeptide or fragment thereof.

In other embodiments, the methods of the invention include methods of treating or preventing disorders and diseases where an increased activity or level of mutant NPP4 polypeptide or fragment thereof is desirable. Thus, in some embodiments, the compositions of the invention relate to activators of mutant NPP4 polypeptide or fragment thereof. In various embodiments, the disorders and diseases include, but are not limited to IIAC, OPLL, hypophosphatemic rickets, osteoarthritis, and calcification of atherosclerotic plaques. In some embodiments, the invention relates to compositions and methods for altering the enzymatic activity of mutant NPP4 polypeptide or fragment thereof into a hydrolase, or an enzyme with the same enzymatic activity of NPP1 polypeptide, fragment, derivative, mutant, or mutant fragment thereof.

In various embodiments, the mutant NPP4 polypeptide or fragment thereof useful within the methods of the invention has lower Ap3A hydrolytic activity as compared to the corresponding wild-type NPP4 polypeptide or fragment thereof. In other embodiments, the mutant NPP4 polypeptide or fragment thereof useful within the methods of the invention has substantially increased ATP hydrolytic activity as compared to the corresponding wild-type NPP4 polypeptide or fragment thereof. In yet other embodiments, the mutant NPP4 polypeptide or fragment thereof useful within the methods of the invention has lower Ap3A hydrolytic activity and substantially increased ATP hydrolytic activity as compared to the corresponding wild-type NPP4 polypeptide or fragment thereof.

In further embodiments, the invention relates to compositions and methods for increasing the level or activity of NPP1 polypeptide, fragment, derivative, mutant, or mutant fragment thereof, and mutant NPP4 polypeptide or fragment thereof.

NPP1 Therapeutic Activator Compositions and Methods

The present invention includes NPP1 activator compositions and methods of increasing the level or activity of NPP1 or a mutant thereof. In various embodiments, the NPP1 activator compositions and methods of treatment of the invention increase the amount of NPP1 polypeptide, NPP1 mRNA, NPP1 enzymatic activity, NPP1 substrate binding activity, a mutant thereof or a combination thereof. In various embodiments, the diseases and disorders where a decrease in pathological calcification or ossification may improve therapeutic outcome include, but are not limited to, IIAC, OPLL, hypophosphatemic rickets, osteoarthritis, and calcification of atherosclerotic plaques.

In various embodiments, the mutant NPP1 useful within the methods of the invention has lower Ap3A hydrolytic activity as compared to the corresponding wild-type NPP1. In various embodiments, the mutant NPP1 useful within the methods of the invention has substantially the same ATP hydrolytic activity as compared to the corresponding wild-type NPP1. In various embodiments, the mutant NPP1 useful within the methods of the invention has lower Ap3A hydrolytic activity and substantially the same ATP hydrolytic activity as compared to the corresponding wild-type NPP1. In various embodiments, the mutant NPP1 has a mutation in at least one position selected from the group consisting of Ser 532, Tyr 529, Tyr 451, Ile 450, Ser 381, Tyr 382, Ser 377, Phe 346, Gly 531, Ser 289, Ser 287, Ala 454, Gly 452, Gln 519, Glu 526, Lys 448, Glu 508, Arg 456, Asp 276, Tyr 434, Gln 519, Ser 525, Gly 342, Ser 343 and Gly 536. Without wishing to be limited by any theory, the mutations contemplated within the invention are informed by the high-resolution structure determination of NPP4 by the inventors, and the correct interpretation of the lysine claw in NPP1 that facilitates ATP hydrolysis by NPP1 (FIGS. 6A-6C, 7A-7D, 7, 9A-9F).

It will be understood by one skilled in the art, based upon the disclosure provided herein, that an increase in the level of NPP1 or mutant thereof encompasses the increase in expression, including transcription, translation, or both, of NPP1 or mutant thereof. The skilled artisan will also appreciate, once armed with the teachings of the present invention, that an increase in the level of NPP1 or mutant thereof includes an increase in activity (e.g., enzymatic activity, substrate binding activity, etc.) of NPP1 or mutant thereof. Thus, increasing the level or activity of NPP1 or mutant thereof includes, but is not limited to, increasing the amount of NPP1 polypeptide or mutant thereof, and increasing transcription, translation, or both, of a nucleic acid encoding NPP1 or mutant thereof; and it also includes increasing any activity of an NPP1 polypeptide or mutant thereof as well. The compositions and methods of the invention can selectively activate NPP1 or mutant thereof, or can activate both NPP1 or mutant thereof and another molecule, such as, by way of a non-limiting example, mutant NPP4.

It will be understood by one skilled in the art, based upon the disclosure provided herein, including the three-dimensional structure reported herein, that an increase in the level of NPP1 activity or mutant thereof encompasses the manipulation of specific residues in NPP1 to effect alterations of the Michaelis-Menton constants to either increase the affinity of the enzyme for ATP ($K_m$) or to increase the turnover rate of ATP into $PP_i$ by NPP1 ($k_{cat}$). The skilled artisan will also appreciate, once armed with the teachings of the present invention, and the three-dimensional structure reported herein, that this may be accomplished through the substitution of residues within the active site of NPP1, as enabled by disclosures, findings, and knowledge contained and described herein. Mutations of this effect are therefore claimed as methods of art by this application.

The skilled artisan will also appreciate, once armed with the teachings of the present invention, and the three-dimensional structure reported herein, that decreasing the prothrombotic activity of NPP1 or a mutant thereof encompasses the manipulation of specific residues in NPP1 to effect alterations of the Michaelis-Menton constants of the enzyme to decrease the affinity of NPP1 for Ap3A ($K_m$), or to decrease the turnover rate of Ap3A into ADP by NPP1 ($k_{cat}$). Mutations which accomplish this effect are therefore claimed as methods of art by this application. The skilled artisan will also appreciate, once armed with the teachings of the present invention, and the three-dimensional structure reported herein, including the docked molecule of Ap3A into NPP1 detailed in FIGS. 9A-9F and 11, that this may be accomplished through the substitution or alterations of amino acids lining the adenine binding pockets of NPP4 into amino acids that increase the occupied space of the amino acids which reduce or eliminate the adenine binding pocket of Ap3A, as enabled by disclosures, findings, the molecular structure of NPP1, and the use of the molecular structures of the model of NPP1 bound to Ap3A as depicted in FIGS. 6A-6C-7A-7D, 9A-9F, and 11, and other knowledge contained and described herein. Mutations to this effect are therefore claimed as methods of art by this application.

Thus, the present invention relates to the prevention and treatment of a disease or disorder by administration of an NPP1 polypeptide, a recombinant NPP1 polypeptide, a mutant NPP1 polypeptide, an active NPP1 polypeptide fragment, or an activator of NPP1 expression or activity. In one embodiment, the NPP1 polypeptide or mutant thereof is soluble. In another embodiment, the NPP1 polypeptide or mutant thereof is a recombinant NPP1 polypeptide. In one embodiment, the NPP1 polypeptide or mutant thereof includes an NPP1 polypeptide that lacks the NPP1 transmembrane domain. In another embodiment, the NPP1 polypeptide or mutant thereof includes an NPP1 polypeptide where the NPP1 transmembrane domain has been removed and replaced with the transmembrane domain of another polypeptide, such as, by way of non-limiting example, NPP2.

In some embodiments, the NPP1 polypeptide or mutant thereof comprises an IgG Fc domain. In other embodiments, the NPP1 polypeptide or mutant thereof comprises a polyaspartic acid domain comprise from about 2 to about 20 or more sequential aspartic acid residues to target the NPP1 polypeptide to bone. In some embodiments, the NPP1 polypeptide or mutant thereof comprises an IgG Fc domain and a polyaspartic acid domain comprising from about 2 to about 20 or more sequential aspartic acid residues. In other embodiments, the NPP1 protein or mutant thereof is truncated to remove the nuclease domain. In a particular embodiment, the NPP1 protein or mutant thereof is truncated to remove the nuclease domain from about residue 524 to about residue 885 relative to SEQ ID NO:1, leaving only the catalytic domain from about residue 186 to about residue 586 relative to SEQ ID NO:1, which serves to preserve the catalytic activity of the protein.

It is understood by one skilled in the art, that an increase in the level of NPP1 or mutant thereof encompasses an increase in the amount of NPP1 or mutant thereof (e.g., by administration of NPP1, fragment thereof or mutant thereof, by increasing NPP1 protein expression, etc.). Additionally, the skilled artisan would appreciate, that an increase in the level of NPP1 or mutant thereof includes an increase in NPP1 activity. Thus, increasing the level or activity of NPP1 or mutant thereof includes, but is not limited to, the administration of NPP1, fragment thereof or mutant thereof, as well as increasing transcription, translation, or both, of a nucleic acid encoding NPP1 or mutant thereof; and it also includes increasing any activity of NPP1 or mutant thereof as well.

The increased level or activity of NPP1 or mutant thereof can be assessed using a wide variety of methods, including those disclosed herein, as well as methods well-known in the art or to be developed in the future. That is, the routineer would appreciate, based upon the disclosure provided herein, that increasing the level or activity of NPP1 or mutant thereof can be readily assessed using methods that assess the level of a nucleic acid encoding NPP1 or mutant thereof (e.g., mRNA) to alter the Michaelis Menton kinetics to substrate and product turnover as described herein, the level of NPP1 polypeptide or mutant thereof, and/or the level of activity in a biological sample obtained from a subject.

One skilled in the art, based upon the disclosure provided herein, would understand that the invention is useful in subjects who, in whole (e.g., systemically) or in part (e.g., locally, tissue, organ), are being, or will be, treated for pathological calcification or ossification. In one embodiment, the invention is useful in treating or preventing pathological calcification or ossification. The skilled artisan will appreciate, based upon the teachings provided herein, that the diseases and disorders treatable by the compositions and methods described herein encompass any disease or disorder where a decrease in calcification or ossification will promote a positive therapeutic outcome.

One of skill in the art will realize that in addition to activating NPP1 or mutant thereof directly, diminishing the amount or activity of a molecule that itself diminishes the amount or activity of NPP1 or mutant thereof can serve to increase the amount or activity of NPP1 or mutant thereof. Thus, an activator can include, but should not be construed as being limited to, a chemical compound, a protein, a peptidomimetic, an antibody, a ribozyme, and an antisense nucleic acid molecule. One of skill in the art would readily appreciate, based on the disclosure provided herein, that an activator encompasses a chemical compound that increases the level, enzymatic activity, or substrate binding activity of NPP1 or mutant thereof. Additionally, an activator encompasses a chemically modified compound, and derivatives, as is well known to one of skill in the chemical arts.

It will be understood by one skilled in the art, based upon the disclosure provided herein, that an increase in the level of NPP1 or mutant thereof encompasses the increase in expression, including transcription, translation, or both, of NPP1 or mutant thereof. The skilled artisan will also appreciate, once armed with the teachings of the present invention, that an increase in the level of NPP1 or mutant thereof includes an increase in activity (e.g., enzymatic activity, substrate binding activity, etc.) of NPP1 or mutant thereof. Thus, increasing the level or activity of NPP1 or mutant thereof includes, but is not limited to, increasing the amount of NPP1 polypeptide or mutant thereof, increasing transcription, translation, or both, of a nucleic acid encoding NPP1 or mutant thereof; and it also includes increasing any activity of an NPP1 polypeptide or mutant thereof as well. The activator compositions and methods of the invention can selectively activate NPP1 or mutant thereof, or can activate both NPP1 or mutant thereof and another molecule, such as, by way of non-limiting example, NPP4.

Thus, the present invention relates to administration of an NPP1 polypeptide, a recombinant NPP1 polypeptide, a mutant NPP1 polypeptide, an active NPP1 polypeptide fragment, or an activator of NPP1 expression or activity. In one embodiment, the NPP1 polypeptide or mutant thereof is soluble. In another embodiment, the NPP1 polypeptide or mutant thereof is a recombinant polypeptide. In one embodiment, the NPP1 polypeptide or mutant thereof includes an NPP1 polypeptide or mutant thereof that lacks the NPP1 transmembrane domain. In another embodiment, the NPP1 polypeptide or mutant thereof includes an NPP1 polypeptide or mutant thereof where the NPP1 transmembrane domain or mutant thereof has been removed and replaced with the transmembrane domain of another polypeptide, such as, by way of non-limiting example, NPP2.

Further, one of skill in the art would, when equipped with this disclosure and the methods exemplified herein, appreciate that an NPP1 activator includes such activators as discovered in the future, as can be identified by well-known criteria in the art of pharmacology, such as the physiological results of activation of NPP1 as described in detail herein and/or as known in the art. Therefore, the present invention is not limited in any way to any particular NPP1 activator or mutant NPP1 activator as exemplified or disclosed herein; rather, the invention encompasses those activators that would be understood by the routineer to be useful as are known in the art and as are discovered in the future.

Further methods of identifying and producing an NPP1 activator are well known to those of ordinary skill in the art, including, but not limited, obtaining an activator from a naturally occurring source (e.g., *Streptomyces* sp *Pseudomonas* sp., *Stylotella aurantium*, etc.). Alternatively, an NPP1 activator can be synthesized chemically. Further, the routineer would appreciate, based upon the teachings provided herein, that an NPP1 activator can be obtained from a recombinant protein expression system, including but not limited to mammalian protein expression systems, insect cell protein expression systems, and yeast protein expression systems. Compositions and methods for chemically synthesizing NPP1 activators or mutant NPP1 activators and for obtaining them from natural sources are well known in the art and are described in the art.

One of skill in the art will appreciate that an activator can be administered as a small molecule chemical, a protein, a nucleic acid construct encoding a protein, or combinations thereof. Numerous vectors and other compositions and methods are well known for administering a protein or a nucleic acid construct encoding a protein to cells or tissues. Therefore, the invention includes a method of administering a protein or a nucleic acid encoding a protein that is an activator of NPP1 or mutant thereof (Sambrook et al., 2012, Molecular Cloning: A Laboratory Manual, Cold Spring Harbor Laboratory, New York; Ausubel et al., 1997, Current Protocols in Molecular Biology, John Wiley & Sons, New York).

One of skill in the art will realize that diminishing the amount or activity of a molecule that itself diminishes the amount or activity of NPP1 or mutant thereof can serve to increase the amount or activity of NPP1 or mutant thereof. Antisense oligonucleotides are DNA or RNA molecules that are complementary to some portion of an mRNA molecule. When present in a cell, antisense oligonucleotides hybridize to an existing mRNA molecule and inhibit translation into a gene product. Inhibiting the expression of a gene using an antisense oligonucleotide is well known in the art (Marcus-Sekura, 1988, Anal. Biochem. 172:289), as are methods of expressing an antisense oligonucleotide in a cell (Inoue, U.S. Pat. No. 5,190,931). The methods of the invention include the use of antisense oligonucleotide to diminish the amount of a molecule that causes a decrease in the amount or activity NPP1 or mutant thereof, thereby increasing the amount or activity of NPP1 or mutant thereof. Contemplated in the present invention are antisense oligonucleotides that are synthesized and provided to the cell by way of methods well known to those of ordinary skill in the art. As an example, an antisense oligonucleotide can be synthesized to be between about 10 and about 100, more preferably between about 15 and about 50 nucleotides long. The synthesis of nucleic acid molecules is well known in the art, as is the synthesis of modified antisense oligonucleotides to improve biological activity in comparison to unmodified antisense oligonucleotides (U.S. Pat. No. 5,023,243).

Similarly, the expression of a gene may be inhibited by the hybridization of an antisense molecule to a promoter or other regulatory element of a gene, thereby affecting the transcription of the gene. Methods for the identification of a promoter or other regulatory element that interacts with a gene of interest are well known in the art, and include such methods as the yeast two hybrid system (Bartel and Fields, eds., In: The Yeast Two Hybrid System, Oxford University Press, Cary, N.C.).

Alternatively, inhibition of a gene expressing a protein that diminishes the level or activity of NPP1 or mutant thereof can be accomplished through the use of a ribozyme. Using ribozymes for inhibiting gene expression is well known to those of skill in the art (see, e.g., Cech et al., 1992, J. Biol. Chem. 267:17479; Hampel et al., 1989, Biochemistry 28: 4929; Altman et al., U.S. Pat. No. 5,168,053). Ribozymes are catalytic RNA molecules with the ability to cleave other single-stranded RNA molecules. Ribozymes are known to be sequence specific, and can therefore be modified to recognize a specific nucleotide sequence (Cech, 1988, J. Amer. Med. Assn. 260:3030), allowing the selective cleavage of specific mRNA molecules. Given the nucleotide sequence of the molecule, one of ordinary skill in the art could synthesize an antisense oligonucleotide or ribozyme without undue experimentation, provided with the disclosure and references incorporated herein.

One of skill in the art will appreciate that an NPP1 activator, NPP1 polypeptide, a recombinant NPP1 polypeptide, a mutant NPP1 polypeptide, or an active NPP1 polypeptide fragment can be administered singly or in any combination thereof. One of skill in the art will also appreciate administration can be acute (e.g., over a short period of time, such as a day, a week or a month) or chronic (e.g., over a long period of time, such as several weeks, several months or a year or more). Further, an NPP1 polypeptide, a recombinant NPP1 polypeptide, a mutant NPP1 polypeptide, or an active NPP1 polypeptide fragment can be administered singly or in any combination thereof in a temporal sense, in that they may be administered simultaneously, before, and/or after each other. One of ordinary skill in the art will appreciate, based on the disclosure provided herein, that an NPP1 polypeptide, a recombinant NPP1 polypeptide, a mutant NPP1 polypeptide, or an active NPP1 polypeptide fragment can be used to treat or prevent pathological calcification or ossification, and that an activator can be used alone or in any combination with another NPP1 polypeptide, recombinant NPP1 polypeptide, active NPP1 polypeptide fragment, or NPP1 activator to effect a therapeutic result.

It will be appreciated by one of skill in the art, when armed with the present disclosure including the methods detailed herein, that the invention is not limited to treatment of a disease or disorder once is established. Particularly, the symptoms of the disease or disorder need not have manifested to the point of detriment to the subject; indeed, the disease or disorder need not be detected in a subject before treatment is administered. That is, significant pathology from disease or disorder does not have to occur before the present invention may provide benefit. Therefore, the present invention, as described more fully herein, includes a method for preventing diseases and disorders in a subject, in that an NPP1 polypeptide, fragment, derivative or mutant thereof, or an NPP1 activator or mutant NPP1 activator, as discussed elsewhere herein, can be administered to a subject prior to the onset of the disease or disorder, thereby preventing the disease or disorder from developing.

One of skill in the art, when armed with the disclosure herein, would appreciate that the prevention of a disease or disorder in a subject encompasses administering to a subject an NPP1 polypeptide, a recombinant NPP1 polypeptide, a mutant NPP1 polypeptide, an active NPP1 polypeptide fragment, or NPP1 activator as a preventative measure against a disease or disorder. In one embodiment, the NPP1 polypeptide is soluble. In another embodiment, the NPP1 polypeptide is a recombinant NPP1 polypeptide. In one embodiment, the NPP1 polypeptide includes an NPP1 polypeptide that lacks the NPP1 transmembrane domain. In another embodiment, the NPP1 polypeptide includes an NPP1 polypeptide where the NPP1 transmembrane domain has been removed and replaced with the transmembrane domain of another polypeptide, such as, by way of non-limiting example, NPP2.

In some embodiments, the NPP1 polypeptide comprises an IgG Fc domain. In other embodiments, the NPP1 polypeptide comprises a polyaspartic acid domain comprise from about 2 to about 20 or more sequential aspartic acid residues to target the NPP1 polypeptide to bone. In some embodiments, the NPP1 polypeptide comprises an IgG Fc domain and a polyaspartic acid domain comprising from about 2 to about 20 or more sequential aspartic acid residues. In other embodiments, the NPP1 protein is truncated to remove the nuclease domain. In a particular embodiment, NPP1 protein is truncated to remove the nuclease domain from about residue 524 to about residue 885 relative to SEQ ID NO:1, leaving only the catalytic domain from about residue 186 to about residue 586 relative to SEQ ID NO:1, which serves to preserve the catalytic activity of the protein.

As more fully discussed elsewhere herein, methods of increasing the level or activity of an NPP1 encompass a wide plethora of techniques for increasing not only NPP1 activity, but also for increasing expression of a nucleic acid encoding NPP1. Additionally, as disclosed elsewhere herein, one skilled in the art would understand, once armed with the teaching provided herein, that the present invention encompasses a method of preventing a wide variety of diseases or disorders where increased expression and/or activity of NPP1 mediates, treats or prevents a disease or disorder. Further, the invention encompasses treatment or prevention of such diseases or disorders discovered in the future.

The invention encompasses administration of an NPP1 polypeptide, a recombinant NPP1 polypeptide, a mutant NPP1 polypeptide, an active NPP1 polypeptide fragment, an NPP1 activator, or a mutant NPP4 polypeptide modified to exhibit NPP1-like ATP hydrolase activity to practice the methods of the invention; the skilled artisan would understand, based on the disclosure provided herein, how to formulate and administer the appropriate NPP1 polypeptide, recombinant NPP1 polypeptide, active NPP1 polypeptide fragment, or NPP1 activator to a subject. However, the present invention is not limited to any particular method of administration or treatment regimen. This is especially true where it would be appreciated by one skilled in the art, equipped with the disclosure provided herein, including the reduction to practice using an art-recognized model of pathological calcification or ossification, that methods of administering an NPP1 polypeptide, a recombinant NPP1 polypeptide, a mutant NPP1 polypeptide, an active NPP1 polypeptide fragment, or NPP1 activator can be determined by one of skill in the pharmacological arts.

NPP4 Therapeutic Activator Compositions and Methods

In various embodiments, the present invention includes NPP4 activator compositions and methods of increasing the level or activity of NPP4. In various embodiments, the NPP4 activator compositions and methods of treatment of the invention increase the amount of NPP4 polypeptide, the amount of NPP4 mRNA, the amount of NPP4 enzymatic activity, the amount of NPP4 substrate binding activity, or a combination thereof. In various embodiments, the diseases and disorders where a decrease in pathological calcification or ossification may improve therapeutic outcome include, but are not limited to, IIAC, OPLL, hypophosphatemic rickets, osteoarthritis, and the calcification of atherosclerotic plaques.

It will be understood by one skilled in the art, based upon the disclosure provided herein, including the three-dimensional structure reported herein, that an increase in the ATP hydrolytic activity of NPP4 or mutant thereof encompasses manipulations of specific amino acids in NPP4 to affect alteration of the Michaelis-Menton constants that either increase the affinity of the enzyme for ATP (increase the $K_m$) or to increase the turnover rate of ATP into $PP_i$ by NPP4 (increase the $k_{cat}$). The skilled artisan will also appreciate, once armed with the teachings of the present invention, including the three-dimensional structure reported herein, that this may be accomplished through the substitution of residues within the active site of NPP1 into the active site of NPP4, as enabled by disclosures, findings, and knowledge contained and described herein, including but not limited to the detailed analysis of the active sites of the two enzyme depicted in FIGS. 9A-9F, and the reproduction of the lysine claw in NPP1 within NPP4. Mutations of this effect are therefore claimed as methods of art by this application.

The skilled artisan will also appreciate, once armed with the teachings of the present invention, and the three-dimensional structure reported herein, that decreasing the prothrombotic activity of NPP4 or a mutant thereof encompasses the alteration of the Michaelis-Menton constants of the enzyme to decrease the affinity of NPP4 for Ap3A (decrease the $K_m$), or to decrease the turnover rate of Ap3A into ADP by NPP1 (decrease the $k_{cat}$). The skilled artisan will also appreciate, once armed with the teachings of the present invention, and the three-dimensional structure reported herein, including the docked molecule of Ap3A into NPP4, that this may be accomplished through the substitution or alterations of amino acids lining the adenine binding pockets of NPP4 into amino acids that increase the occupied space of said amino acids to reduce or eliminate the adenine binding pockets of Ap3A within NPP4, as enabled by disclosures, findings, the molecular structure of NPP4, and the molecular structure of the model of NPP4 bound to Ap3A, as detailed in FIGS. 6A-6C,-7A-7D, 9A-9F and 11, and other knowledge contained and described herein. Mutations of this effect are therefore claimed as methods of art by this application.

It will be understood by one skilled in the art, based upon the disclosure provided herein, that an increase in the level of NPP4 encompasses the increase in NPP4 expression, including transcription, translation, or both. The skilled artisan will also appreciate, once armed with the teachings of the present invention, that an increase in the level of NPP4 includes an increase in NPP4 activity (e.g., enzymatic activity, substrate binding activity, etc.). Thus, increasing the level or activity of NPP4 includes, but is not limited to, increasing the amount of NPP4 polypeptide, and increasing transcription, translation, or both, of a nucleic acid encoding NPP4; and it also includes increasing any activity of an NPP4 polypeptide as well. The NPP4 activator compositions and methods of the invention can selectively activate NPP4, or can activate both NPP4 and another molecule, such as, by way of a non-limiting example, NPP1.

Thus, the present invention relates to the prevention and treatment of a disease or disorder by administration of NPP4, including an NPP4 polypeptide, a recombinant NPP4 polypeptide, a mutant NPP4 polypeptide, an active NPP4 polypeptide fragment, or an activator of NPP4 expression or activity. In one embodiment, the NPP4 is soluble. In another embodiment, the NPP4 is a recombinant NPP4 polypeptide. In one embodiment, the NPP4 includes an NPP4 polypeptide that lacks the NPP4 transmembrane domain. In another embodiment, the NPP4 includes an NPP4 polypeptide where the NPP4 transmembrane domain has been removed and replaced with the transmembrane domain of another polypeptide. In one embodiment, the NPP4 includes an NPP4 polypeptide that lacks the NPP4 cytoplasmic domain. In another embodiment, the NPP4 includes an NPP4 polypeptide where the NPP4 cytoplasmic domain has been removed and replaced with the cytoplasmic domain of another polypeptide. In yet another embodiment, the NPP4 is modified to exhibit NPP1-like ATP hydrolytic activity. In one embodiment, the mutant NPP4 polypeptide is modified to exhibit NPP1-like ATP hydrolytic activity is fused to IgG Fc and/or a polyaspartic acid domains, as described elsewhere herein.

In one embodiment, the mutant NPP4 polypeptide comprises at least one mutation that changes the substrate selectivity of the NPP4 polypeptide from Ap3A to ATP. In various embodiments, the mutant NPP4 polypeptide comprises at least one mutation that changes the substrate selectivity of the NPP4 polypeptide from Ap3A to ATP, such as, by way of non-limiting examples, D335, S92, D264, L265, 5330, Q331, K332, or T323, relative to SEQ ID NO:3.

It is understood by one skilled in the art, that an increase in the level of NPP4 encompasses an increase in the amount of NPP4 (e.g., by administration of NPP4 or a mutant or fragment thereof, by increasing NPP4 protein expression, etc.). Additionally, the skilled artisan would appreciate, that an increase in the level of NPP4 includes an increase in NPP4 activity. Thus, increasing the level or activity of NPP4 includes, but is not limited to, the administration of NPP4 or a mutant or fragment thereof, as well as increasing transcription, translation, or both, of a nucleic acid encoding NPP4; and it also includes increasing any activity of NPP4 as well.

The increased level or activity of NPP4 can be assessed using a wide variety of methods, including those disclosed herein, as well as methods well-known in the art or to be developed in the future. That is, the routineer would appreciate, based upon the disclosure provided herein, that increasing the level or activity of NPP4 can be readily assessed using methods that assess the level of a nucleic acid encoding NPP4 (e.g., mRNA), the level of NPP4 polypeptide, and/or the level of NPP4 activity in a biological sample obtained from a subject.

One skilled in the art, based upon the disclosure provided herein, would understand that the invention is useful in subjects who, in whole (e.g., systemically) or in part (e.g., locally, tissue, organ), are being or will be, treated for pathological calcification or ossification. In one embodiment, the invention is useful in treating or preventing pathological calcification or ossification. The skilled artisan will appreciate, based upon the teachings provided herein, that the diseases and disorders treatable by the compositions and methods described herein encompass any disease or disorder where a decrease in calcification or ossification will promote a positive therapeutic outcome.

One of skill in the art will realize that in addition to activating NPP4 directly, diminishing the amount or activity of a molecule that itself diminishes the amount or activity of NPP4 can serve to increase the amount or activity of NPP4. Thus, an NPP4 activator can include, but should not be construed as being limited to, a chemical compound, a protein, a peptidomimetic, an antibody, a ribozyme, and an antisense nucleic acid molecule. One of skill in the art would readily appreciate, based on the disclosure provided herein, that an NPP4 activator encompasses a chemical compound that increases the level, enzymatic activity, or substrate binding activity of NPP4. Additionally, an NPP4 activator encompasses a chemically modified compound, and derivatives, as is well known to one of skill in the chemical arts.

It will be understood by one skilled in the art, based upon the disclosure provided herein, that an increase in the level of NPP4 encompasses the increase in NPP4 expression, including transcription, translation, or both. The skilled artisan will also appreciate, once armed with the teachings of the present invention, that an increase in the level of NPP4 includes an increase in NPP4 activity (e.g., enzymatic activity, substrate binding activity, etc.). Thus, increasing the level or activity of NPP4 includes, but is not limited to, increasing the amount of NPP4 polypeptide, increasing transcription, translation, or both, of a nucleic acid encoding NPP4; and it also includes increasing any activity of an NPP4 polypeptide as well. The NPP4 activator compositions and methods of the invention can selectively activate NPP4, or can activate both NPP4 and another molecule, such as, by way of non-limiting example, NPP1. Thus, the present invention relates to administration of an NPP4 polypeptide, a recombinant NPP4 polypeptide, a mutant NPP4 polypeptide, an active NPP4 polypeptide fragment, or an activator of NPP4 expression or activity. In one embodiment, the NPP4 is soluble. In another embodiment, the NPP4 is a recombinant NPP4 polypeptide. In one embodiment, the NPP4 includes an NPP4 polypeptide that lacks the NPP4 transmembrane domain. In another embodiment, the NPP4 includes an NPP4 polypeptide where the NPP4 transmembrane domain has been removed and replaced with the transmembrane domain of another polypeptide. In one embodiment, the NPP4 includes an NPP4 polypeptide that lacks the NPP4 cytoplasmic domain. In another embodiment, the NPP4 includes an NPP4 polypeptide where the NPP4 cytoplasmic domain has been removed and replaced with the cytoplasmic domain of another polypeptide. In yet another embodiment, the NPP4 is modified to exhibit NPP1-like ATP hydrolytic activity. In one embodiment, the NPP4 modified to exhibit NPP1-like ATP hydrolytic activity is fused to IgG Fc and/or polyaspartic acid domains, as described elsewhere herein. In one embodiment, the mutant NPP4 polypeptide comprises at least one mutation that changes the substrate selectivity of the NPP4 polypeptide from Ap3A to ATP. In various embodiments, the NPP4 polypeptide comprises at least one mutation that changes the substrate selectivity of the NPP4 polypeptide from Ap3A to ATP, such as, by way of non-limiting examples, D335, S92, D264, L265, 5330, Q331, K332, or T323, relative to SEQ ID NO:3.

Further, one of skill in the art would, when equipped with this disclosure and the methods exemplified herein, appreciate that an NPP4 activator includes such activators as discovered in the future, as can be identified by well-known criteria in the art of pharmacology, such as the physiological results of activation of NPP4 as described in detail herein and/or as known in the art. Therefore, the present invention is not limited in any way to any particular NPP4 activator as exemplified or disclosed herein; rather, the invention encompasses those activators that would be understood by the routineer to be useful as are known in the art and as are discovered in the future.

Further methods of identifying and producing an NPP4 activator are well known to those of ordinary skill in the art, including, but not limited, obtaining an activator from a naturally occurring source (e.g., *Streptomyces* sp., *Pseudomonas* sp., *Stylotella aurantium*, etc.). Alternatively, an NPP4 activator can be synthesized chemically. Further, the routineer would appreciate, based upon the teachings provided herein, that an NPP4 activator can be obtained from a recombinant organism. Compositions and methods for chemically synthesizing NPP4 activators and for obtaining them from natural sources are well known in the art and are described in the art.

One of skill in the art will appreciate that an activator can be administered as a small molecule chemical, a protein, a nucleic acid construct encoding a protein, or combinations thereof. Numerous vectors and other compositions and methods are well known for administering a protein or a nucleic acid construct encoding a protein to cells or tissues. Therefore, the invention includes a method of administering a protein or a nucleic acid encoding a protein that is an activator of NPP4 (Sambrook et al., 2012, Molecular Cloning: A Laboratory Manual, Cold Spring Harbor Laboratory, New York; Ausubel et al., 1997, Current Protocols in Molecular Biology, John Wiley & Sons, New York).

One of skill in the art will realize that diminishing the amount or activity of a molecule that itself diminishes the amount or activity of NPP4 can serve to increase the amount or activity of NPP4. Antisense oligonucleotides are DNA or RNA molecules that are complementary to some portion of an mRNA molecule. When present in a cell, antisense oligonucleotides hybridize to an existing mRNA molecule and inhibit translation into a gene product. Inhibiting the expression of a gene using an antisense oligonucleotide is well known in the art (Marcus-Sekura, 1988, Anal. Biochem. 172:289), as are methods of expressing an antisense oligonucleotide in a cell (Inoue, U.S. Pat. No. 5,190, 931). The methods of the invention include the use of antisense oligonucleotide to diminish the amount of a molecule that causes a decrease in the amount or activity NPP4, thereby increasing the amount or activity of NPP4. Contemplated in the present invention are antisense oligonucleotides that are synthesized and provided to the cell by way of methods well known to those of ordinary skill in the art. As an example, an antisense oligonucleotide can be synthesized to be between about 10 and about 100, more preferably between about 15 and about 50 nucleotides long. The synthesis of nucleic acid molecules is well known in the art, as is the synthesis of modified antisense oligonucleotides to improve biological activity in comparison to unmodified antisense oligonucleotides (Tullis, 1991, U.S. Pat. No. 5,023,243).

Similarly, the expression of a gene may be inhibited by the hybridization of an antisense molecule to a promoter or other regulatory element of a gene, thereby affecting the transcription of the gene. Methods for the identification of a promoter or other regulatory element that interacts with a gene of interest are well known in the art, and include such methods as the yeast two hybrid system (Bartel and Fields, eds., In: The Yeast Two Hybrid System, Oxford University Press, Cary, N.C.).

Alternatively, inhibition of a gene expressing a protein that diminishes the level or activity of NPP4 can be accomplished through the use of a ribozyme. Using ribozymes for inhibiting gene expression is well known to those of skill in the art (see, e.g., Cech et al., 1992, J. Biol. Chem. 267: 17479; Hampel et al., 1989, Biochemistry 28: 4929; Altman et al., U.S. Pat. No. 5,168,053). Ribozymes are catalytic RNA molecules with the ability to cleave other single-stranded RNA molecules. Ribozymes are known to be sequence specific, and can therefore be modified to recognize a specific nucleotide sequence (Cech, 1988, J. Amer. Med. Assn. 260:3030), allowing the selective cleavage of specific mRNA molecules. Given the nucleotide sequence of the molecule, one of ordinary skill in the art could synthesize an antisense oligonucleotide or ribozyme without undue experimentation, provided with the disclosure and references incorporated herein.

One of skill in the art will appreciate that an NPP4 activator, NPP4 polypeptide, a recombinant NPP4 polypeptide, a mutant NPP4 polypeptide, or an active NPP4 polypeptide fragment can be administered singly or in any combination thereof. One of skill in the art will also appreciate administration can be acute (e.g., over a short period of time, such as a day, a week or a month) or chronic (e.g., over a long period of time, such as several weeks, several months or a year or more). Further, an NPP4 polypeptide, a recombinant NPP4 polypeptide, a mutant NPP4 polypeptide, or an active NPP4 polypeptide fragment can be administered singly or in any combination thereof in a temporal sense, in that they may be administered simultaneously, before, and/or after each other. One of ordinary skill in the art will appreciate, based on the disclosure provided herein, that an NPP4 polypeptide, a recombinant NPP4 polypeptide, a mutant NPP4 polypeptide, or an active NPP4 polypeptide fragment can be used to treat or prevent pathological calcification or ossification, and that an activator can be used alone or in any combination with another NPP4 polypeptide, recombinant NPP4 polypeptide, active NPP4 polypeptide fragment, or NPP4 activator to effect a therapeutic result.

It will be appreciated by one of skill in the art, when armed with the present disclosure including the methods detailed herein, that the invention is not limited to treatment of a disease or disorder once is established. Particularly, the symptoms of the disease or disorder need not have manifested to the point of detriment to the subject; indeed, the disease or disorder need not be detected in a subject before treatment is administered. That is, significant pathology from disease or disorder does not have to occur before the present invention may provide benefit. Therefore, the present invention, as described more fully herein, includes a method for preventing diseases and disorders in a subject, in that an NPP4 polypeptide, or a fragment, derivative, or mutant thereof, or an NPP4 activator, as discussed elsewhere herein, can be administered to a subject prior to the onset of the disease or disorder, thereby preventing the disease or disorder from developing.

One of skill in the art, when armed with the disclosure herein, would appreciate that the prevention of a disease or disorder in a subject encompasses administering to a subject NPP4, including an NPP4 polypeptide, a recombinant NPP4 polypeptide, a mutant NPP4 polypeptide, an active NPP4 polypeptide fragment, or NPP4 activator as a preventative measure against a disease or disorder. In one embodiment, the NPP4 is soluble. In another embodiment, the NPP4 is a recombinant NPP4 polypeptide. In one embodiment, the NPP4 includes an NPP4 polypeptide that lacks the NPP4 transmembrane domain. In another embodiment, the NPP4 includes an NPP4 polypeptide where the NPP4 transmembrane domain has been removed and replaced with the transmembrane domain of another polypeptide. In one embodiment, the NPP4 includes an NPP4 polypeptide that lacks the NPP4 cytoplasmic domain. In another embodiment, the NPP4 includes an NPP4 polypeptide where the NPP4 cytoplasmic domain has been removed and replaced with the cytoplasmic domain of another polypeptide. In yet another embodiment, the NPP4 is modified to exhibit NPP1-like ATP hydrolytic activity. In one embodiment, the NPP4 modified to exhibit NPP1-like ATP hydrolytic activity is fused to IgG Fc and/or polyaspartic acid domains, as described elsewhere herein. In one embodiment, the mutant NPP4 polypeptide comprises at least one mutation that changes the substrate selectivity of the NPP4 polypeptide from Ap3A to ATP. In various embodiments, the mutant NPP4 polypeptide comprises at least one mutation that changes the substrate selectivity of the NPP4 polypeptide from Ap3A to ATP, such as, by way of non-limiting examples, D335, S92, D264, L265, S330, Q331, K332, or T323, relative to SEQ ID NO:3.

As more fully discussed elsewhere herein, methods of increasing the level or activity of an NPP4 encompass a wide plethora of techniques for increasing not only NPP4 activity, but also for increasing expression of a nucleic acid encoding NPP4. Additionally, as disclosed elsewhere herein, one skilled in the art would understand, once armed with the teaching provided herein, that the present invention encompasses a method of preventing a wide variety of diseases or disorders where increased expression and/or activity of NPP4 mediates, treats or prevents a disease or disorder. Further, the invention encompasses treatment or prevention of such diseases or disorders discovered in the future.

The invention encompasses administration of NPP4, including an NPP4 polypeptide, a recombinant NPP4 polypeptide, a mutant NPP4 polypeptide, an active NPP4 polypeptide fragment, or an NPP4 activator to practice the methods of the invention; the skilled artisan would understand, based on the disclosure provided herein, how to formulate and administer the appropriate NPP4 polypeptide, recombinant NPP4 polypeptide, active NPP4 polypeptide fragment, or NPP4 activator to a subject. However, the present invention is not limited to any particular method of administration or treatment regimen. This is especially true where it would be appreciated by one skilled in the art, equipped with the disclosure provided herein, including the reduction to practice using an art-recognized model of pathological calcification or ossification, that methods of administering an NPP4 polypeptide, a recombinant NPP4 polypeptide, a mutant NPP4 polypeptide, an active NPP4 polypeptide fragment, or NPP4 activator can be determined by one of skill in the pharmacological arts.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Cloning and Expression

NPP1 and NPP4 are transmembrane proteins localized to the cell surface with distinct intramembrane domains. For example, NPP1 is in a type-II orientation while NPP4 is in a type-I orientation. In contrast, NPP2 is synthesized as a pre-pro-protein, and following proteolytic processing is secreted as a soluble protein following cleavage of the extracellular domain by furin (Jansen et al., 2005, J. Cell Sci. 118:3081-3089). To express NPP4 as a soluble, recombinant protein in baculovirus, the cytoplasmic and transmembrane domains were omitted from the protein construct. In contrast, to express NPP1 as a soluble extracellular protein, the transmembrane domain of NPP1 was swapped for the transmembrane domain of NPP2, which resulted in the accumulation of soluble, recombinant NPP1 in the extracellular fluid of the baculovirus cultures.

Figure 3:
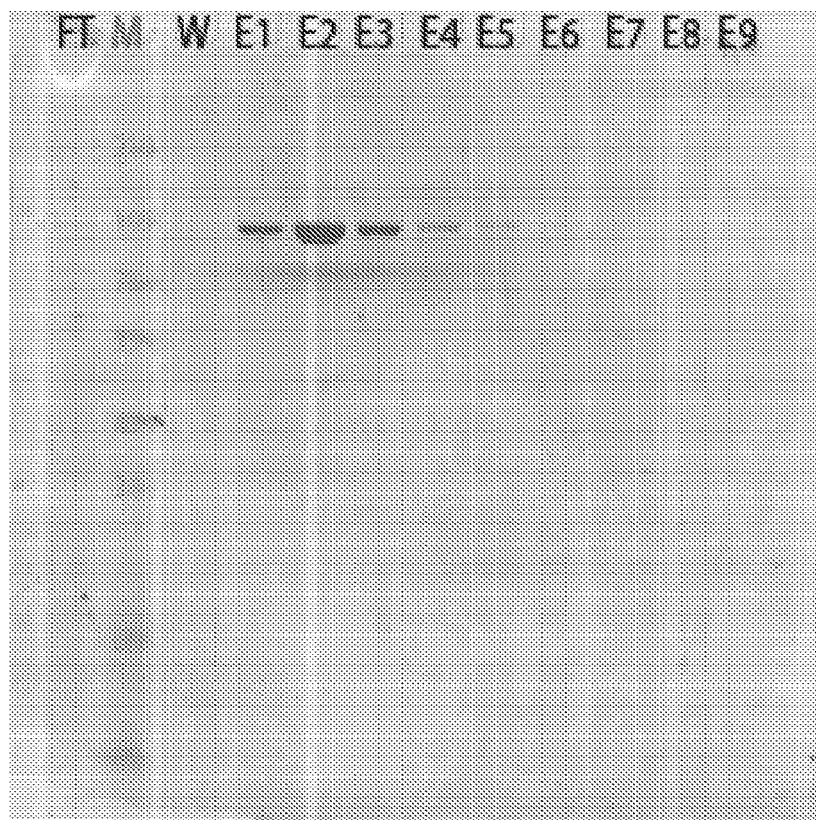
FIG. 3 is a photograph of a gel depicting the expression and purification of NPP1 in Baculovirus. Baculovirus cells were infected with NPP1 virus, and the extracellular media was collected following two days of incubation, concentrated, and run over a nickle column. Following washing with buffer, the protein was eluted with imidazole and 5 ml fractions were collected and run on an SDS-PAGE gel (E1-E9).

NPP1 can be made soluble by omitting the transmembrane domain. Human NPP1 (NCBI accession NP_006199) was modified to express a soluble, recombinant protein by replacing its transmembrane region (e.g., residues 77-98) with the corresponding subdomain of human NPP2 (NCBI accession NP_001124335, e.g., residues 12-30). The modified NPP1 sequence was cloned into a modified pFastbac HT vector possessing a TEV protease cleavage site followed by a C-terminus 9-HIS tag, and cloned and expressed in insect cells, and both proteins were expressed in a baculovirus system as described previously (Albright et al., 2012, Blood 120:4432-4440; Saunders et al., 2011, J. Biol. Chem. 18:994-1004; Saunders et al., 2008, Mol. Cancer Ther. 7:3352-3362), resulting in the accumulation of soluble, recombinant protein in the extracellular fluid (FIGS. 2-3).

Sequences

NPP1 Amino Acid Sequence (NCBI accession
NP_006199) (SEQ ID NO: 1)
MERDGCAGGGSRGGEGGRAPREGPAGNGRDRGRSHAAEAPGDPQAAASLL
APMDVGEEPLEKAARARTAKDPNTYKVLSLVLSVCVLTTILGCIFGLKPS
CAKEVKSCKGRCFERTFGNCRCDAACVELGNCCLDYQETCIEPEHIWTCN
KFRCGEKRLTRSLCACSDDCKDKGDCCINYSSVCQGEKSWVEEPCESINE
PQCPAGFETPPTLLFSLDGFRAEYLHTWGGLLPVISKLKKCGTYTKNMRP
VYPTKTFPNHYSIVTGLYPESHGIIDNKMYDPKMNASFSLKSKEKFNPEW
YKGEPIWVTAKYQGLKSGTFFWPGSDVEINGIFPDIYKMYNGSVPFEERI
LAVLQWLQLPKDERPHFYTLYLEEPDSSGHSYGPVSSEVIKALQRVDGMV
GMLMDGLKELNLHRCLNLILISDHGMEQGSCKKYIYLNKYLGDVKNIKVI
YGPAARLRPSDVPDKYYSFNYEGIARNLSCREPNQHFKPYLKHFLPKRLH
FAKSDRIEPLTFYLDPQWQLALNPSERKYCGSGFHGSDNVFSNMQALFVG
YGPGFKHGIEADTFENIEVYNLMCDLLNLTPAPNNGTHGSLNHLLKNPVY
TPKHPKEVHPLVQCPFTRNPRDNLGCSCNPSILPIEDFQTQFNLTVAEEK
IIKHETLPYGRPRVLQKENTICLLSQHQFMSGYSQDILMPLWTSYTVDRN
DSFSTEDFSNCLYQDFRIPLSPVHKCSFYKNNTKVSYGFLSPPQLNKNSS
GIYSEALLTTNIVPMYQSFQVIWRYFHDTLLRKYAEERNGVNVVSGPVFD
FDYDGRCDSLENLRQKRRVIRNQEILIPTHFFIVLTSCKDTSQTPLHCEN
LDTLAFILPHRTDNSESCVHGKHDSSWVEELLMLHRARITDVEHITGLSF
YQQRKEPVSDILKLKTHLPTFSQED NPP2 Amino Acid Sequence (NCBI accession
NP_001124335) (SEQ ID NO: 2)
MARRSSFQSCQIISLFTFAVGVNICLGFTAHRIKRAEGWEEGPPTVLSDS
PWTNISGSCKGRCFELQEAGPPDCRCDNLCKSYTSCCHDFDELCLKTARG
WECTKDRCGEVRNEENACHCSEDCLARGDCCTNYQVVCKGESHWVDDDCE
EIKAAECPAGFVRPPLIIFSVDGFRASYMKKGSKVMPNLELHKLRSCGTHSP
YMRPVYPTKTFPNLYTLATGLYPESHGIVGNSMYDPVFDATFHLRGREKF
NHRWWGGQPLWITATKQGVKAGTFFWSVVIPHERRILTILQWLTLPDHER
PSVYAFYSEQPDFSGHKYGPFGPEMTNPLREIDKIVGQLMDGLKQLKLHR
CVNVIFVGDHGMEDVTCDRTEFLSNYLTNVDDITLVPGTLGRIRSKFSNN
AKYDPKAIIANLTCKKPDQHFKPYLKQHLPKRLHYANNRRIEDIHLLVER
RWHVARKPLDVYKKPSGKCFFQGDHGFDNKVNSMQTVFVGYGSTFKYKTK
VPPFENIELYNVMCDLLGLKPAPNNGTHGSLNHLLRTNTFRPTMPEEVTR
PNYPGIMYLQSDFDLGCTCDDKVEPKNKLDELNKRLHTKGSTEAETRKFR
GSRNENKENINGNFEPRKERHLLYGRPAVLYRTRYDILYHTDFESGYSEI
FLMPLWTSYTVSKQAEVSSVPDHLTSCVRPDVRVSPSFSQNCLAYKNDKQ
MSYGFLFPPYLSSSPEAKYDAFLVTNMVPMYPAFKRVWNYFQRVLVKKYA
SERNGVNVISGPIFDYDYDGLHDTEDKIKQYVEGSSIPVPTHYYSIITSC
LDFTQPADKCDGPLSVSSFILPHRPDNEESCNSSEDESKWVEELMKMHTA
RVRDIEHLTSLDFFRKTSRSYPEILTLKTYLHTYESEI NPP4 Amino Acid Sequence (NCBI accession
AAH18054.1) (SEQ ID NO: 3)
MKLLVILLFSGLITGFRSDSSSSLPPKLLLVSFDGFRADYLKNYEFPHLQ
NFIKEGVLVEHVKNVFITKTFPNHYSIVTGLYEESHGIVANSMYDAVTKK
HFSDSNDKDPFWWNEAVPIWVTNQLQENRSSAAAMWPGTDVPIHDTISSY
FMNYNSSVSFEERLNNITMWLNNSNPPVTFATLYWEEPDASGHKYGPEDK
ENMSRVLKKIDDLIGDLVQRLKMLGLWENLNVIITSDHGMTQCSQDRLIN
LDSCIDHSYYTLIDLSPVAAILPKINRTEVYNKLKNCSPHMNVYLKEDIP
NRFYYQHNDRIQPIILVADEGWTIVLNESSQKLGDHGYDNSLPSMHPFLA
AHGPAFHKGYKHSTINIVDIYPMMCHILGLKPHPNNGTFGHTKCLLVDQW

Sequences
-continued

CINLPEAIAIVIGSLLVLTMLTCLIIMVIQNRLSVPRPFSRLQLQEDDDD
PLIG

Purification

Figure 4:
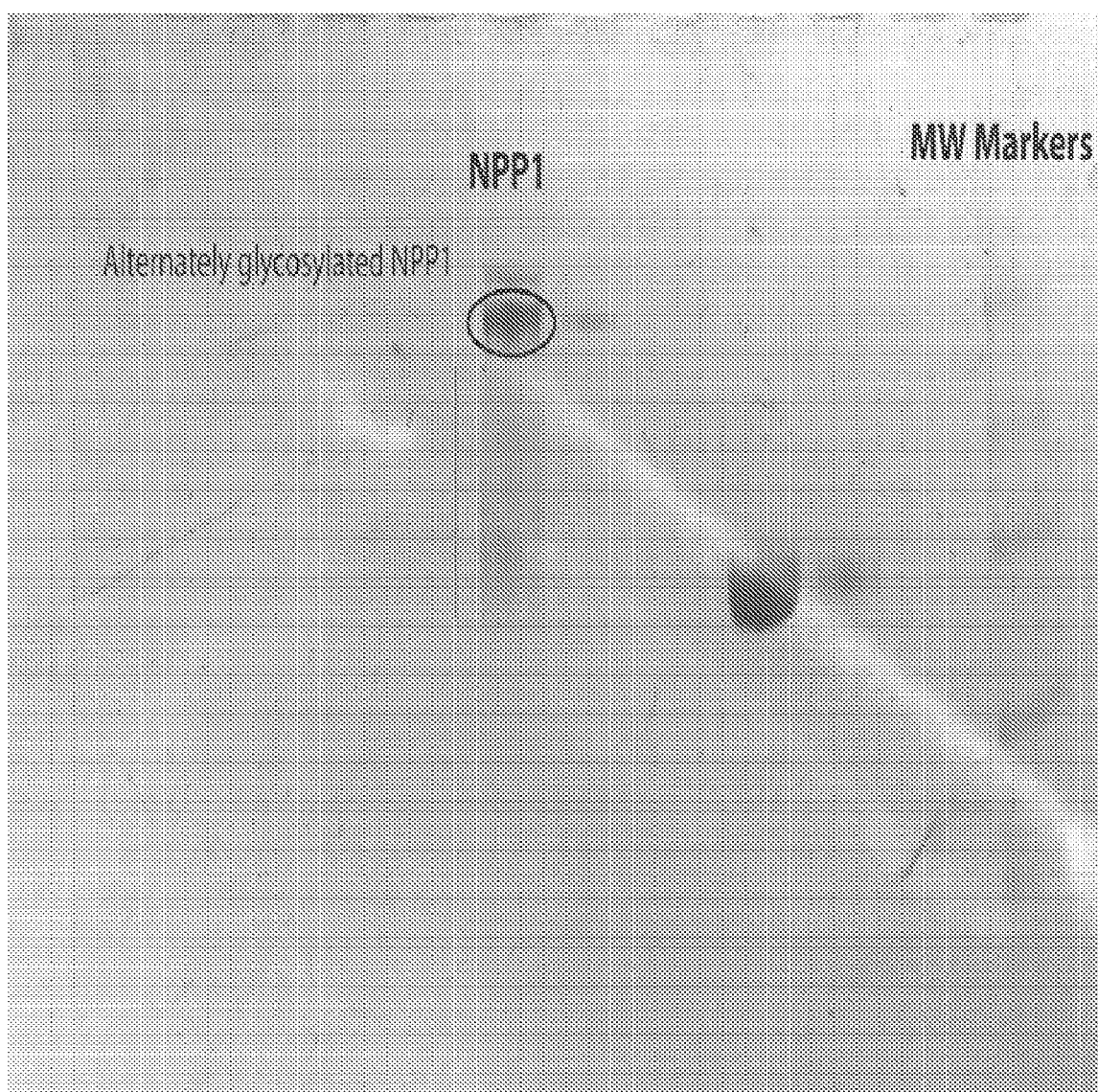
FIG. 4 is a photograph of a gel depicting the expression and purification of NPP1 in mammalian cells: To express NPP1 with mammalian glycosylations, NPP1 was produced in HEK293 kidney cells using an analogous expression and purification procedure which has been described for baculovirus. The SDS-PAGE gel of the purified protein is depicted. The concentration of the NPP1 stock solution as determined by amino acid analysis is 2.15 mg/ml.

The protein was purified by nickel affinity column, and following elution with imidazole, the C-terminal histidine tag was cut from the protein with tobacco etch virus (TEV) protease. Following cleavage of the histidine tag, a second round of purification on a nickel column was performed to remove the C-terminal histidine tag and contaminating proteins which non-specifically associate with the nickel column during the first round of purification. Soluble NPP1 elutes in the flow through and is collected and concentrated by spin concentration. The overall purification yields approximately 2 mg of pure protein per liter of cell culture (FIGS. 3-4). A similar general purification scheme has been described for biochemical, biophysical, and physiologic studies of several members of the NPP family (Albright et al., 2012, Blood 120:4432-4440; Saunders et al., 2011, J. Biol. Chem. 18:994-1004; Saunders et al., 2008, Mol. Cancer Ther. 7:3352-3362). Purification of the proteins containing the Fc domain of IgG may also be accomplished via binding to protein A or protein G columns, as known to those experienced in the art and science of protein purification.

Mammalian Expression System for NPP1

NPP1 is a glycosylated protein, and insect cell sugar moieties are expected to induce strong immunogenic reactions from a mammalian host. To reduce the possibility of inducing immune reactions by treating animals with recombinant NPP1, a mammalian expression system was used to replace insect cell glycosylation patterns with mammalian glycosylation patterns. The protein in the HEK293 mammalian kidney cell line was expressed by cloning the identical NPP1 construct into a mammalian expression vector followed by stable transfection into HEK293 cells. Stable clones were identified by immunoblot against His antibody. Strongly expressing clones were expanded and culture medium was collected and treated as described in the baculovirus purification scheme described elsewhere herein. The overall yield of protein was approximately 1.5 mg/liter of culture media, and the purity of the sample was greater than 95% (FIG. 4).

ATP Hydrolytic Activity of NPP1 and NPP4

Figure 5A:
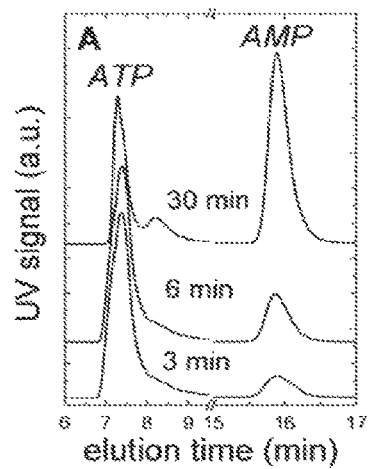
FIGS. 5A-5E illustrate the results of experiments assessing ATP cleavage and hydrolysis.
Figure 5C:
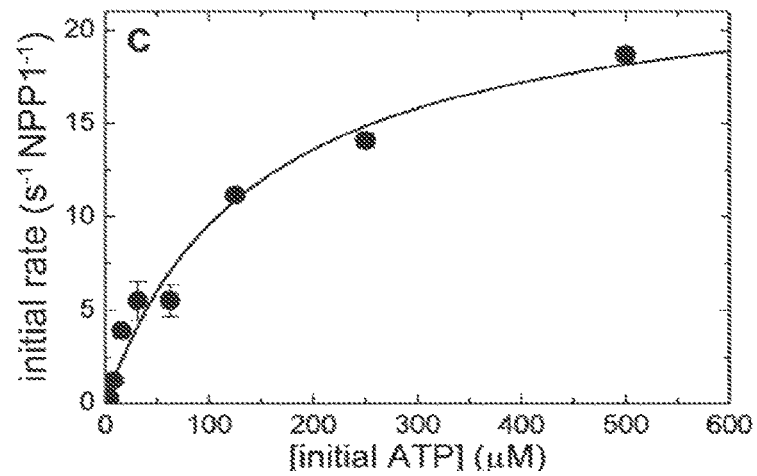
Figure 5B:
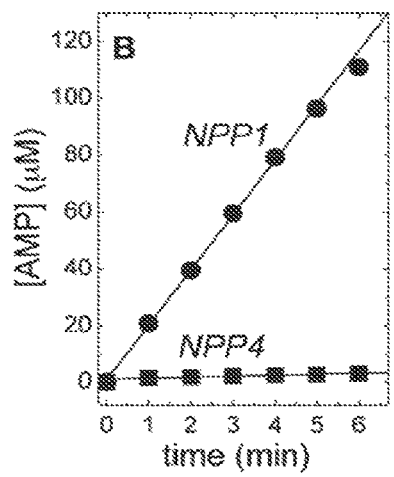
Figure 5D:
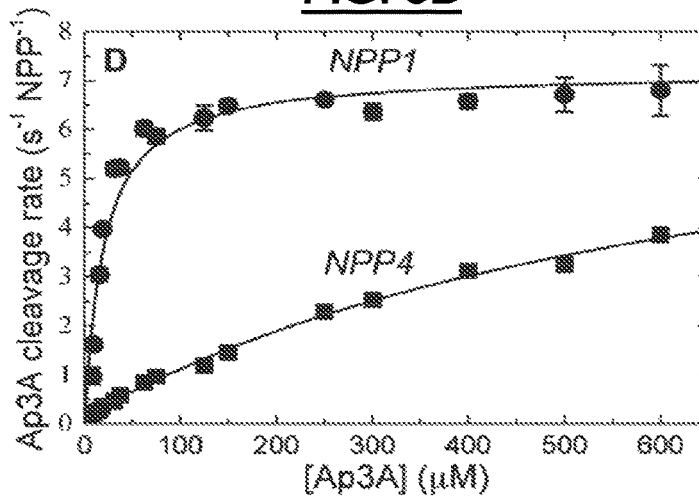

To verify that the extracellular, soluble domain of NPP1 is enzymatically active, the steady-state Michaelis-Menten enzymatic constants of NPP1 were determined using ATP as a substrate. In addition, to illustrate substrate specificity between NPP family members, the ATP hydrolysis of NPP1 was directly compared with NPP4, a protein with 38% sequence identity to NPP1. To verify that NPP1 cleaved ATP, HPLC analysis of the enzymatic reaction was used, and the identity of the substrates and products of the reaction was confirmed by using ATP, AMP, and ADP standards (FIGS. 5A-5E). The ATP substrate degrades over time in the presence of NPP1, with the accumulation of the enzymatic product AMP (FIGS. 5A-5E). Using varying concentrations of ATP substrate, the initial rate velocities for NPP1 were derived in the presence of ATP, and the data was fit to a curve to derive the enzymatic rate constants (FIG. 5C). In spite of significant sequence identity between NPP4 and NPP1, NPP4 had no ATP hydrolytic activity, while NPP1 readily hydrolyzed ATP into AMP and PPi (FIG. 5C). At physiologic pH, the kinetic rate constants of NPP1 are Km=144 µM and $k_{cat}$=7.8 s$^{-1}$.

HPLC Protocol

The HPLC protocol used to measure ATP cleavage by NPP1 and NPP4, and for product identification, was modified from the literature (Stocchi et al., 1985, Anal. Biochem. 146:118-124). The reactions containing varying concentrations of ATP in 50 mM Tris pH 8.0, 140 mM NaCl, 5 mM KCl, 1 mM MgCl$_2$ and 1 mM CaCl$_2$ buffer were started by addition of 0.2-1 µM NPP1 and quenched at various time points by equal volume of 3M formic acid, or 0.5N KOH and re-acidified by glacial acetic acid to pH 6. The quenched reaction solution was diluted systematically, loaded onto a HPLC system (Waters, Milford Mass.), and substrates and products were monitored by UV absorbance at 254 or 259 nm. Substrates and products were separated on a C18, 5 µm 250×4.6 mm HPLC column (Higgins Analytical, Mountain View, Calif.), using 15 mM ammonium acetate pH 6.0 solution, with a 0% to 10% (or 20%) methanol gradient. The products and substrate were quantified according to the integration of their correspondent peaks and the formula:

$$[product/substrate] = \frac{area_{product/substrate} / \varepsilon_{product/substrate}}{area, ... / \varepsilon, ... + area, ... / \varepsilon, ...} [substrate]_0$$

where [substrate]$_0$ is the initial substrate concentration. The extinction coefficients of AMP, ADP and ATP used in the formula were 15.4 mM$^{-1}$ cm$^{-1}$. If monitoring at 254 nm, substrate and product standards run on the same day as the reactions were used to convert integrated product/substrate peak areas to concentrations.

Mouse Models

TTW mice were discovered in brother-sister mating of Institute of Cancer Research strain mice (ICR, Japan), and develop multiple progressive abnormal calcifications and finally succumb to severe deformation and ankylosis. These mice serve as an established animal model of both OPLL and osteoarthritis because of specific spinal and joint abnormalities. The genetic defect accounting for the ectopic tissue mineralization phenotype has been traced to a premature stop codon in NPP1 at position 568 (glycine to stop), which truncates NPP1 by approximately 350 amino acids. A variant of the TTW mouse—C57BL/6J-Enpp1$^{asj}$/Grsr, or NPP1$^{asj}$ mice—has a point mutation in the NPP1 protein coding region at exon 7, position 737, which results in a valine to an alanine point mutation, and exhibit arthritis of the spine at 12 weeks, and osteoarthritis of many joints that become stiff and unbendable by 7 months of age. These mouse models are valuable reagents which mimic human diseases of ectopic calcification, including osteoarthritis, and are appropriate animal models to validate a hypothesis of the present study.

The therapeutic efficacy of recombinant NPP1 in two mouse models of ectopic calcification, both of which are variants of tip toe walking (ttw) mice, is explored. The first model is the original ttw mouse model described by Japanese researchers, which is available through the Central Institute for Experimental Animals in Japan. The mice have a spontaneous recessive mutation which predisposes the animals to a generalized ankylosis of the axial and appendicular skeleton starting at three weeks of age in the small distal joints of the hands and feet. Besides articular and vertebral disk cartilage, ttw mice also show calcification of vessels and connective tissues. After genetic mapping, the mutation responsible for the phenotype was identified as a truncation of NPP1 at position 568. The second mouse model, directly available from Jackson Laboratories, is named the C57BL/6J-Enpp1$^{asj}$/GrsJ mouse. These mice have a point mutation in the NPP1 protein coding region at exon 7, position 737, which results in a valine to an alanine point mutation, and exhibit arthritis of the spine at 12 weeks, and osteoarthritis of many joints which become stiff and unbendable by 7 months of age.

Establishment of NPP1 dosing levels

NPP1 intra-peritoneal (IP) dosing levels that normalize serum PPi concentrations in ttw mice are established. Initial pharmacokinetic experiments are performed to establish the appropriate route and concentration of NPP1 necessary to affect PPi levels in vivo. Wild type (C57bl/6) animals are dosed with a single dose of NPP1 (e.g., i.p., i.v., etc.) at concentrations beginning at 0.03 mg/kg. This initial concentration is chosen because physiologic NPP1 concentrations in human serum are quite low (between 100-300 pM). A concentration of mammalian NPP1 of 2.15 mg/ml in an aqueous buffer is in close proximity to physiologic conditions (50 mM Tris pH 8.0, 150 mM NaCl, 0.8 mM ZnCl$_2$, 0.4 mM CaCl$_2$, 0.4 mM MgCl$_2$). For instance, a 40 gram mouse would be injected with about 0.5 µl of concentrated stock. NPP1 dosing is adjusted as necessary to arrive at dosing levels that directly affect serum PPi concentrations.

About three animals are dosed per experimental group. The animals are dosed at about 0, 0.5 mg/kg, 2 mg/kg, and 8.0 mg/kg concentrations to begin. Animals are sacrificed at about 1, 4, and 8 hours post treatment, and blood is collected by cardiac puncture following terminal anesthesia. Serum is isolated, and serum concentrations of PPi are directly measured using a commercially available fluorogenic pyrophosphate sensor that has its fluorescence intensity proportionally dependent upon the concentration of pyrophosphate (see Abcam product number ab112155). Serum pyrophosphate concentrations of dosed and undosed animals are compared to determine initial dosing levels of NPP1 that physiologically alter serum PPi values in mice.

Pharmacokinetic experiments with the ttw mice are undertaken once NPP1 dosing levels are established in the wild type mice. To start, NPP1 concentrations which modulate PPi levels in wild type mice are used. About three animals are used per experimental group, and the animals are dosed at about 0, 1X, and 10X levels, where X is the minimal NPP1 concentration observed to modulate serum PPi levels in wild type (c57bl/6) mice. Animals are sacrificed at about 1, 4, and 8 hours post treatment, blood is collected and PPi concentrations are analyzed as described elsewhere herein. The serum PPi levels of treated and untreated animals are compared with those of the wild type animals in experiments described elsewhere herein to establish the final beginning concentrations of NPP1 to be used in the efficacy experiments.

Efficacy of Recombinant NPP1 in Mouse Models of Ectopic Calcification

TTW and C57BL/6J-Enpp1$^{asj}$/GrsJ mice are used to determine the effect of recombinant NPP1 on mouse models of ectopic calcification, as described elsewhere herein. Four breeding pairs are established to develop each genetic colony. Because the onset of progressive physical disability impairs the ability of homozygous females to maintain a litter, heterozygous females are bred with homozygous males. The animals are genotyped by Yale Animal Resource Center at three weeks of age, and once weaned the animals are separated into cages according to their genotypes and ages. Strict record keeping is maintained to ensure animals are correctly identified prior to experimentation. At 6 weeks of age the mice are separated into cohorts of about 6 mice and are treated with increasing concentrations of NPP1, beginning at the lowest concentrations observed to normalize serum PPi concentrations, as described elsewhere herein.

The development of symptoms is compared between treated and untreated animals, with attention paid to the following phenotypes:

Gait: A slow, hobbling gait in the C57BL/6J-Enpp1$^{asj}$/GrsJ mice occurs at around 2 months of age. TTW mice also develop abnormal gait, rigidity of the vertebral column, and stiffness of the limb joints at about 2 months of age.

Abnormal Resting Posture: C57BL/6J-Enpp1$^{asj}$/GrsJ mice develop a stiff posture with the front legs held in toward the body by about 2 months of age. TTW mice also develop stiffness of the limb joints at about 2 months.

Skeleton Phenotype: C57BL/6J-Enpp1$^{asj}$/GrsJ mice develop hyperplastic joint spaces in the knees and elbows at about 11 weeks, arthritis of the spine at about 12 weeks, and osteoarthritis in many joints at about 12 weeks. By about 7 months, the joints of C57BL/6J-Enpp1$^{asj}$/GrsJ mice become stiff and unbendable. TTW mice develop rigidity of the vertebral column, and generalizing ankylosis of the axial and appendicular skeleton starting at about 3 weeks of age.

Osteoartheritis: Osteoartheritis is found in both ttw and C57BL/6J-Enpp1$^{asj}$/GrsJ mice at approximately 12 weeks of age.

Hearing Loss: Auditory brainstem response shows severe hearing loss in C57BL/6J-Enpp1$^{asj}$/GrsJ mice by about 3 months of age.

Imaging studies: Sites of active mineralization in mice and man may be observed with radionucleotide scans utilizing various agents, including by not limited to Tc99m-pyrophosphate. Increased Tc99m-pyrophosphate may be seen in animals with increased mineralization. Radionucleotide imaging scans are performed on the animals at day 0, 7, and 14, of treatment by subclavian injection of the radiolabelled tracer. Increases in PPi deposition are correlated with NPP1 dosing levels. In certain embodiments, PPi deposition increases in NPP1 mutant animals at the lowest concentration levels of recombinant NPP1 or NPP4 enzyme, but therapeutic levels of recombinant NPP1 or NPP4 reduce or eliminate PPi deposition as observed in radionucleotide scans.

At least one of the above phenotypes are monitored and/or quantified in the treated and untreated animals by recording the gait of animals on treadmills to follow gait and posture, imaging studies to follow in vivo skeletal changes during the course of the experiment, auditory assessment of the mice to document hearing loss, and histologic examination of the skeleton and soft tissues of the mice at the conclusion of the experiment to document ectopic calcification and skeletal abnormalities. MRI imaging is used to follow the extent of soft tissue mineralization and skeletal abnormalities in the animals during the course of the experiment. Prior to imaging, the mice are anesthetized with isofluorane in an anesthesia chamber, and then transferred to an IVIS imager box during the imaging process. The mice are maintained under anesthesia via nose cones that are present in the MRI imager box during the imaging process. The animals are observed for about 30 minutes post procedure for signs of pain and distress following reversal of anesthesia. Mice require 1-2 minutes to recover from the anesthesia, and that the mice can be safely imaged 2-3 times per week for up to 1 month without health sequella. Mice are periodically recorded on mechanized treadmills in order to observe and analyze their gait and the presence of postural changes. Auditory brain response and the lick suppression test are used to monitor hearing loss in the animals, and tissue and bone histology is used to document the presence of soft tissue calcification and bone abnormalities.

As described elsewhere herein, steps are taken to minimize immune reaction to the recombinant human NPP1 in the immunocompetent ttw mice. In the event that unexpected decreases in serum PPi concentrations are observed, which are consistent with a reduced NPP1 half-life suggestive of immune mediated destruction of the protein, standard approaches of immune-tolerization can be used, such as those which have been used in mice to generate monoclonal antibodies specific to alternate protein isoforms (Matthew et al., 2987, J. Immuno. Methods 100:73-82; Salata et al., 1992, Anal. Biochem. 207:142-149). These procedures involve immunizing the animals with cyclophosphamide concurrent with the initial dose of NPP1 protein, which can tolerize the animal to the human isoform. If tolerization is unsuccessful, the mouse isoform of NPP1 is cloned and expressed in an identical manner to that described for the human, and the mouse isoform of the protein is used to conduct the described experiments. Either of these alternative procedures provides a method of treating mice with NPP1 in a manner that will not induce an immunologic response, thereby achieving stable, efficacious NPP1 concentrations sufficient to delay or reverse the ectopic mineralization characterizing their genetic disease.

Crystallization, Data Collection and Processing, Structure Determination

NPP4 was exchanged into 50 mM Tris pH 8.0, 150 mM NaCl, 0.8 mM $ZnCl_2$, 0.4 mM $CaCl_2$, 0.4 mM $MgCl_2$), and protein concentrations were calculated using $A_{280}$. The best diffracting crystals were obtained via hanging drop method by mixing 6 mg/ml (0.14 mM) of NPP4 with well solution (200 mM ammonium citrate dibasic, 17.5% to 19.5% (w/v) PEG 3350) in a 1:1 ratio and suspending 2 µl drops over 600 µl of the well solution in a sealed chamber. Protein crystals typically appeared within 4 to 6 days and continued to grow slowly for the next week, reaching final dimensions of up to 500 um×150 um×50 um. Cryoprotection was achieved by quickly passing the crystals through a series of mixtures consisting of the above well solution with 0.6 mM $ZnCl_2$, 5 mM ligand (if present), and 5% (v/v) increments of glycerol up to a final concentration of 20% to 25%, then immediately flash-freezing in liquid nitrogen. Apo crystals of NPP4 were difficult to obtain, hampering efforts to obtain structures of NPP4 with ligands via soaking. Cocrystallization with ATP or a cleavable ATP-analogue (Sigma M7510) resulted in an AMP product complex, reflecting slow hydrolysis during crystallization. Cocrystallization attempts with a non-cleavable ATP-analogue (Sigma M6517) showed no visible binding.

Synchrotron diffraction data reported herein were collected at APS (Argonne National Laboratory, Advanced Photon Source, NE-CAT beamlines ID-24-C and ID-24-E), and at CHESS (Cornell High Energy Synchrotron Source, beamline A1). HKL2000 was used for indexing and reduction of the NPP4-AMP diffraction data. Initial phases were obtained via molecular replacement using PHENIX AutoMR and AutoBuild with a search model consisting of the protein-only portion of the *Xanthomonas axonopodis* NPP (2GSU) (Zalatan et al., 2006, Biochem. 45:9788-9803). COOT was employed for model building and the high quality of initial electron density maps allowed for unambiguous correction of areas of the structure that were originally problematic or out of sequence. PHENIX was used for iterative rounds of maximum likelihood refinement during which ligand, waters and several glycosylations were built in. Apo NPP4 and all subsequent structures were solved as above, but using the protein-only portion of the NPP4-AMP complex as the starting point. Unbiased electron density maps in which the local atoms were excluded from map calculations (omit maps) were used to systematically check each entire structure. Atomic positions for all residues 24 to 402 were determined. Flanking residues at the termini remain disordered. Statistics for diffraction data the final structures are illustrated in Table 1. The structures of human NPP4-AMP at 1.54 Å resolution (4LQY) and apo NPP4 at 1.50 Å resolution (4LR2) have been deposited in the Protein Data Bank.

Molecular Modeling of NPP1:ATP Complex

Mouse NPP1 (rcsb code 4B56) was loaded in MOE (Molecular Operating Environment, Chemical Computing Group Inc., Montreal, Canada) and the A-chain deleted and B chain retained with residues K169-E905. Asparagine-linked glycosylation sites were clipped and capped with methyl groups. Waters were deleted and atom types fixed and protonated with Protonate 3D. Zinc ions were restrained with respect to their ligand distance and geometry. The metal charge was modeled at +1. ATP was manually positioned by placing the adenine nucleus between the cleft formed from phenylalanine 239 and tyrosine 322 with the phosphate portion in an extended conformation along the large channel moving up the protein. The protein was tethered at a distance of 4.5 angstroms from the ligand and minimization performed on the entire system using AMBER12 with Extended Huckel Treatment of the ligand (AMBER12:EHT).

Molecular modeling of NPP4:ATP complex

NPP4 was modeled in a manner similar to NPP1 including glycosyl stripping and capping and placement of ATP. The corresponding residues in NPP4 for placement of the adenine are phenylalanine 71 and tyrosine 154. Protein protonation, tethering and minimization was performed in an analogous fashion, using the AMBER12:EHT forcefield treatment.

Enzymology

The steady state enzymatic activity of human NPP1 and NPP4 were determined by either absorbance (Ap3A substrate) or HPLC (ATP substrate). The affinities of nucleotide monophosphates (NMP) for NPP4 were estimated from the [NMP] dependence of steady state pNP-TMP (p-nitrophenyl 5' thymidine monophosphate) cleavage rates as monitored by the absorbance change at 405 nm (Saunders et al., 2008, Mol. Cancer Ther. 7:3352-3362). The [NPP4] was 5 nM and the [pNP-TMP] was 20 mM. The $IC_{50}$ value (i.e. nucleotide concentration exhibiting half maximal activity) was determined from the best fit of the nucleotide concentration dependent NPP4 cleavage activity to a rectangular hyperbola. The $IC_{50}$ reflects the weighted average affinity for mixed inhibition (Saunders et al., 2008, Mol. Cancer Ther. 7:3352-3362).

Preparation of Human Platelets and Platelet Aggregometry

Preparation of platelets and platelet aggregometry were performed as described in Albright et al., 2012, Blood 120:4432-4440.

Example 1: Enzyme Replacement Therapy for Idiopathic Infantile Arterial Calcification (IIAC) and Ossification of the Posterior Longitudinal Ligament (OPLL)

As described herein, a soluble form of the nucleotide pyrophosphatase/phosphodiesterase-1 (NPP-1) and mutant NPP-4 has been developed, which can be a useful therapeutic for diseases and disorders involving pathological calcification and/or ossification. Also described herein is a direct demonstration of the physiologic activity of the enzyme in disease states of NPP1 dysfunction, thereby establishing the utility of NPP1 enzyme replacement therapy in select disorders of ectopic calcification.

To develop a soluble form of NPP1, the sequences of NPP2 were combined with the sequences of NPP1 to obtain a soluble, secreted NPP1 protein. It was discovered that soluble, active, recombinant NPP1 could be produced by swapping the membrane-spanning domain of NPP2 into the homologous region of NPP1. Using such a construct, some variant forms of NPP1 occurring in OPLL and IIAC have been cloned and expressed. In some embodiments, NPP1 can be made to be soluble by removing the entire transmembrane domain of the protein.

Soluble, fully active forms of NPP1, and mutant NPP4 engineered to change the specificity of NPP4 from Ap3A to ATP, are useful protein therapeutics in OPLL, IIAC, and other diseases resulting from improper PPi balance. Specifically, the protein construct is comprised of the soluble domain of NPP1, the constant region of human IgG Fc domain (Fc), and about ten or more sequential Aspartic acid residues designed to target the protein to the bone.

These constructs yield soluble forms of NPP1 and mutant NPP4 at high yields, resulting in large quantities of soluble, pure, recombinant, enzymatically active NPP1 and mutant NPP4 capable of hydrolyzing ATP into AMP and PPi. These constructs may be useful in treating human diseases and disorders with improper PPi balance which are also associated with SNPs in NPP1.

The structure of NPP1 was modeled using the high resolution structure of NPP4 which had been previously determined, and it was discovered that many of the SNPs associated with the diseases described elsewhere herein map to the active site of NPP1.

Although not wishing to be bound by any particular theory, the data described herein are consistent with the explanation that reduced NPP1 activity is responsible for disrupting PPi/Pi homeostasis in many of the disorders described elsewhere herein, and that restoring PPi balance through the use of soluble, recombinant, NPP1 protein ameliorates the skeletal and joint abnormalities and ectopic tissue mineralization seen in these diseases.

OPLL is examined using standard animal models of the human disease with so called 'tip-toe walking' (ttw) mice. These mice develop progressive abnormal calcifications of the spine and joints that bear a striking resemblance to OPLL disease in humans, and eventually succumb to severe spinal deformations and ankylosis. The genetic defect of this spontaneously occurring mutation introduces a missense mutation into the coding region of NPP1 at position 568, prematurely truncating the protein. These mice are the accepted animal model for OPLL.

Dosing routes and concentrations of recombinant NPP1 in these mice which normalize their serum PPi concentrations are established, and whether these doses are able to defer, ameliorate, or reverse the signs and/or symptoms of the severe phenotype experienced by these animals is tested. NPP1 is examined as a protein therapeutic for animal models of ectopic tissue mineralization, including OPLL and osteoarthritis. The efficacy of recombinant NPP1 in diseases of ectopic tissue calcification is established by measuring the rate of joint and spine calcification in tip-toe walking (ttw) mice treated with recombinant NPP1 protein.

The appropriate NPP1 dosing necessary to normalize PPi levels is established by dosing ttw and wild type (c57bl/6, the genetic background) mice with increasing NPP1 concentrations and measuring the serum PPi concentrations in treated and untreated animals using established methods of PPi determination. The efficacy of recombinant NPP1 in diseases of ectopic calcification is determined by treating ttw mice with recombinant NPP1 and comparing the development of symptoms associated with ectopic tissue calcification between the treated and untreated animals.

Example 2: Substrate Discrimination of NPP4 Vs. NPP1

To determine the extent of substrate discrimination exhibited by highly homologous NPP family members, the steady state enzymatic rate of human NPP4 and NPP1 for their putative in vivo substrates, Ap3A and ATP, respectively, was measured (FIGS. 5A-5E). Human NPP4 shares 40% sequence identity with NPP1 throughout the catalytic domain, and the structure of mouse NPP1 has been determined (Jansen et al., 2012, Structure 20:1948-1959), providing the opportunity to identify the structural origins of substrate discrimination at the atomic level. Human and mouse NPP1 are 79% identical, with sequence mapping of the human sequence onto the mouse NPP1 structure showing that all sequence differences are outside the substrate binding and active sites. NPP4 and NPP1 hydrolyze Ap3A with comparable maximum turnover numbers ($k_{cat}$~7-8 s$^{-1}$), although the Michaelis constant of NPP1 is >30 times tighter than that of NPP4. In contrast, the rate at which NPP4 hydrolyzes ATP to AMP and PPi is negligible compared to hydrolysis by NPP1.

Example 3: Structural Overview

Figure 6A:
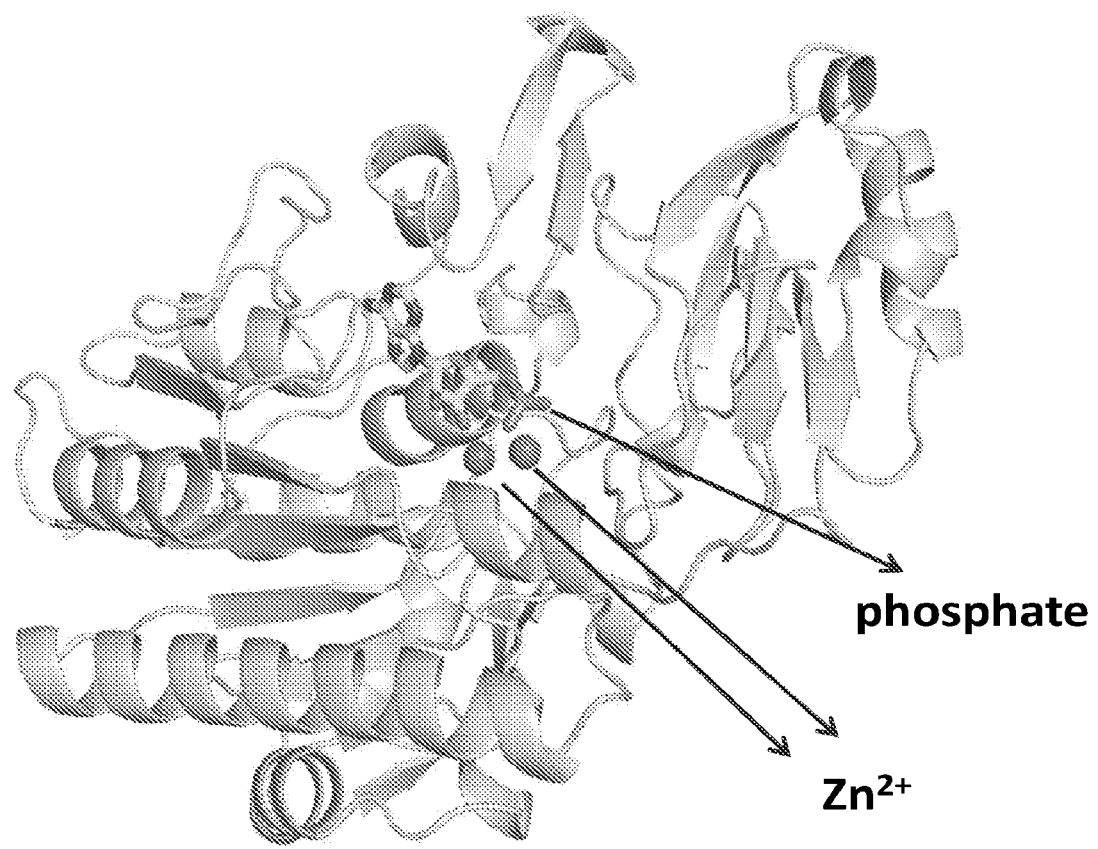
FIG. 6A-6C are a series of illustrations relating to NPP4-AMP structure and comparison to other NPP catalytic domains. The three dimensional structure of NPP4 with enzymatic product (AMP) bound was determined to 1.5 Å resolution by X-ray crystallography.

In order to understand the molecular basis of NPP4 substrate specificity and to achieve detailed insights regarding its similarities and differences relative to NPP1, X-ray crystallography was utilized to determine the high-resolution three-dimensional structures of human NPP4 in both apo and AMP-bound forms, at 1.50 Å and 1.54 Å resolution, respectively (Table 1 and FIG. 6A). These were then compared to recently determined structures of mouse NPP1 complexes, including mNPP1-AMP at 2.70 Å resolution, in order to define structural features responsible for the observed substrate specificities of each. The bimetallo catalytic domains of NPP4 and NPP1 contain two bound zinc ions, and share a similar overall fold and employ a conserved catalytic mechanism to hydrolyze at the same position on substrates, resulting in a nucleotide monophosphate product. Hydrolysis of Ap3A or ATP by either of these enzymes yields an AMP product molecule. Accordingly, hNPP4-AMP and mNPP1-AMP structures are product-complexes. Superposition of the entire catalytic domain of NPP4 with that of NPP1, NPP2 and the bacterial NPP yield rmsd values of 1.54 Å, 1.43 Å and 1.43 Å, respectively. The structural features observed in NPP4 that favor nucleotide binding are largely conserved in the bacterial enzyme.

Figure 6B:
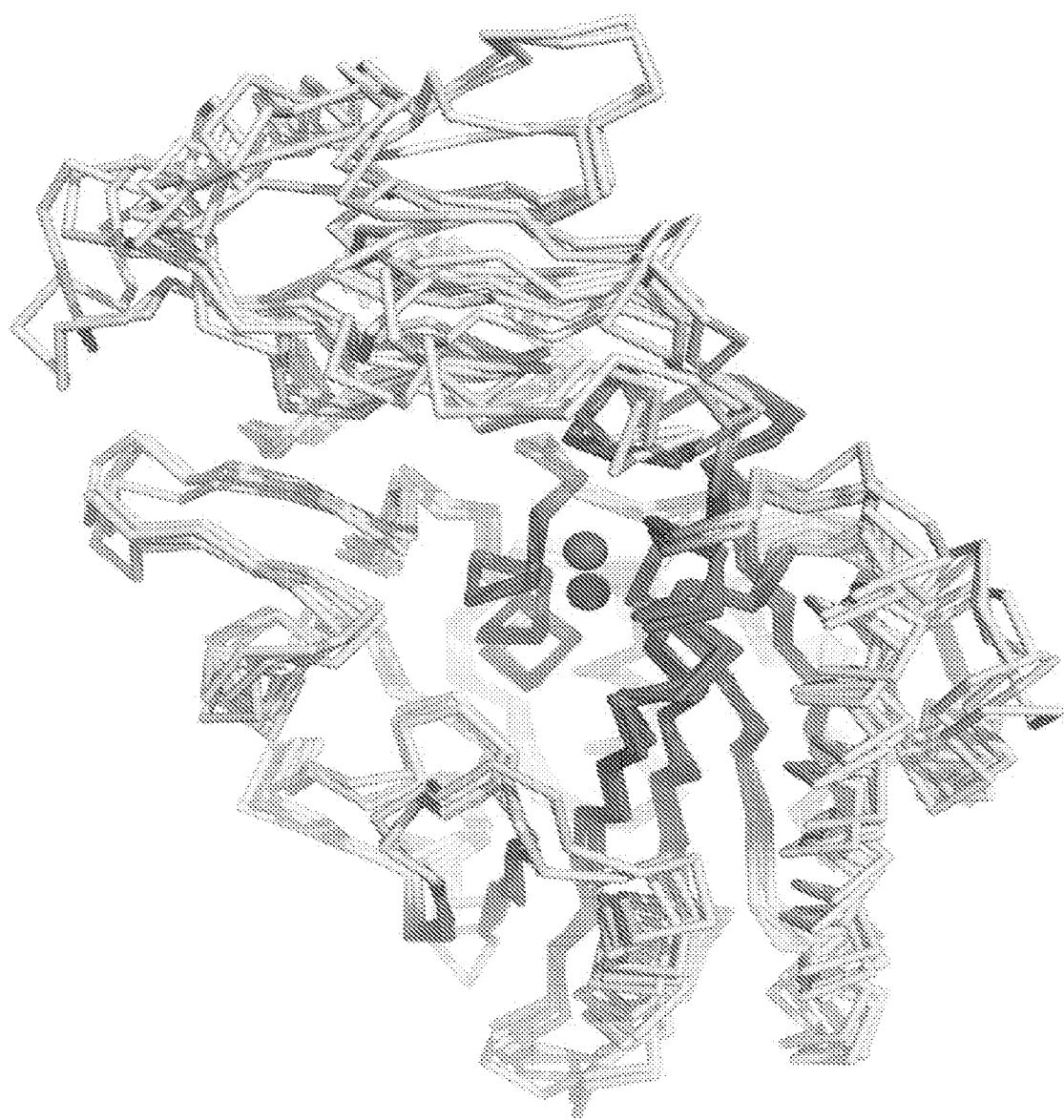
Figure 6C:
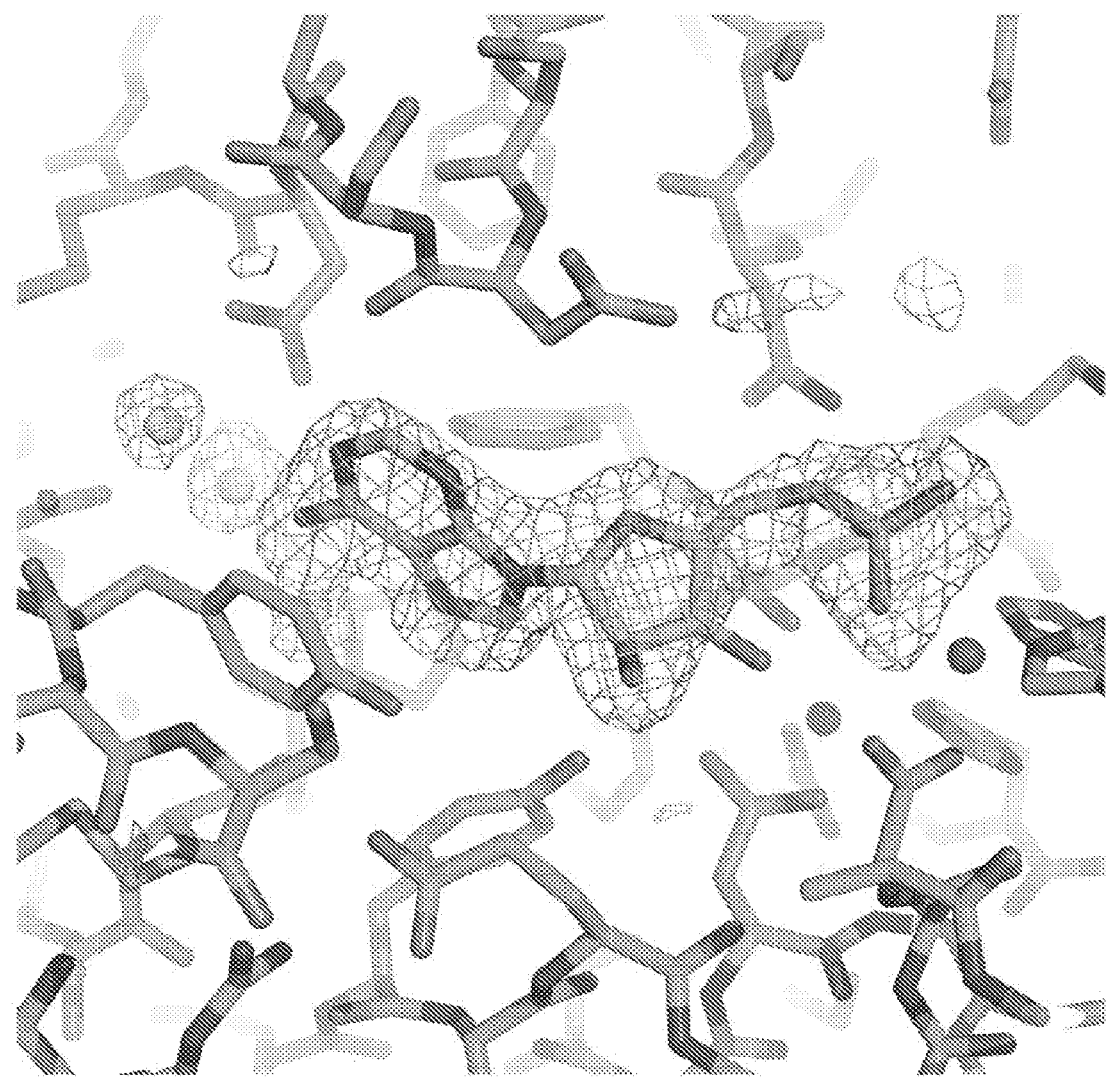

NPP4 is a monomeric enzyme with a binding pocket that remains essentially unchanged in the presence or absence of bound product. Disulfide bonds link residues 254 to 287 and 394 to 401, and three N-linked glycosylations are observed at asparagine residues 155, 166 and 386. Due to location, these glycosylations are not likely to significantly impact enzymatic activity. This is the first human NPP structure to be determined and shares an overall common fold with the catalytic domains of all other structurally determined NPPs (FIG. 6B).

Example 4: Substrate Recognition and Active Site Geometry

Figure 7A:
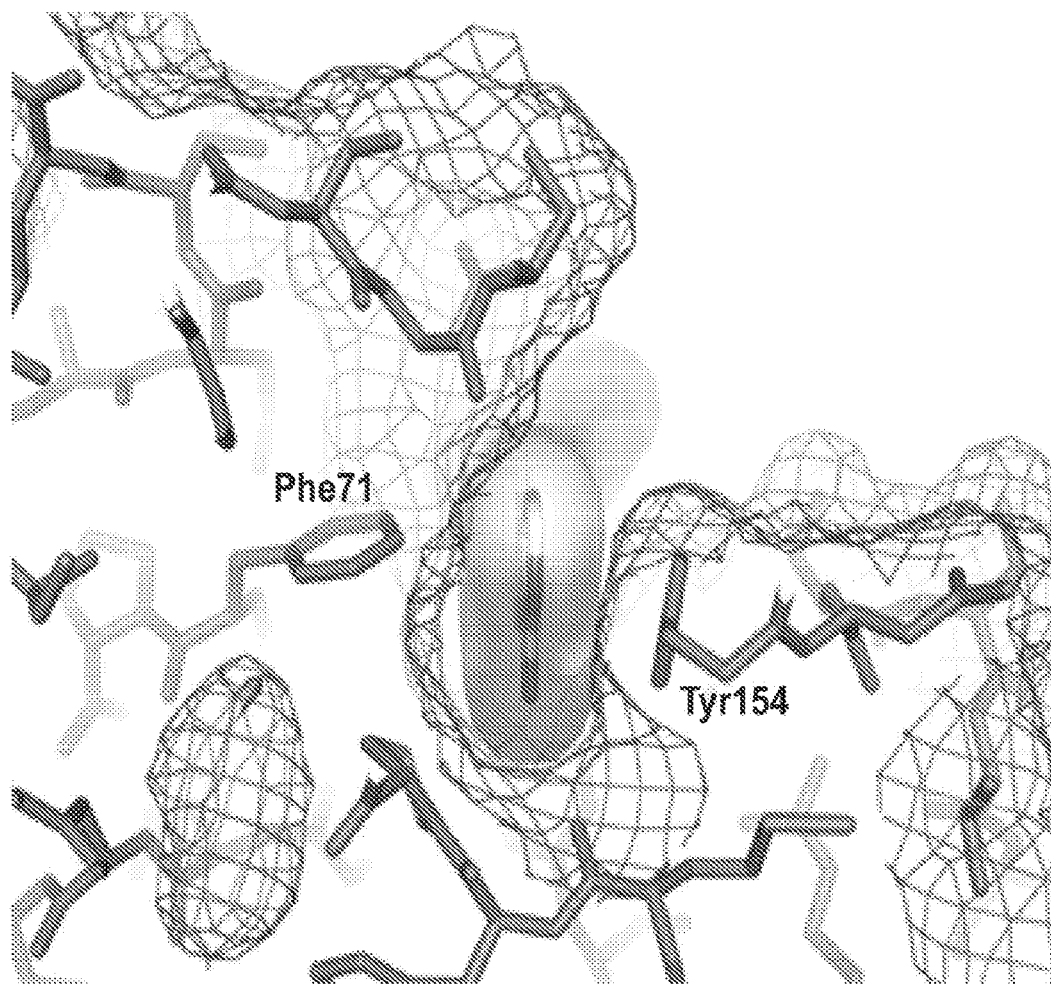
FIGS. 7A-7D illustrate the base recognition of substrate at the NPP4 catalytic site.
Figure 7B:
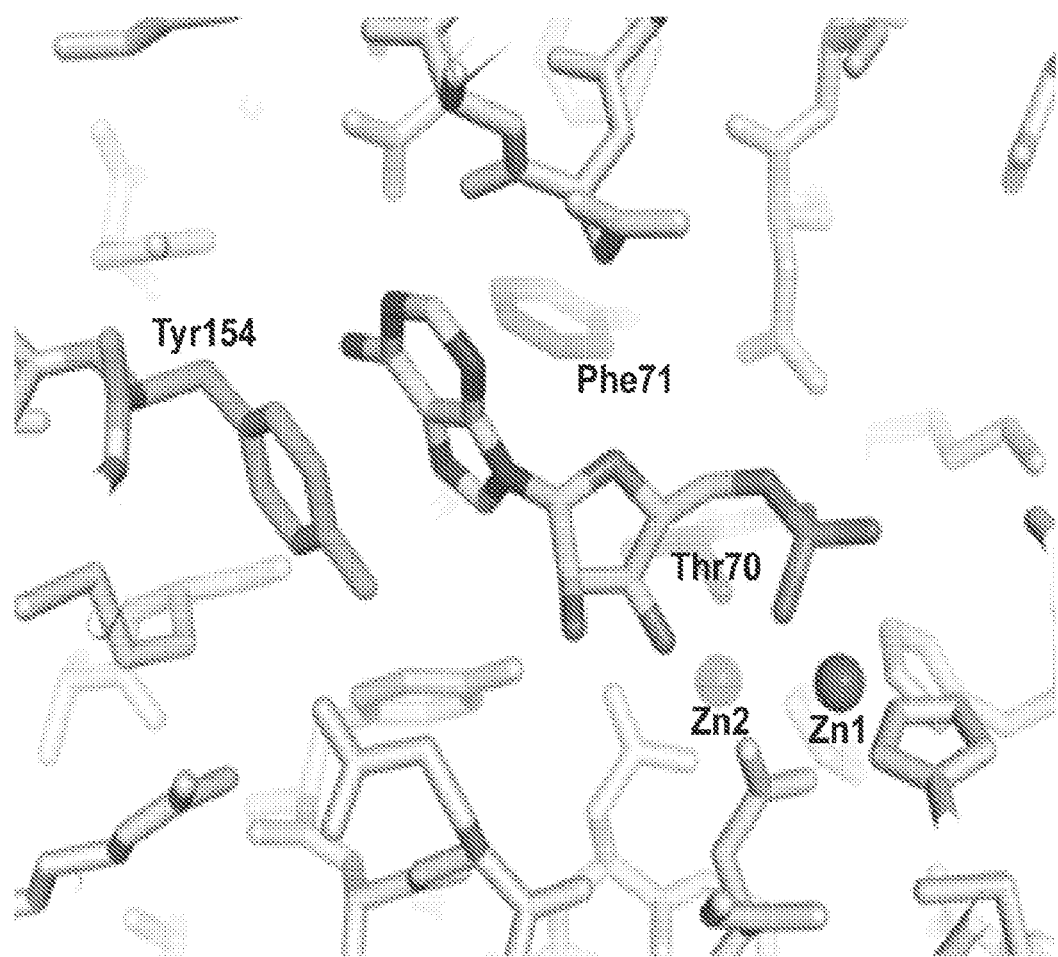

NPP4 targets phosphodiester substrates with a 5'-nucleotide group on the end, displaying the greatest preference for adenine rings. This specificity for nucleotide-containing substrates is the result of a pre-formed hydrophobic slot on the protein surface, approximately 6.8 Å wide, consisting of the ring face of Tyr154 on one side and the tip of Phe71 on the other (FIGS. 7A-7B). A nucleotide base bound within experiences favorable π-π stacking interactions with the tyrosine ring and van der Waals (VDW) interactions with the phenylalanine, sitting about 3.4 Å from each. The back wall of the slot lies just beyond the reach of the nucleotide base, precluding any direct hydrogen bonding interactions with the protein, and only a couple of water-mediated hydrogen bonds are observed between the edge of the AMP ring and NPP4.

Figure 5E:
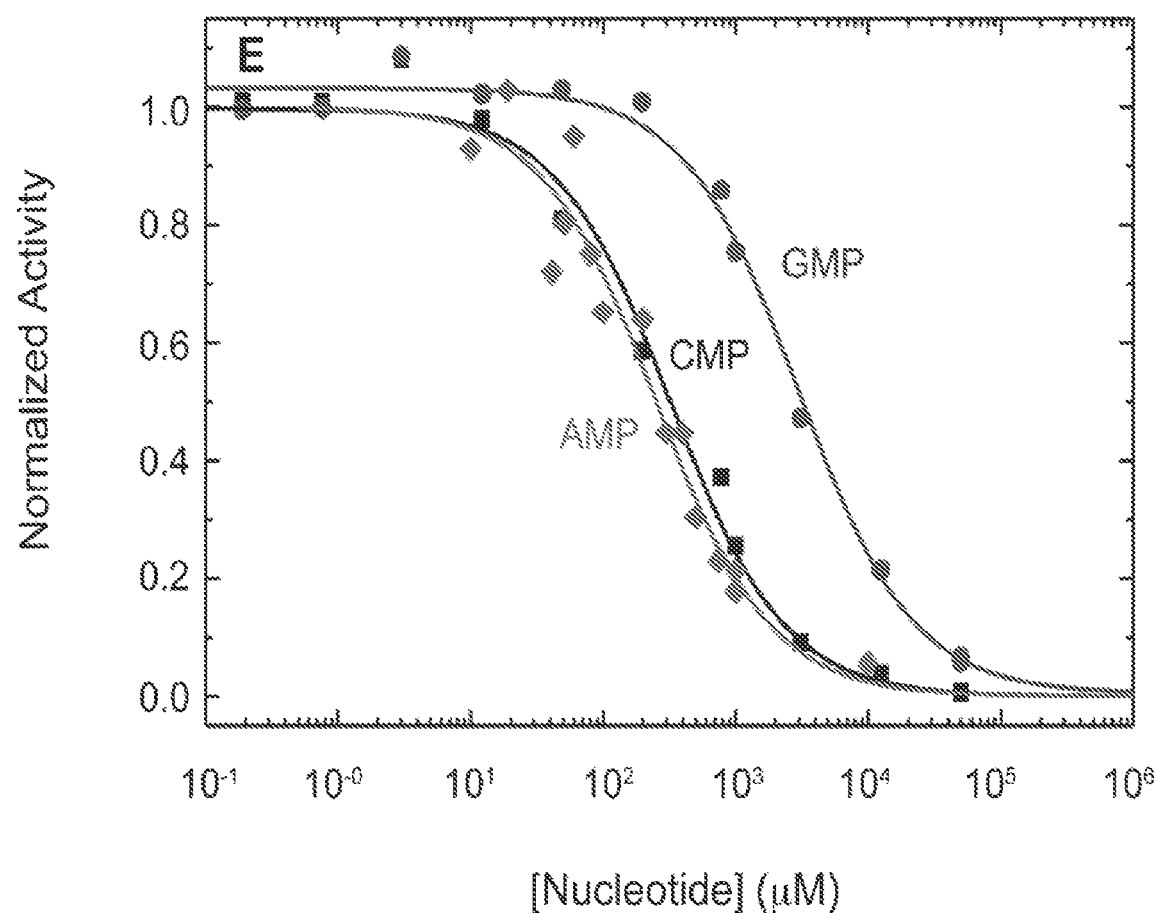

Although such a slot might be expected to favor purines over pyrimidines by virtue of their greater size, this pattern does not strictly hold. The relative affinities of nucleotide monophosphates for NPP4, as determined by TMP-pNP substrate inhibition, are: AMP>CMP>UMP>GMP (FIG. 5E). Corresponding measurements reported for NPP1, another family member with a similar nucleotide slot, reveal: AMP>CMP>GMP>UMP (Kato et al., 2012, Proc. Natl. Acad. Sci. USA 109:16876-16881). The present model building reveals that the guanine ring N2 atom of a similarly-bound GMP would experience some steric clash with NPP4 at residues 104 and 105, which slightly overhang the nucleotide slot. Upon inspection of the NPP1-GMP cocrystal structure, a similar steric clash was discovered, forcing the guanine ring to rotate slightly.

Immediately adjacent to the hydrophobic slot are two bound zinc ions, hereafter referred to as Zn1 and Zn2, held ~4.5 Å apart via interactions with six invariant residues found in all NPPs and alkaline phosphatases (APs). Both zinc ions display tetrahedral coordinate geometry. Zn1 is ligated by Asp189, His193 and His336, with a fourth coordination coming from a phosphate group oxygen atom in the NPP4-AMP complex. Alternatively, in an empty pocket this coordination can be provided by a water molecule. Zn2 is held by Asp34, Asp237 and His238, with a fourth coordination to the Oγ atom of Thr70, the "catalytic residue" of NPP4. This close association serves to activate Thr70 for nucleophilic attack on a substrate molecule, as described for APs, presumably by perturbing its pKa. Thr70 is located at the N-terminus of an α-helix pointing directly at the phosphate binding site near the semi-exposed Zn1, such that helix-dipole forces compliment the positively-charged zinc ions in electrostatically drawing the negatively-charged phosphodiester group into the active site. The narrow nucleotide slot and the short spacing between the slot and the zinc ions are primarily responsible for substrate selection, sterically favoring a 5'-nucleotide monophosphate group on the end.

By comparison, the other end of the NPP4 binding pocket appears relatively featureless and significantly more solvent-exposed, consistent with the ability of NPP4 to hydrolyze substrates of varying length and chemical character. No crystal structures of any NPP with intact substrate bound have been reported to date, however our substrate docking simulations indicate that the NPP4 binding pocket runs along the shallow groove on the protein surface.

Example 5: NPP4-AMP Vs. Apo NPP4

Figure 7C:
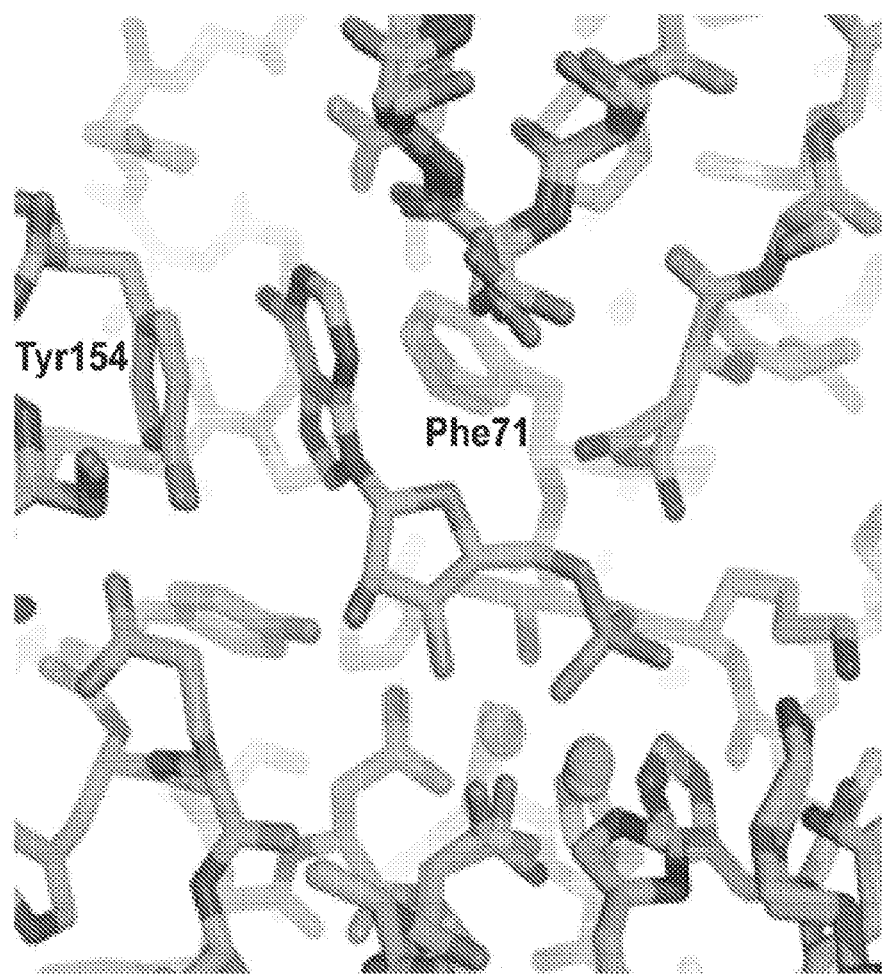

The apo structure of NPP4 is essentially identical to the AMP-bound structure (FIG. 7C). Since no changes are observed within the empty hydrophobic slot or at the catalytic residue, the binding site is pre-formed and appears to not undergo induced-fit adjustments upon substrate binding. The apo structure has a citrate anion, from the crystallization conditions, bound at Zn1 in a chelation-like interaction. Asn91 is the only active site residue that moves notably, pivoting to allow room for the citrate molecule. In the NPP4-AMP complex, Asn91 donates a hydrogen bond to the phosphate group bound near Zn1. The ability of Asn91 to pivot may allow it to maintain a hydrogen bonding interaction with the phosphate oxygen through the catalytic intermediates of the reaction, or allow flexibility to facilitate the entry or exit of a ligand.

Example 6: NPP4-AMP Vs. NPP1-AMP

Figure 7D:
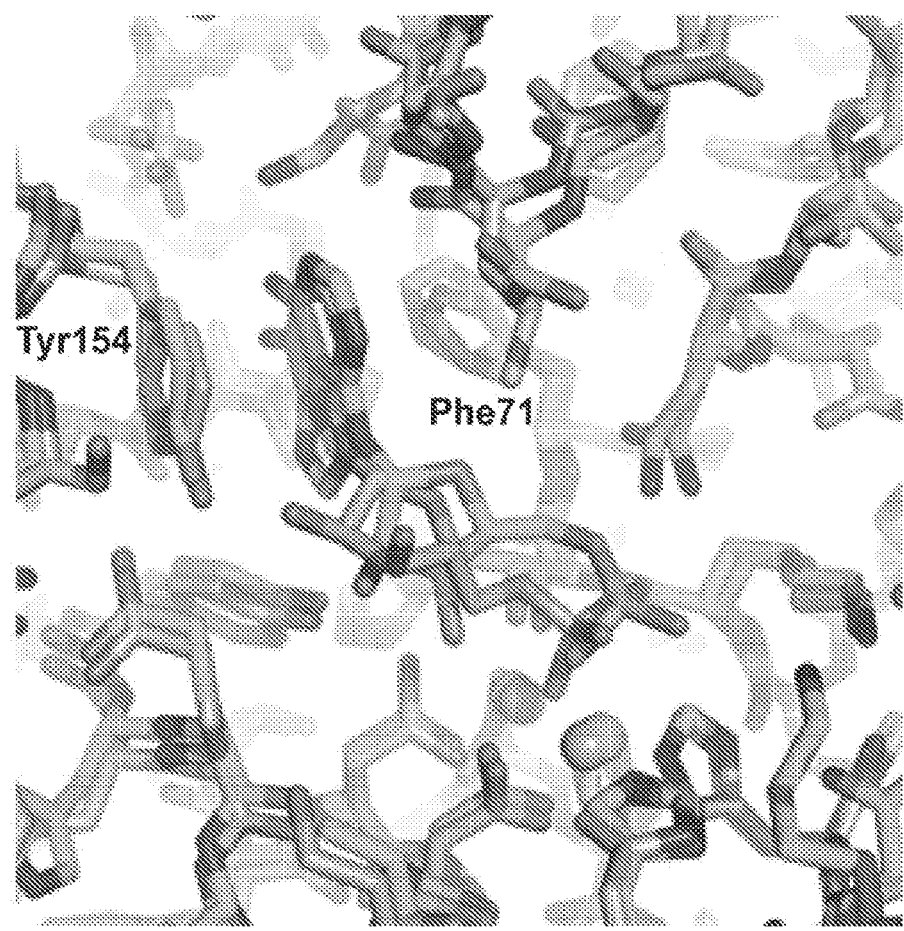

The overall similarity of how AMP binds within the slot region of NPP4 and NPP1 is illustrated in FIG. 7D. NPP1 contains conserved residues corresponding to Tyr154 and Phe71 of NPP4, therefore also targets substrates with a 5'-nucleotide end. The phosphate group of AMP binds near Zn1 in both enzymes. Whether the small differences observed in AMP position are real or simply reflect the significantly lower resolution of the NPP1-AMP structure (2.70 Å versus 1.54 Å for NPP4-AMP) is unknown.

Example 7: Catalytic Mechanism

Figure 8:
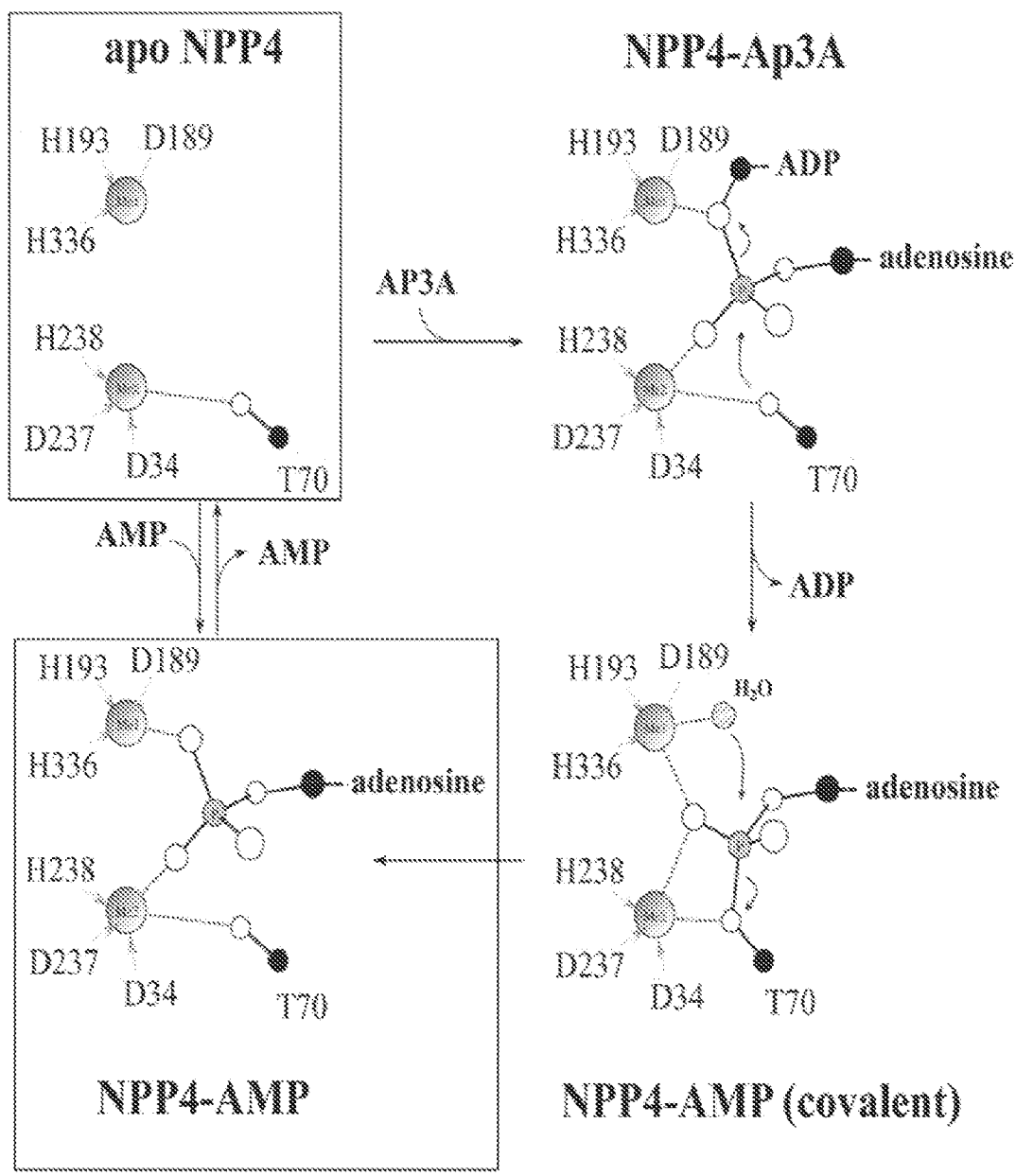
FIG. 8 is a scheme illustrating a non-limiting enzymatic mechanism of Ap3A hydrolysis by NPP4. Proposed reaction mechanism for NPP4 hydrolysis of Ap3A, based on active site homology to APs as originally proposed by Gijsbers et al. Boxes have been placed around the steps in the mechanism for which crystal structures have been obtained.

NPPs are members of the AP superfamily and share many of the key structural features, residues and architecture at the center of the active site where the catalysis occurs. FIG. 8 depicts a general reaction mechanism for NPPs as it applies to NPP4 hydrolysis of Ap3A, along with the corresponding crystal structures or binding simulation model for each step.

In NPP4, the relative spacing between the pre-formed hydrophobic slot and the two bound zinc ions dictates that it is the α-phosphate group of the substrate that is positioned adjacent to the Zn1 and Thr70, whose Oγ atom is perpetually activated for nucleophilic attack by its close proximity to Zn2. Upon Ap3A binding, the α-phosphate is attacked by Thr70, causing the ester bond on the opposite side to break, releasing ADP. A water molecule immediately enters the vacant space next to Zn1, becomes activated and attacks the α-phosphate from the opposite direction, causing the transient covalent NPP4-AMP bond to break, releasing AMP and restoring NPP4 to its original state. The release of the two product molecules is sequential, with the nucleotide monophosphate leaving last. As such, NPP4-AMP and NPP1-AMP are product-complexes.

Example 8: Molecular Determinants of Substrate Specificity of NPP4 and NPP1

Figure 9A:
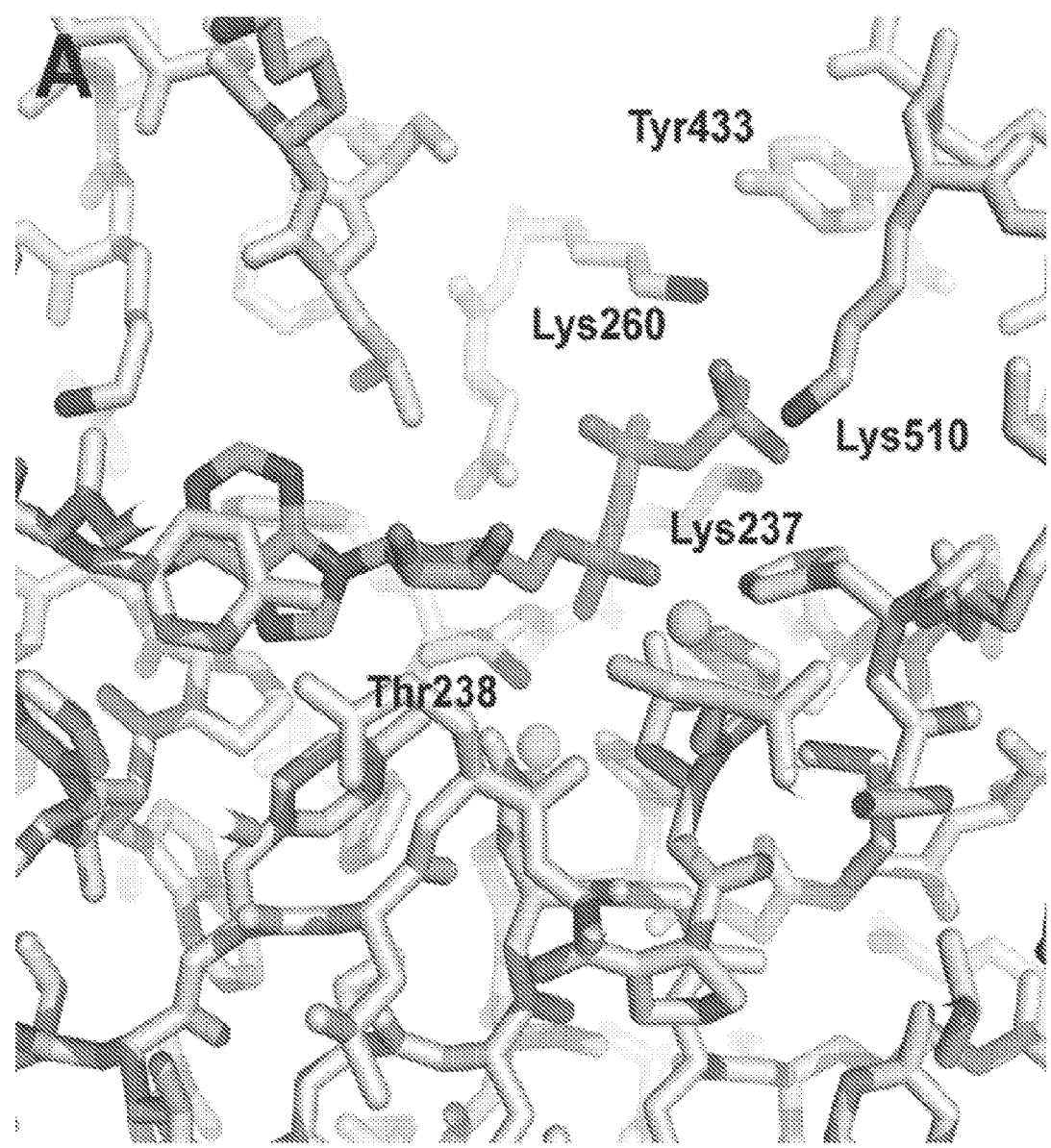

NPP1 readily cleaves ATP into AMP and PPi, whereas NPP4 does so only exceedingly slowly. Since both enzymes target nucleotide-containing substrates with a preference for adenine rings, and bind AMP in a similar fashion (FIG. 7D), the key to this deviation must lie elsewhere within the binding pocket. Since NPP1 efficiently hydrolyzes ATP into AMP and PPi, ATP likely binds NPP1 in the same orientation as is observed for AMP. ATP was thus modeled into the NPP1 active site by adding two phosphate groups to the NPP1-AMP cocrystal coordinates (4B56) (FIGS. 9A, 9C, 9E), then subjected the complex to energy minimization as described. Superposition of the binding sites of NPP1 with NPP4 reveals good overlap between most side chains within 4.5 Å of this ATP substrate, but with notable differences occurring near the terminal γ-phosphate. In NPP1, donation of Phe516 (mouse numbering) to the protein core creates more space for the γ-phosphate of ATP, which appears to be charge-stabilized by three lysine residues (Lys237, Lys260 and Lys510), which are referred to as a lysine claw. Two of these lysines (Lys260 and Lys510) line the upper edge of the binding pocket and remain disordered in the absence of a γ-phosphate, as is observed in NPP1-AMP structure. Ther simulation illustrates that, as new substrate enters the NPP1 binding site, these lysines should be electrostatically drawn to the γ-phosphate and become ordered in the process. The γ-phosphate of bound ATP appears to lie under an induced-fit lid comprised of Tyr433, Lys260 and Lys510, where it should be charge-stabilized by three lysines (FIG. 9A). Upon PPi product release, Lys260 and Lys510 should again become disordered until new substrate is drawn to the site.

Figure 9B:
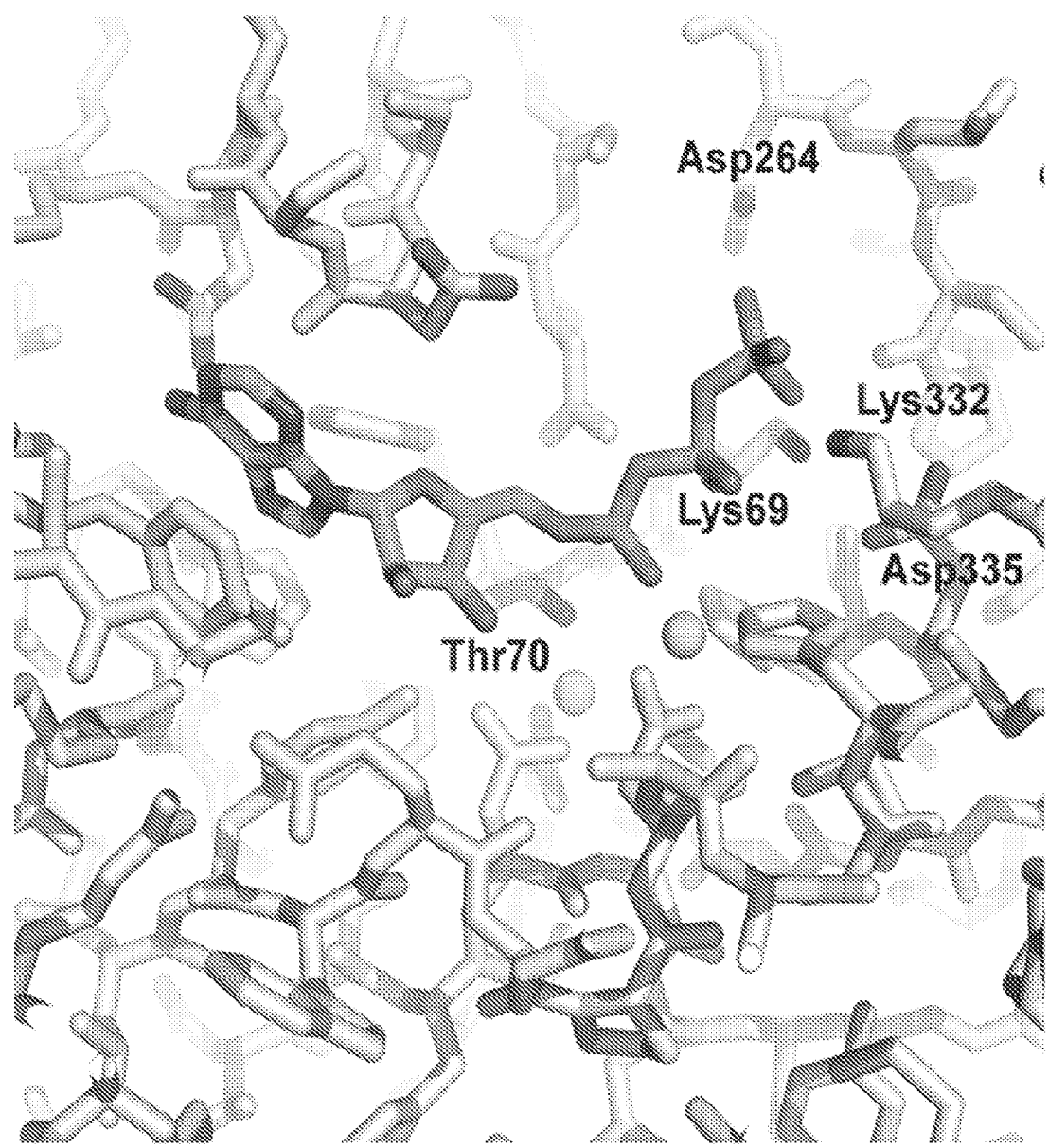
Figure 9E:
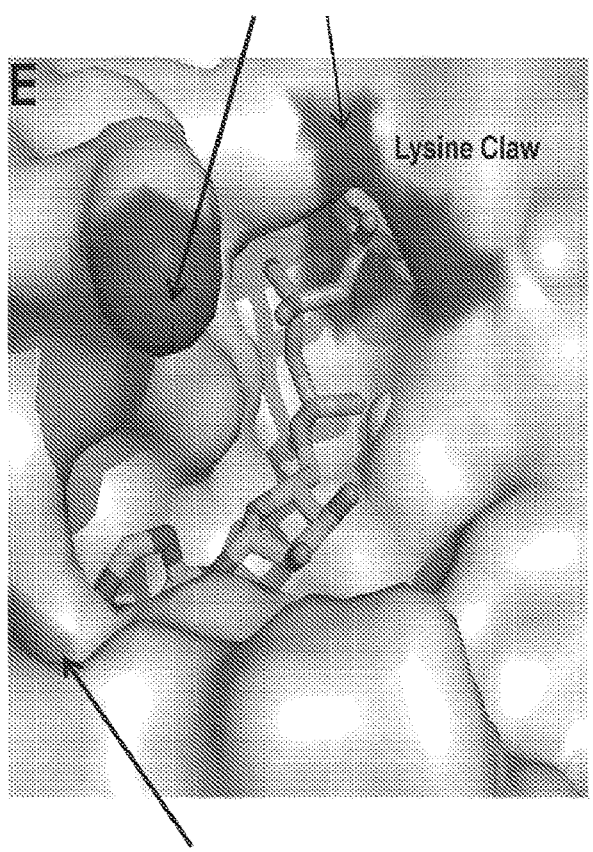
Figure 9F:
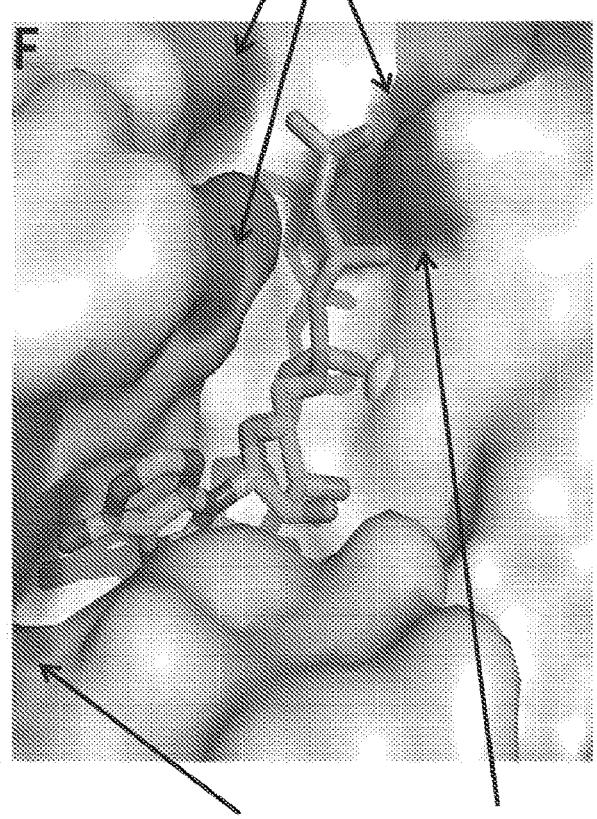

In a likewise manner, ATP was modeled into the NPP4 active site by adding two phosphates onto the NPP4-AMP structure, after which the complex was energy minimized. In contrast to NPP1, the region of NPP4 near the γ-phosphate is much more open and solvent-exposed, contains additional negatively-charged residues and fewer positively-charged ones, and has no ability to form lysine claw or a lid (FIGS. 9B, 9D and 9F). The γ-phosphate of ATP bound in this orientation would sit next to the negatively-charged Asp335, which corresponds to Phe516 of NPP1, but now points directly into the binding pocket. Asp264 (corresponding to Val 432, mouse NPP1) is also nearby. Overall, the local electrostatic environment of this region of the NPP4 binding pocket is significantly less favorable than in NPP1.

The ability to charge stabilize at this position may be more pronounced with ATP than with other substrates, such as Ap3A, since a terminal phosphate group (phosphomonoester) intrinsically carries more negative-charge than a non-terminal phosphate group (phosphodiester). As such, the terminal γ-phosphate of ATP carries more negative-charge than the corresponding in-line γ-phosphate of Ap3A. The highly effective charge-stabilization of NPP1 at this position is likely key to its ability to readily hydrolyze ATP, whereas the less-favorable local environment found at this same position in NPP4 is detrimental and hydrolysis occurs only very slowly.

Example 9: NPP1 and Platelet Aggregation

The hydrolysis of Ap3A by NPP1 raises the question of whether NPP1 may play a role in platelet aggregation under physiologic conditions. Given that the enzyme is active against Ap3A substrate, the relative abundance of NPP1 within the vascular space may determine the role of NPP1 in coagulation. NPP1 is reported to be present on brain capillary endothelium, but not on capillaries elsewhere. In addition, NPP1 is present on the membrane surfaces of plasma cells, osteoblasts, chondrocytes, and matrix vesicles (MVs) shed from osteoblasts and chondrocytes. NPP1 is also present as a soluble protein within the vasculature at very low concentrations of between 10-30 ng/mL (or 100-300 pM).

To determine the concentration of NPP1 capable of inducing platelet aggregation, increasing concentrations of NPP1 were titrated into platelet rich plasma (PRP) with physiologic levels of Ap3A. Addition of NPP1 to 80 uM Ap3A results in no platelet aggregation until the concentrations of NPP1 reach 1 nM (FIGS. 10A-10B). While this concentration is approximately 3-fold greater than the highest reported plasma concentrations of NPP1, this concentration is below the threshold required for NPP4 to trigger platelet aggregation (FIGS. 10A-10B), and well within the concentration range of membrane bound endothelial proteins. Plasma concentrations of NPP1 are thus unlikely to induce primary, platelet-mediated hemostasis in vivo, but that epithelial-bound NPP1 at anatomic locations where local concentrations exceed 1 nM are likely to induce significant platelet aggregation and thrombus formation.

Example 10: Ap3A Bound to NPP4

Human NPP4 (rcsb code 4LR2) was loaded in MOE (Molecular Operating Environment, Chemical Computing Group Inc., Montreal, Canada), and asparagine-linked glycosylation sites were clipped and capped with methyl groups. Waters were deleted and atom types fixed and protonated with Protonate 3D. Zinc ions were restrained with respect to their ligand distance and geometry. The metal charge was modeled at +1. Ap3A was manually positioned by placing the adenine nucleus between the cleft formed from phenylalanine 239 and tyrosine 322 with the phosphate portion in an extended conformation along the large channel moving up the protein. The remainder of the Ap3A molecule was left free in solution. The protein was tethered at a distance of 4.5 Å from the ligand and minimization performed on the entire system using AMBER12 with Extended Huckel Treatment of the ligand (AMBER12:EHT). The docked Ap3A molecule (FIG. 11) revealed the location of the second adenine binding site. This binding site was formed by a narrow groove in the protein surface, which in certain embodiments may be eliminated by the alteration of residues lining the surface of the pocket.

Example 11: Crystals of Ap3A Bound to NPP4

Figure 12:
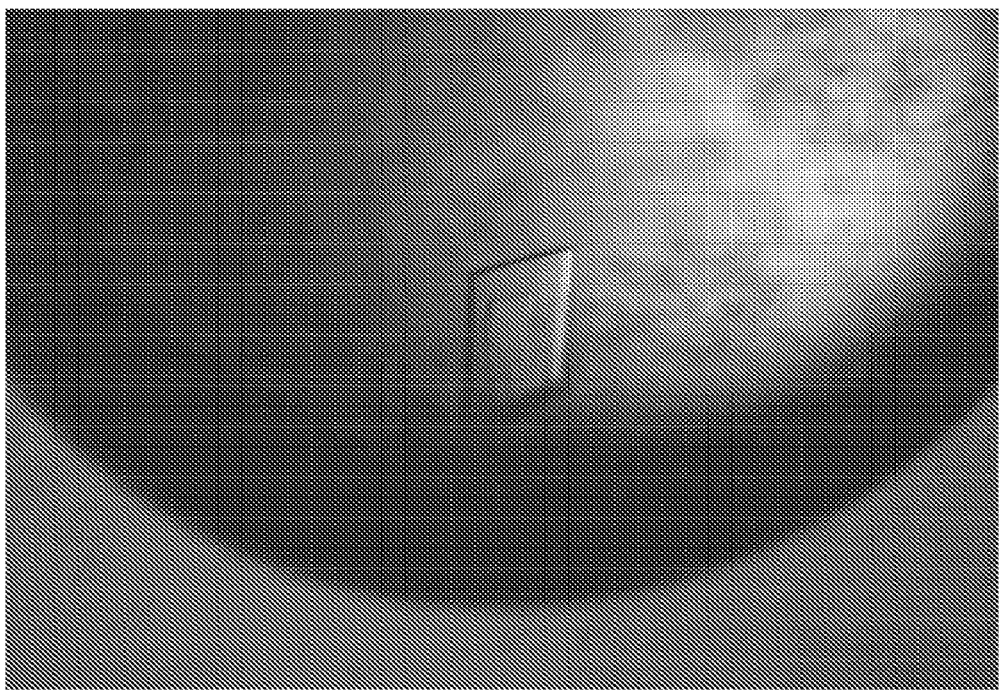
FIG. 12 is a set of photographs illustrating protein crystals comprising an inactive form of NPP4 bound to Ap3A.
Figure 12:
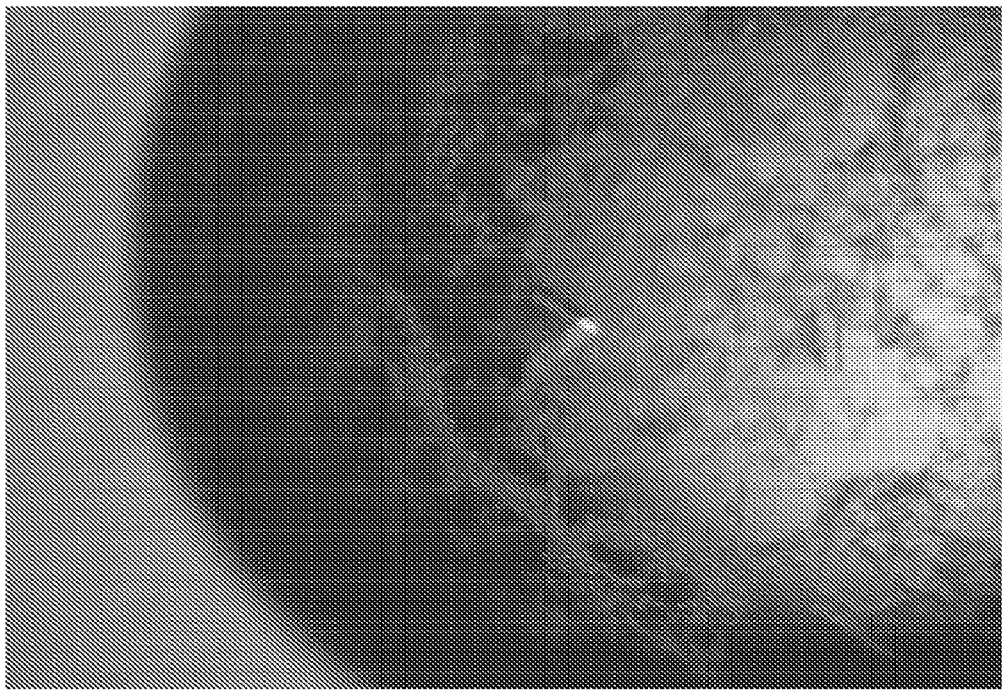

To directly determine the location of Ap3A in the NPP4 protein, an inactive mutant of NPP4 was crystallized with Ap3A (FIG. 12). This structure may be used to refine mutations of NPP4 and NPP1 designed to reduce the prothrombotic effects of the enzymes.

TABLE 1

Data collection and refinement statistics.

|  | NPP4-AMP | NPP4 apo |
|---|---|---|
| space group | C2 | C2 |
| a, b, c (Å) | 181.5, 51.1, 52.7 | 181.5, 51.3, 53.1 |
| α, β, γ (°) | 90, 102.4, 90 | 90, 102.1, 90 |
| resolution (Å) | 50-1.54 | 50-1.50 |
| beamline | APS/NE-CAT-C | CHESS/A1 |
| wavelength (Å) | 1.0750 | 0.9779 |
| Rsym(%) [a, b] | 6.0 (53.6) | 8.4 (54.8) |
| I/σI [a, c] | 724.9/35.6 (37.0/13.5) | 503.2/28.0 (19.0/7.0) |
| completeness (%) [a] | 99.2 (98.6) | 93.6 (60.2) |
| number of unique reflections | 69,525 | 71,681 |
| redundancy [a] | 4.0 (3.9) | 6.8 (5.0) |
| monomers/asu | 1 | 1 |
| number of non-hydrogen atoms: | | |
| protein | 3069 | 3069 |
| ligand (type) [d] | 23 (AMP) | 13 (FLC) |
| metal ions (zinc) | 2 | 2 |
| glycosylations | 56 | 56 |
| waters | 464 | 499 |
| Wilson B | 17.5 | 18.1 |
| average B for: | | |
| overall | 26.4 | 25.7 |
| macromolecule | 24.3 | 23.5 |
| ligand | 34.0 | 29.8 |
| solvent | 40.3 | 39.6 |
| Rwork/Rfree (%) [e, f] | 14.0/18.4 | 15.4/20.1 |
| rmsd bonds (Å) | 0.009 | 0.009 |
| rmsd angles (°) | 1.27 | 1.20 |
| Ramachandran plot (%): preferred or allowed/outliers | 99.7/0.3 | 99.5/0.5 |
| residue range | 24-402 | 24-402 |
| PDB ID code | 4LQY | 4LR2 |

[a] Values for the highest resolution bin are shown in parenthesis.
[b] $R_{sym} = \Sigma_{hkl} \Sigma_i |I_i(hkl) - <I(hkl)>|/\Sigma_{hkl} \Sigma_i I_i(hkl)$
[c] I/σI is the average intensity of reflections in thin resolution bins divided by the average standard deviation (sigma) of the same group of reflections.
[d] AMP is 5'-adenosine monophosphate. FLC is a citrate anion from the crystallization conditions.
[e] $R_{work} = \Sigma ||F_{(obs)}| - |F_{(calc)}||/\Sigma |F_{(obs)}|$
[f] $R_{free}$ = as for Rwork, but calculated for 5.0% of the total reflections that were chosen at random and omitted from refinement.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of reducing pathological calcification of vascular tissue in a human subject in need thereof, wherein said human subject has reduced ecto-nucleotide pyrophosphate/phosphodiesterase-1 (ENPP1) activity as determined by serum pyrophosphate levels in the subject relative to the serum pyrophosphate levels in a wild-type human,
wherein said method comprises administering to said subject a therapeutically effective amount of a soluble polypeptide an ENPP1 polypeptide catalytic domain, wherein said soluble polypeptide lacks a domain comprising 4 to 20 sequential aspartic acid residues,
thereby reducing pathological calcification of vascular tissue in said human subject.

2. The method of claim 1, wherein said soluble polypeptide comprises amino acid residues 96-925 of human ENPP1 (SEQ ID NO: 1).

3. The method of claim 2, wherein said soluble polypeptide is a fusion protein comprising an IgG Fc domain.

4. The method of claim 1, wherein said soluble polypeptide is a fusion protein comprising an IgG Fc domain.

5. The method of claim 1, wherein said soluble polypeptide comprises amino acid residues 93-925 of human ENPP1 (SEQ ID NO: 1).

6. The method of claim 5, wherein said soluble polypeptide is a fusion protein comprising an IgG Fc domain.

7. The method of claim 1, wherein said soluble polypeptide is administered parenterally to said human subject.

8. The method of claim 1, wherein prior to administration of said soluble ENPP1 polypeptide, serum ENPP1 activity is determined in said human subject.

9. The method of claim 1,
wherein said reduced ENPP1 activity is indicated by loss of Pi/PPi homeostasis in said human subject, and
wherein prior to or after said administration of said soluble ENPP1 polypeptide, the level of at least one of serum Pi and serum PPi is determined in said human subject.

10. The method of claim 1,
wherein said method further comprises determining that said ENPP1 activity is reduced in said human subject by detecting a genetic defect associated with reduced ENPP1 activity in said human subject prior to said administration of said soluble polypeptide.

11. A method of reducing pathological calcification of vascular tissue in a human subject in need thereof, wherein said human subject has a loss of function mutation in the gene encoding ecto-nucleotide pyrophosphate/phosphodiesterase-1 (ENPP1),
  wherein said method comprises administering to said subject a therapeutically effective amount of a soluble polypeptide comprising an ENPP1 polypeptide catalytic domain,
    wherein said soluble polypeptide lacks a domain comprising 4 to 20 sequential aspartic acid residues,
  thereby reducing pathological calcification of vascular tissue in said human subject.

12. The method of claim 11, wherein said soluble polypeptide comprises amino acid residues 96-925 of human ENPP1 (SEQ ID NO: 1).

13. The method of claim 12, wherein said soluble polypeptide is a fusion protein comprising an IgG Fc domain.

14. The method of claim 11, wherein said soluble polypeptide is a fusion protein comprising an IgG Fc domain.

15. The method of claim 11, wherein said soluble polypeptide comprises amino acid residues 93-925 of human ENPP1 (SEQ ID NO: 1).

16. The method of claim 15, wherein said soluble polypeptide is a fusion protein comprising an IgG Fc domain.

17. The method of claim 11, wherein said soluble polypeptide is administered parenterally to said human subject.

18. The method of claim 11, wherein prior to administration of said soluble ENPP1 polypeptide, serum ENPP1 activity is determined in said human subject.

19. The method of claim 11,
  wherein said loss of function mutation is indicated by loss of Pi/PPi homeostasis in said human subject, and
  wherein prior to or after said administration of said soluble ENPP1 polypeptide, the level of at least one of serum Pi and serum PPi is determined in said human subject.

20. The method of claim 11,
  wherein said method further comprises detecting said loss of function mutation in said human subject prior to said administration of said soluble polypeptide.

* * * * *